US007605165B2

(12) United States Patent
Sagi et al.

(10) Patent No.: US 7,605,165 B2
(45) Date of Patent: *Oct. 20, 2009

(54) PHENYLALANINE DERIVATIVES

(75) Inventors: Kazuyuki Sagi, Kawasaki (JP); Hiroyuki Izawa, Kawasaki (JP); Akira Chiba, Kawasaki (JP); Tatsuya Okuzumi, Kawasaki (JP); Toshihiko Yoshimura, Kawasaki (JP); Yuji Tanaka, Kawasaki (JP); Miho Ono, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 677 days.

This patent is subject to a terminal disclaimer.

(21) Appl. No.: 10/921,929

(22) Filed: Aug. 20, 2004

(65) Prior Publication Data

US 2005/0101779 A1 May 12, 2005

Related U.S. Application Data

(63) Continuation of application No. PCT/JP03/01852, filed on Feb. 20, 2003.

(30) Foreign Application Priority Data

Feb. 20, 2002 (JP) ............................ 2002-043674

(51) Int. Cl.
*A61K 31/517* (2006.01)
*C07D 239/88* (2006.01)
*C07D 239/96* (2006.01)

(52) U.S. Cl. ............................ 514/266.21; 514/266.3; 544/284; 544/285; 544/286

(58) Field of Classification Search ............ 514/266.21, 514/266.3; 544/284, 285, 286
See application file for complete search history.

(56) References Cited

U.S. PATENT DOCUMENTS

| | | | | |
|---|---|---|---|---|
| 6,610,710 B2 | 8/2003 | Tanaka et al. | |
| 7,153,963 B2 * | 12/2006 | Makino et al. | 544/284 |
| 7,160,874 B2 | 1/2007 | Tanaka et al. | |
| 2005/0222141 A1 * | 10/2005 | Sagi et al. | 514/227.8 |
| 2006/0009476 A1 | 1/2006 | Kataoka et al. | |
| 2006/0204572 A1 * | 9/2006 | Higuchi et al. | 424/464 |
| 2006/0223836 A1 * | 10/2006 | Makino et al. | 514/266.31 |
| 2007/0018172 A1 | 1/2007 | Takahashi et al. | |

FOREIGN PATENT DOCUMENTS

| | | |
|---|---|---|
| EP | 1 233 013 A1 | 8/2002 |
| WO | WO 93/13798 | 7/1993 |
| WO | WO 93/15764 | 8/1993 |
| WO | WO 94/15958 | 7/1994 |
| WO | WO 94/16094 | 7/1994 |
| WO | WO 95/15790 | 6/1995 |
| WO | WO 95/15973 | 6/1995 |
| WO | WO 96/00581 | 1/1996 |
| WO | WO 96/06108 | 2/1996 |
| WO | WO 99/06437 | 2/1999 |
| WO | WO 99/10312 | 3/1999 |
| WO | WO 99/10313 | 3/1999 |
| WO | WO 99/36393 | 7/1999 |
| WO | WO 99/37618 | 7/1999 |
| WO | WO 99/43642 | 9/1999 |
| WO | WO 01/36376 A1 | 5/2001 |
| WO | WO 02/16329 A1 | 2/2002 |

OTHER PUBLICATIONS

Gasperini, C. et. al., "Emerging oral drugs for multiple sclerosis". Expert Opinion Emerging Drugs, (2008), vol. 13, No. 3, pp. 465-477.*
U.S. Appl. No. 10/150,067, filed May 20, 2002, Tanaka, et al.
U.S. Appl. No. 10/252,003, filed Sep. 23, 2002, Izawa, et al.
U.S. Appl. No. 10/300,856, filed Nov. 21, 2002, Makino, et al.
U.S. Appl. No. 10/402,006, filed Mar. 31, 2003, Suzuki, et al.
U.S. Appl. No. 10/763,237, filed Jan. 26, 2004, Chiba, et al.
U.S. Appl. No. 10/866,260, filed Jun. 14, 2004, Okuzumi, et al.
U.S. Appl. No. 11/767,969, filed Jun. 25, 2007, Okuzumi, et al.
U.S. Appl. No. 11/430,284, filed May 9, 2006, Makino, et al.
U.S. Appl. No. 11/018,226, filed Dec. 22, 2004, Sagi, et al.
U.S. Appl. No. 11/963,144, filed Dec. 21, 2007, Sagi, et al.

* cited by examiner

*Primary Examiner*—James O Wilson
*Assistant Examiner*—Tamthom N Truong
(74) *Attorney, Agent, or Firm*—Oblon, Spivak, McClelland, Maier & Neustadt, L.L.P.

(57) ABSTRACT

The present invention relates to the following phenylalanine derivatives or analogues thereof having an antagonistic activity to α4 integrin and therapeutic agents for various diseases concerning α4 integrin.

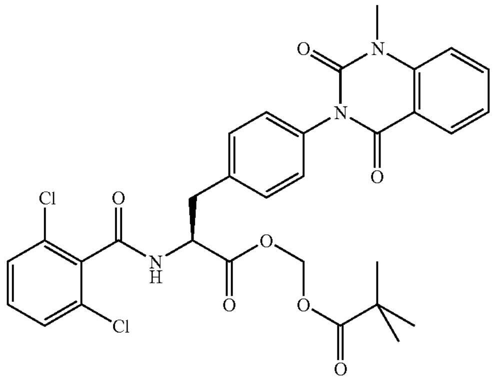

24 Claims, No Drawings

PHENYLALANINE DERIVATIVES

CROSS-REFERENCE TO RELATED APPLICATIONS

This application is a continuation of PCT/JP03/01852, filed on Feb. 20, 2003, which claims priority to JP 2002-43674, filed on Feb. 20, 2002.

BACKGROUND OF THE INVENTION

The present invention relates to new phenylalanine derivatives and the use of the phenylalanine derivatives as medicines. The present invention also relates to the compounds usable as therapeutic agents or preventive agents for inflammatory diseases in which α4 integrin-depending adhesion process participates in the pathology. It was reported that α4 integrins participate in rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection. The compounds of the present invention having an antagonistic effect on the α4 integrins are usable as therapeutic agents or preventive agents for the above-described diseases.

In the inflammatory reactions, it is generally understood that when a microorganism invades a tissue or when the tissue is injured, leukocytes play an important role for the exclusion of the microorganism or for the repair of the injured tissue. It is also widely understood that in such cases, leukocytes usually circulating in the blood must pass through the vascular wall and be newly supplied to the injured tissue. It has been elucidated that the infiltration of the leukocytes from the blood vessel into the tissue is carried out by integrin molecules which are a group of heterodimeric proteins expressing on the leukocytes. The integrin molecules are classified into at least 8 subfamilies (β1 through β8 subfamilies) depending on the β chains thereof. Known typical subfamilies are β1 and β3 subfamilies involved in the adhesion of cell ingredients to the extracellular matrix such as collagen and fibronectin; β2 subfamily involved in cell-to-cell adhesion in the immune system; and β7 subfamily which mainly participates in the infiltration of leukocytes into mucosal tissues (Shimizu et al., Adv. Immunol. 72: 325-380, 1999). As for the above-described β4 integrins, two kinds of molecules thereof are known. They are VLA-4 (very late antigen-4) molecule belonging to the β1 subfamily and comprising a α4β1 chain and LPAM-1 (lymphocyte Peyer's patch HEV adhesion molecule-1) molecule belonging to the β7 subfamily and comprising α4β7 chain. Usually most of leukocytes circulating in the blood have only a low adhesion affinity for the vascular-endothelium cells and they cannot move out of the blood vessel. However, lymphocytes mainly comprising T-cells and B cells are capable of moving out of the blood vessel by a so-called lymphocyte homing phenomenon wherein they move from the blood into the lymphoid tissue through the blood vessel wall and then they return into the blood through the lymphatic vessel under the physiological conditions. It is known that LPAM-1 molecules participate in the lymphocyte homing into the lymphoid tissue of an intestinal tract such as Peyer's patch (Butcher et al., Adv. Immunol. 72: 209-253, 1999). On the other hand, when an inflammation occurs, the vascular-endothelium cells are activated by cytokine and chemokine released from the inflamed tissue, the expression of a group of cell surface antigens (adhesion molecules) participating in the adhesion of leukocytes to the vascular-endothelium cells is caused, and a lot of leukocytes infiltrate out of the blood vessel toward the inflamed tissue through the adhesion molecules.

As the cell surface antigens on the vascular-endothelium cells participating in the adhesion of the leukocytes, there have been known E-selectin (adhesion molecule mainly participating in the adhesion of neutrophils), ICAM-1 and VCAM-1 mainly participating in the adhesion of lymphocytes, and MAdCAM-1 mainly participating in the adhesion of lymphocytes in the lymphoid tissue of an intestinal tract such as Peyer's patch (Shimizu et al., Adv. Immunol. 72: 325-380, 1999). It was reported that in those adhesion molecules, VCAM-1 acts as a ligand of both VLA-4 and LPAM-1 and that MAdCAM-1 acts as the ligand of LPAM-1. As a ligand of both VLA-4 and LPAM-1, fibronectin which is a kind of extracellular matrix is also known (Shimizu et al., Adv. Immunol. 72: 325-380, 1999). The β1 integrin subfamily to which VLA-4 belongs comprises at least 6 integrins (VLA-1 to VLA-6) using extracellular matrixes such as fibronectin, collagen and laminin as the ligands. Many of integrins using extracellular matrixes as the ligands, such as VLA-5, β3 subfamily and β5 subfamily, recognize arginine-glycine-aspartic acid (RGD) sequence in fibronectin, vitronectin, tenascin and osteopontin. On the other hand, in the interaction of VLA-4 and fibronectin, the RGD sequence does not participate but a CS-1 peptide segment comprising leucine-aspartic acid-valine (LDV) as the core sequence participates (Pulido et al., J. Biol. Chem. 266: 10241-10245, 1991). Clements et al. found a sequence similar to LDV in amino acid sequences of VCAM-1 and MAdCAM-1. It has been elucidated that a variant obtained by partially modifying the CS-1-like sequence of VCAM-1 and MAdCAM-1 molecules cannot interact to VLA-4 or LPAM-1 (Clements et al., J. Cell Sci. 107: 2127-2135, 1994, Vonderheide et al., J. Cell. Biol. 125: 215-222, 1994, Renz et al., J. Cell. Biol. 125: 1395-1406, 1994, and Kilger et al., Int. Immunol. 9: 219-226, 1997). Thus, it was found that the CS-1-like sequence is important for the interaction of VLA-4/LPAM-1 and VCAM-1/MAdCAM-1.

It was also reported that the cyclic peptide having the CS-1-like structure is antagonistic both to the interaction of VLA-4 or LPAM-1 with VCAM-1, MAdCAM-1 or CS-1 peptide (Vanderslice et al., J. Immunol. 158: 1710-1718, 1997). The above-described facts indicate that all the interactions of α4 integrin and VCAM-1, MAdCAM-1 or fibronectin can be blocked by using a suitable α4 integrin antagonist (the term "α4 integrin antagonist" in the specification indicates a substance antagonistic to α4β1 and/or α4β7 integrin).

It is also known that the expression of VCAM-1 in vascular-endothelium cells is caused by inflammatory factors such as LPS, TNF-α or IL-1 and that when the inflammation occurs, the infiltration of the leukocytes from the blood vessel into the tissue is carried out by the VLA-4/VCAM-1 adhesion mechanism (Elices, Cell 60: 577-584, 1990, Osborn et al., Cell 59: 1203-1211, 1989 and Issekutz et al., J. Eex. Med. 183: 2175-2184, 1996). Because VLA-4 is expressed on the surfaces of activated lymphocytes, monocytes, eosinophils, mast cells and neutrophils, the adhesion mechanism of VLA-4/VCAM-1 plays an important role for the infiltration of those cells into the inflamed tissue. It was reported that VLA-4 is expressed on various sarcoma cells such as melanoma cells, and it was also elucidated that the adhesion mechanism of VLA-4/VCAM-1 participates in the metastasis of these tumors. By investigating the expression of VCAM-1 in various pathological tissues, it was made apparent that the adhesion mechanism of this VLA-4/VCAM-1 participates in various pathological stages. Namely, it was reported that in addition to the activated vascular-endothelium cells, the expression of VCAM-1 is increased in the inflamed tissues in the patients with autoimmune diseases such as rheumatoid synovial membrane (van Dinther-Janssen, J. Immunol. 147: 4207-4210, 1991 and Morales-Ducret et al., J. Immunol. 149: 1424-1431, 1992), lungs and respiratory tract epithelium in asthma (ten Hacken et al., Clin. Exp. Allergy 12: 1518-1525, 1998) and allergic diseases (Randolph et al., J. Clin. Invest. 104: 1021-1029, 1999), systemic lupus erythematosus (Takeuchi et al., J. Clin. Invest. 92: 3008-3016, 1993), Sjögren's syndrome (Edwards et al., Ann. Rheum. Dis. 52: 806-811, 1993), multiple sclerosis (Steffen et al., Am. J. Pathol. 145: 189-201, 1994) and psoriasis (Groves et al., J. Am. Acad. Dermatol. 29: 67-72, 1993); atherosclerotic plagues (O'Brien et al., J. Clin. Invest. 92: 945-951, 1993), intestinal tissues of the patients with inflammatory bowel diseases such as Crohn's disease and ulcerative colitis (Koizumi et al., Gastroenterol. 103: 840-847, 1992 and Nakamura et al., Lab. Invest. 69: 77-85, 1993), inflamed tissue of Langerhans island of patients with diabetes (Martin et al., J. Autoimmun. 9: 637-643, 1996) and implants during the rejection of transplantation of heart or kidney (Herskowitz et al. Am. J. Pathol. 145: 1082-1094, 1994 and Hill et al., Kidney Int. 47: 1383-1391, 1995). The adhesion mechanism of VLA-4/VCAM-1 participates in these various diseases.

There are many reports showing that in vivo administration of VLA-4 or VCAM-1 antibody was effective in improving the diseases of animal models with those inflammatory diseases. Concretely, Yednock et al. and Baron et al. reported that the in vivo administration of an antibody against α4 integrins was effective in controlling the incidence rate or in controlling encephalomyelitis in the experimental autoimmune encephalomyelitis models, i.e. multiple sclerosis models (Yednock et al., Nature 356: 63-66, 1992 and Baron et al., J. Exp. Med. 177: 57-68, 1993). Zeidler et al. reported that in vivo administration of an antibody against α4-integrin was effective in controlling the incidence rate of mouse collagen arthritis (rheumatoid models) (Zeidler et al., Autoimmunity 21: 245-252, 1995). The therapeutic effect of an antibody against α4-integrin in asthma models was reported by Abraham et al. and Sagara et al. (Abraham et al., J. Clin. Invest. 93: 776-787, 1994 and Sagara et al., Int. Arch. Allergy Immunol. 112: 287-294, 1997). The effect of an antibody against α4-integrin in inflammatory bowel disease models was reported by Podolsky et al. (Podolsky et al., J. Clin. Invest. 92: 372-380, 1993). The effect of an antibody against α4-integrin and that against VCAM antibody in insulin-dependent diabetes models were reported by Baron et al. (Baron et al., J. Clin. Invest. 93: 1700-1708, 1994). It was made apparent with baboon models that the restenosis of a blood vessel after an angioplasty carried out because of arteriosclerosis can be inhibited by the administration of α4 integrin antibody (Lumsden et al., J. Vasc. Surg. 26: 87-93, 1997). It was also reported that α4 integrin or VCAM antibody is effective in inhibiting the rejection of an implant or inhibiting metastasis of a cancer (Isobe et al., J. Immunol. 153: 5810-5818, 1994 and Okahara et al., Cancer Res. 54: 3233-3236, 1994).

As described above, unlike VCAM-1, MAdCAM-1 which is a ligand of LPAM-1 is constitutively expressed on high endothelial venules (HEV) in the intestinal mucosa, mesenteric lymphatic nodes, Peyer's patch and spleen and it participates in the homing of mucosal lymphocytes. It is also known that LPAM-1/MAdCAM-1 adhesion mechanism not only has physiological roles in the homing of the lymphocytes but also participates in some pathological processes. Briskin et al reported an increase in the expression of MAdCAM-1 in inflamed regions in intestinal tracts of patients with inflammatory bowel diseases such as Crohn's disease and ulcerative colitis (Briskin et al., Am. J. Pathol. 151: 97-110, 1997). Hanninen et al. reported that induction of the expression is observed in an inflamed tissue of Langerhans island of NOD mouse which is a model of an insulin-dependent diabetes (Hanninen et al., J. Immunol. 160: 6018-6025, 1998). The fact that LPAM-1/MAdCAM-1 adhesion mechanism participates in the progress of diseases is apparent from the fact that conditions of mouse models with inflammatory bowel disease (Picarella et al., J. Immunol. 158: 2099-2106, 1997) and the above-described NOD mouse models are improved by the in vivo administration of antibody to MAdCAM or antibody to β7 integrin (Hanninen et al., J. Immunol. 160: 6018-6025, 1998 and Yang et al., Diabetes 46: 1542-1547, 1997).

The above-described facts indicate the possibility in that employing the blocking of VLA-4/VCAM-1, LPAM-1/VCAM-1 or LPAM-1/MAdCAM-1 adhesion mechanism by a suitable antagonist is effective in treating the chronic inflammatory diseases described above. The use of the antibody against VLA-4 as the VLA-4 antagonist is described in WO 93/13798, WO 93/15764, WO 94/16094 and WO 95/19790. Peptide compounds as VLA-4 antagonists are described in WO 94/15958, WO 95/15973, WO 96/00581 and WO 96/06108. Amino acid derivatives usable as VLA-4 antagonists are described in WO 99/10312, WO 99/10313, WO 99/36393, WO 99/37618 and WO 99/43642. However, none of them is practically used for the therapeutic treatment at present because of the lack of oral bioavailability and immunogenic properties during the use of them for a long period of time.

DISCLOSURE OF THE INVENTION

An object of the present invention is to provide new compounds having α4 integrin antagonistic effect in vivo.

Another object of the present invention is to provide the compounds having α4 integrin antagonistic effect in vivo, which can be administered orally.

Still another object of the present invention is to provide α4 integrin antagonists.

A further object of the present invention is to provide a pharmaceutical composition containing such new compounds.

An additional object of the present invention is to provide therapeutic agents or preventive agents for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

For the purpose of solving the above-described problems, the inventors have synthesized various phenylalanine derivatives and examined α4 integrin antagonistic activities thereof, and the inventors have found that specified, new phenylalanine derivatives have an excellent α4 integrin antagonistic activity, and then the inventors have synthesized the phenylalanine derivatives wherein a carboxyl group(s) thereof are substituted with various organic groups which are converted into a carboxyl group in vivo. The present invention has been completed on the basis of this finding.

Namely, the present invention provides phenylalanine derivatives of the following general formula (1) and pharmaceutically acceptable salts thereof:

(1)

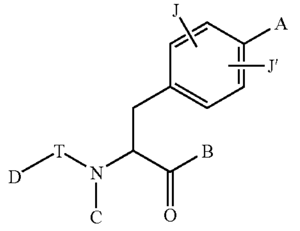

wherein A represents one of the following general formulae (2), (3), (3-1) or (3-2):

(2)

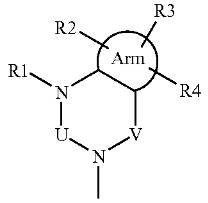

(3)

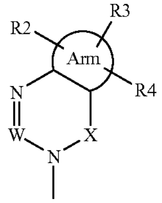

(3-1)

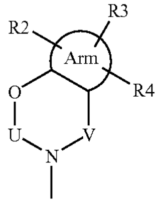

(3-2)

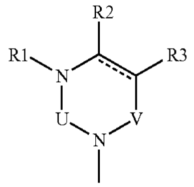

wherein Arm represents a cyclic alkyl group or an aromatic ring containing 0, 1, 2, 3 or 4 hetero atoms selected from the group consisting of oxygen, sulfur and nitrogen atoms, the composite line of solid line and dotted line in the formula (3-2) represents a single bond or a double bond, U, V and X represent C(═O), $S(═O)_2$, C(—R5)(—R6), C(═C(R5)(R6)), C(═S), S(═O), P(═O)(—OH) or P(—H)(═O), W represents C(—R7) or a nitrogen atom, R1, R2, R3, R4 R5, R6 and R7 may be the same or different from one another and each represent a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxylalkoxyl group, a lower halogenoalkyl group, a lower halogeno alkoxyl group, a lower halogenoalkylthio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or an ammonium group, R5 and R6 may be bonded together to form a ring which may contain one or two oxygen, nitrogen or sulfur atoms, B represents a lower alkoxyl group having a substituent(s), a substituted or unsubstituted amino group (except for a hydroxylamino group) or a substituted or unsubstituted mercapto group, C represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, C and D may be bonded together to form a ring which may contain one or two oxygen, nitrogen or sulfur atoms, T represents an interatomic bond, C(═O), C(═S), S(═O), $S(═O)_2$, N(H)—C(═O), or N(H)—C(═S), J and J' may be the same or different from each other and each represent a hydrogen atom, a halogen atom, a lower alkyl group, a lower alkyloxy group or nitro group.

The present invention provides an α4 integrin antagonist containing the above-described phenylalanine derivative or a pharmaceutically acceptable salt thereof as the active ingredient.

The present invention also provides a pharmaceutical composition containing the above-described phenylalanine derivative or a pharmaceutically acceptable salt thereof.

The present invention further provides a therapeutic agent or preventive agent, containing the phenylalanine derivative or a pharmaceutically acceptable salt thereof as the active ingredient, for diseases in which α4 integrin-depending adhesion process participates in the pathology, such as inflammatory diseases, rheumatoid arthritis, inflammatory bowel diseases, systemic lupus erythematosus, multiple sclerosis, Sjögren's syndrome, asthma, psoriasis, allergy, diabetes, cardiovascular diseases, arterial sclerosis, restenosis, tumor proliferation, tumor metastasis and transplantation rejection.

BEST MODE FOR CARRYING OUT THE INVENTION

The term "lower" in, for example, a lower alkyl group in the present specification indicates that the group has 1 to 6 carbon atoms and preferably 1 to 4 carbon atoms. Alkyl groups, alkenyl groups and alkynyl groups in alkyl groups, alkenyl groups, alkynyl groups, alkoxyl groups, alkylthio groups, alkanoyl groups, alkylamino groups and the like may be either linear or branched. Examples of these alkyl groups are methyl group, ethyl group, propyl group, isopropyl group, butyl group, secondary butyl group, tertiary butyl group, pentyl group and hexyl group. It is preferable that the alkyl groups have 1 to 6 carbon atoms and more preferable that the groups have 1 to 4 carbon atoms. The alkenyl groups are, for example, vinyl group, propenyl group, butenyl group and pentenyl group. It is preferable that the alkenyl groups have 2 to 6 carbon atoms and more preferable that the groups have 2 to 4 carbon atoms. The alkynyl groups include ethynyl group, propynyl group and butynyl group. It is preferable that the alkenyl groups have 2 to 8 carbon atoms and more preferable that the groups have 2 to 4 carbon atoms. The cycloalkyl groups indicate substituted or unsubstituted cycloalkyl groups such as cyclopropyl group, cyclobutyl group, cyclopentyl group, cyclohexyl group, norbornyl group, adamantyl group and cyclohexenyl group. It is preferable that the cycloalkyl groups have 3 to 8 carbon atoms and more preferable that the groups have 3 to 5 carbon atoms. The alkoxyl groups include methoxyl group, ethoxyl group, propyloxy group, isopropyloxy group, cyclopropoxy group, cyclobutoxy group, cyclopentyloxy group, cyclohexyloxy group, etc. When a hydrocarbon group forming the alkoxyl group is a chain group, it is preferable that the alkoxyl group has 1 to 6 carbon atoms and more preferable that the group has 1 to 4 carbon atoms. When a hydrocarbon group forming the alkoxyl group is an alicyclic group, it is preferable that the alkoxyl group has 3 to 6 carbon atoms and more preferable that the group has 5 to 6 carbon atoms. The hetero atoms include nitrogen, oxygen, sulfur, etc. The halogen atoms are fluorine, chlorine, bromine and iodine. The halogenoalkyl groups include chloromethyl group, trichloromethyl group, trifluoromethyl group, trifluoroethyl group, pentafluoroethyl group, etc. The halogenoalkoxyl groups include trichloromethoxyl group, trifluoromethoxyl group, etc. The hydroxyalkyl groups include hydroxymethyl group, hydroxyethyl group, etc. The cycloalkyl groups which may contain a hetero atom(s) in the ring thereof may be either substituted or unsubstituted. Examples of them include cyclopentyl group, cyclohexyl group, piperidyl group, piperazinyl group, morpholinyl group, pyrrolidinyl group, tetrahydrofuranyl group and uracil group, which are 4-to-8-membered cyclic group, preferably, 5-to-7-membered cyclic group.

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups and halogenoalkoxyl groups. The heteroaryl groups are both substituted and unsubstituted heteroaryl groups such as pyridyl group, pyrazyl group, pyrimidinyl group, pyrazolyl group, pyrrolyl group, triazinyl group, furyl group, thienyl group, isoxazolyl group, isothiazolyl group, indolyl group, quinolyl group, isoquinolyl group and benzimidazolyl group. Preferred heteroaryl groups are pyridyl group, pyrazyl group, pyrimidinyl group, furyl group, thienyl group and substituted pyridyl, furyl and thienyl groups. Particularly preferred substituents are halogen atoms, alkoxyl groups, alkyl groups, hydroxyl group, halogenoalkyl groups and halogenoalkoxyl groups. The lower alkyl groups substituted with an aryl group(s) include, for example, substituted or unsubstituted benzyl groups and substituted or unsubstituted phenethyl groups. Particularly preferred substituents are halogen atoms, alkoxyl groups, alkyl groups, hydroxyl group, halogenoalkyl groups and halogenoalkoxyl groups. The lower alkyl groups substituted with a heteroaryl group(s) include, for example, pyridylmethyl group, and particularly preferred substituents thereof are halogen atoms, alkoxyl groups, alkyl groups, hydroxyl group, halogenoalkyl groups and halogenoalkoxyl groups. The alkanoyl groups include, for example, formyl groups, acetyl groups, propanoyl group, butanoyl group and pivaloyl group. The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups. The halogenoalkanoyl groups include, for example, trichloroacetyl group and trifluoroacetyl group. The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The halogenoalkylsulfonyl groups include, for example, trifluoromethanesulfonyl group. The alkyloxycarbonyl groups include, for example, methoxycarbonyl group, ethoxycarbonyl group and tert-butoxycarbonyl group. The aryl-substituted alkoxycarbonyl groups include, for example, benzyloxycarbonyl group and 9-fluorenylmethoxycarbonyl group. The substituted carbamoyl groups include, for example, methylcarbamoyl group, dimethylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups. The substituted thiocarbamoyl groups include, for example, methylthiocarbamoyl group, phenylthiocarbamoyl group and substituted phenylthiocarbamoyl groups, and the substituents thereof are particularly preferably halogens, alkoxyl groups, alkyl groups, hydroxyl group, halogenoalkyl groups and halogenoalkoxyl groups. The substituted amino groups in this specification indicate mono-substituted or di-substituted amino groups and the substituents thereof include lower alkyl groups, lower alkyl groups substituted with an aryl group, lower alkyl groups substituted with a heteroaryl group, lower alkanoyl groups, aroyl groups, lower halogenoalkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups. The two substituents of the amino group may be bonded together to form a ring and one or more hetero atoms such as oxygen, nitrogen, sulfur, etc. may be contained in bonding for formation of the ring. Such cyclic amino groups include 1-pyrrolidinyl group, 1-piperidinyl group, 4-morpholinyl group, 1-indolinyl group and 4-thiomorpholinyl group. Further, cyclic amide groups such as 2-oxo-1-pyrrolidinyl group and cyclic urea groups such as 2-oxoimidazolidine-1-yl group are also included. The ammonium groups include such as trialkylammonium groups. The acyl groups used in the present specification include alkanoyl groups and aroyl groups and the alkanoyl groups are preferable. The acyl groups herein represent those having 1 to 20 carbon atoms and preferably those having 5 to 16 carbon atoms. The acyl groups having 2 to 3 carbon atoms are also preferable. A hydrocarbon moiety forming the acyl group may be either linear or branched. Examples thereof are acetyl group, propionyl group, butyryl group, valeryl group, palmitoyl group, stearoyl group, oleoyl group, benzoyl group, salicyloyl group and phthaloyl group.

Because the phenylalanine derivatives of the general formula (1) of the present invention include asymmetric carbons, it can be considered that the phenylalanine derivatives of the general formula (1) of the present invention are optical isomers and the compound indicated in the present invention include the said optical isomers. However, L-form is preferable.

Regarding the compound in which a diastereomer exists, the diastereomer and the diastereomer mixture are included in the said phenylalanine derivatives. Because the phenylalanine derivatives of the general formula (1) of the present invention include a movable hydrogen atom, it can be considered that the phenylalanine derivatives of the general formula (1) of the present invention include a variety of tautomeric forms and the compounds indicated in the present invention include the said tautomeric forms. Further, when the compound of the present invention has carboxyl groups, the carboxyl groups thereof may be substituted with appropriate substituents which are converted into a carboxyl group in vivo. An example of such substituents is a lower alkoxycarbonyl group.

In the above-described general formula (1), it is preferable that the groups indicated as A are both the general formulae (2) and (3), Arm in the general formulae (2) and (3) is preferably an aromatic ring and particularly a benzene ring and substituted benzene ring are preferable. R1 in the general formula (2) is preferably a hydrogen atom, a lower alkyl group and substituted lower alkyl group. Substituents thereof are preferably a phenyl group, cyano group and carboxyl group. It is preferable that R2 to R4 of the general formulae (2) and (3) are a hydrogen atom, a halogen, a hydroxyl group, a lower alkyl group, a lower alkoxy group, a halogen lower alkyl group, a substituted or unsubstituted amino group and an ammonium group.

B represents a lower alkoxyl group having a substituent(s), a substituted or unsubstituted amino group (except for a hydroxylamino group) or a substituted or unsubstituted mercapto group.

When B has a substituent(s), the substituents are, for example, those described above with reference to R1, R2, R3, R4, R5, R6 and R7. However, an unsubstituted lower alkoxyl group is not included in B.

The group represented by B is preferably an organic group represented by the following formula (B-1) or (B-2), a substituted or unsubstituted amino group, or a substituted or unsubstituted mercapto group:

—O—Y—E (B-1)

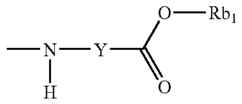
(B-2)

wherein Y represents a substituted or unsubstituted divalent lower hydrocarbon group, E represents a substituted or unsubstituted acyloxy group, a substituted or unsubstituted lower alkoxycarbonyloxy group, a substituted or unsubstituted amino group, carboxyl group, a substituted or unsubstituted lower alkoxycarbonyl group, a halogen atom, an aryl group, a heteroaryl group, a substituted or unsubstituted alkoxyl group or a substituted or unsubstituted carbamoyl group, $Rb_1$ represents a hydrogen atom or a lower alkyl group, and Y and E may be bonded together to form a ring.

When a group B represents a substituted amino group, the substituents thereof are one or two lower alkyl groups. The substituents are preferably methyl group, ethyl group or propyl group. The substituted amino group herein includes a cyclic amino group such as 1-piperidinyl group and 4-morpholinyl group.

When a group B represents a substituted mercapto group, the substituents thereof are lower alkyl groups. The substituents are preferably methyl group, ethyl group or propyl group.

A divalent lower hydrocarbon group herein indicates an alkylene group, alkenylene group or alkynylene group having 1 to 6 carbon atoms and preferably having 1 to 4 carbon atoms, or a bonded form of such groups. When these groups are bonded to form a divalent lower hydrocarbon group, the total number of carbon atoms included in the groups are 3 to 6 and preferably 3 to 4. Examples thereof are methylene group, ethylene group and propenylene group. Methylene group and ethylene group are preferable. The divalent lower hydrocarbon group may be substituted with one or two substituents. The substituents thereof include a lower alkyl group, an acyloxy lower alkyl group, a hydroxyl group, a halogeno group, a substituted or unsubstituted amino group and the like. Methyl group and palmitoyloxymethyl group are preferable.

A group E represents a substituted or unsubstituted acyloxy group, a substituted or unsubstituted lower alkoxycarbonyloxy group, a substituted or unsubstituted amino group, carboxyl group, a substituted or unsubstituted lower alkoxycarbonyl group, a halogen atom, an aryl group, a heteroaryl group, a substituted or unsubstituted alkoxyl group or a substituted or unsubstituted carbamoyl group.

It is preferable that E is a substituted or unsubstituted acyloxy group, a substituted or unsubstituted lower alkoxycarbonyloxy group, a substituted or unsubstituted amino group, carboxyl group or a substituted or unsubstituted lower alkoxycarbonyl group. A substituted or unsubstituted acyloxy group, a substituted or unsubstituted lower alkoxycarbonyloxy group and a substituted or unsubstituted amino group are particularly preferable.

A substituted or unsubstituted alkoxyl group and a chlorine atom are also preferable.

When a group E represents a substituted acyloxy group, the substituents thereof include a lower alkyl group, a lower alkenyl group, a substituted or unsubstituted amino group, a hydroxyl group, an alkoxyl group, a halogen atom and the like. The substituents are preferably a hydroxyl group or a fluorine atom.

When a group E represents a substituted lower alkoxycarbonyloxy group, the substituents thereof include a lower alkyl group, a lower alkenyl group, a substituted or unsubstituted amino group, a hydroxyl group, an alkoxyl group, a halogen atom and the like. The substituents are preferably a hydroxyl group or a fluorine atom.

When a group E represents a substituted amino group, the substituents thereof include a lower alkyl group, a lower alkanoyl group, a substituted sulfonyl group and the like. The substituents are preferably methyl group or ethyl group. The substituted amino group herein includes a cyclic amino group such as 1-piperidinyl group and 4-morpholinyl group. Further, the substituted amino group represented by E is preferably, for example, a cyclic amide group such as 2-oxo-1-pyrrolidinyl group or a cyclic urea group such as 2-oxoimidazolidine-1-yl group.

When a group E represents a substituted lower alkoxycarbonyl group, the substituents thereof include a lower alkyl group, a hydroxyl group, a halogeno group and a substituted or unsubstituted amino group. The substituents are preferably a chlorine atom or a fluorine atom.

An aryl group represented by E is preferably a phenyl group.

A heteroaryl group represented by E is preferably a furyl group, pyridyl group or thienyl group and particularly preferably a furyl group.

A group $Rb_1$ represents a hydrogen atom or a lower alkyl group.

A lower alkyl group is preferable and more concretely a methyl group, an ethyl group and a propyl group are preferable.

B wherein Y and E are bonded together to form a ring represents following groups.

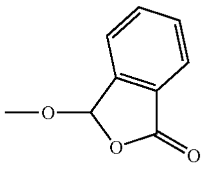

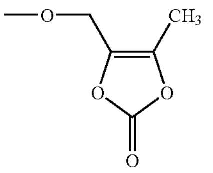

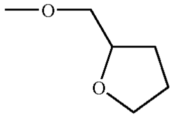

A group represented by B is preferably an organic group represented by the above formula (B-1) or (B-2), a substituted or unsubstituted amino group or a substituted or unsubstituted mercapto group, and when B represents the formula (B-1) or (B-2), Y represents a substituted or unsubstituted divalent lower hydrocarbon group, E represents a substituted or unsubstituted acyloxy group, a substituted or unsubstituted lower alkoxycarbonyloxy group, a substituted or unsubstituted amino group, carboxyl group or a substituted or unsubstituted lower alkoxycarbonyl group, $Rb_1$ represents a hydrogen atom or a lower alkyl group, and Y and E may be bonded together to form a ring.

The group represented by B is also preferably an organic group represented by the formula (B-1) or a substituted or unsubstituted amino group, and when B represents the formula (B-1), Y represents a substituted or unsubstituted divalent lower hydrocarbon group, E represents a substituted or unsubstituted acyloxy group, a substituted or unsubstituted lower alkoxycarbonyloxy group, a substituted or unsubstituted amino group, a halogen atom, an aryl group, a heteroaryl group, an alkoxyl group or a substituted or unsubstituted carbamoyl group.

The group represented by B is further more preferably a group represented by the formula (B-1) or a substituted or unsubstituted amino group and the preferred substituents of the amino group are described above.

When B represents a group represented by the formula (B-1), it is preferable that Y is a substituted or unsubstituted methylene group, a substituted or unsubstituted ethylene group or substituted or unsubstituted trimethylene group, and E is a substituted or unsubstituted acyloxy group, a substituted or unsubstituted lower alkoxycarbonyloxy group or a substituted or unsubstituted amino group. The preferred substituents of each of Y and E are described above.

The group represented by B is also preferably an amino group substituted with a lower alkyl group, an unsubstituted amino group or a group represented by the formula (B-1), in the formula (B-1), Y is a substituted or unsubstituted methylene group, a substituted or unsubstituted ethylene group or substituted or unsubstituted trimethylene group, and E is a substituted or unsubstituted acyloxy group, preferably a substituted or unsubstituted lower acyloxy group, a chlorine atom, a fluorine atom, a substituted or unsubstituted furyl group, a substituted or unsubstituted phenyl group, a substituted or unsubstituted thienyl group, a substituted or unsubstituted pyridyl group, a lower alkoxyl group, a carbamoyl group which may be substituted with a lower alkyl group, a substituted or unsubstituted lower alkoxycarbonyloxy group or a substituted or unsubstituted amino group.

The group represented by B is more preferably a group represented by the formula (B-1) or a substituted or unsubstituted amino group in the formula (1), and when B represents the formula (B-1), it is preferable that Y is a substituted or unsubstituted methylene group and E is a substituted or unsubstituted acyloxy group or a substituted or unsubstituted lower alkoxycarbonyloxy group, or it is also preferable that Y is a substituted or unsubstituted ethylene group or a substituted or unsubstituted trimethylene group and E is a substituted or unsubstituted amino group, or it is also preferable that Y is a ethylene group having an acyloxymethyl group as a substituent and E is a substituted or unsubstituted acyloxy group. The preferred substituents of each of Y and E are described above.

The group represented by B is also preferably an amino group substituted with one lower alkyl group, an unsubstituted amino group or a group represented by the formula (B-1), in the formula (B-1), Y is a methylene group substituted with a lower alkyl group or unsubstituted methylene group, and E is a substituted or unsubstituted lower acyloxy group, a chlorine atom, a fluorine atom, a substituted or unsubstituted furyl group, a carbamoyl group which may be substituted with a lower alkyl group or a substituted or unsubstituted lower alkoxycarbonyloxy group, or Y is a substituted or unsubstituted ethylene group or a substituted or unsubstituted trimethylene group, and E is a lower alkoxyl group or an amino group substituted with a lower alkyl group.

The group represented by B is more preferably a group represented by the formula (B-1), an amino group substituted with one lower alkyl group or unsubstituted amino group in the formula (1), and when B represents the formula (B-1), it is preferable that Y is a methylene group substituted with a lower alkyl group or unsubstituted methylene group and E is a substituted or unsubstituted lower acyloxy group or a substituted or unsubstituted lower alkoxycarbonyloxy group and the preferred substituents of each of Y and E are described above, or that Y is a substituted or unsubstituted ethylene group or a substituted or unsubstituted trimethylene group and E is an amino group substituted with a lower alkyl group and the preferred substituents of Y are a lower alkyl group, hydroxyl group and halogeno group and those of E are cyclic amino groups.

The group represented by B is more preferably a group represented by the formula (B-1) or an amino group substituted with one lower alkyl group, and when B represents the formula (B-1), it is preferable that Y is a methylene group substituted with a lower alkyl group and E is an unsubstituted lower alkoxycarbonyloxy group, or that Y is an unsubstituted methylene group and E is an unsubstituted lower acyloxy group, or that Y is an unsubstituted ethylene group and E is a cyclic amino group. The preferred substituents of each of Y and E are described above.

A group represented by B is also preferably a group represented by the formula (B-1), wherein Y is an unsubstituted methylene group and E is an unsubstituted lower acyloxy group, a chlorine atom, a furyl group or dimethylcarbamoyl group, or wherein Y is an unsubstituted ethylene group and E is a lower alkoxyl group.

The group represented by C is preferably a lower alkyl group or a hydrogen atom and the hydrogen atom is more preferable.

As the groups represented by D, the cycloalkyl groups which may contain a hetero atom(s) in the ring thereof, aryl groups and heteroaryl groups are preferable. The cycloalkyl groups which may contain a hetero atom(s) in the ring thereof, aryl groups and heteroaryl groups are either unsubstituted or substituted, and the substituents are those described above with reference to R1, R2, R3, R4, R5, R6 and R7. Among these, the groups represented by D are particularly preferably substituted or unsubstituted cyclohexyl group or phenyl group. The substituents thereof are preferably 1 to 3 of, more preferably, 1 or 2 of lower alkyl groups or lower alkoxyl groups or halogen atoms.

The group represented by J and J' is preferably a hydrogen atom.

The group represented by T is preferably C(═O).

It is preferred that U, V and X are C(═O) and C(═S), and C(═O) is particularly preferred. W is preferably C(—R7) and —R7 is preferably a lower alkyl group, a lower alkoxyl group and a lower alkylthio group.

In the general formula (1) of the present invention, it is preferable that A represents one of the groups indicated as the general formula (2) or (3) and R1, R2, R3, R4, R5, R6 and R7 may be the same or different from one another, and each represents the groups shown below: a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkylthio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group or a substituted or unsubstituted sulfamoyl group, R5 and R6 may be bonded together to form a ring which may contain one or two oxygen, nitrogen or sulfur atoms. It is further more preferable that B is the compound defined as the groups preferable as B.

It is preferable that, in the general formula (1) of the present invention,

C represents a hydrogen atom or a lower alkyl group,

J and J' represent a hydrogen group, and in the general formulae (2) and (3), V and X represent any of group of C═(O), $S(═O)_2$ or C(—R5)(—R6), U represents any of group of C═(O), $S(═O)_2$, C(—R5)(—R6), C(═C(R5)(R6)), C(═S), S(═O), P(═O)(—OH) or P(—H)(═O). It is further more preferable that B is the compound defined as the groups preferable as B.

Further, it is preferable that, in the general formula (1),

C represents a hydrogen atom or a lower alkyl group,

J and J' represent a hydrogen group, and in the general formulae (2) and (3), Arm represents a benzene ring or an aromatic ring containing 1, 2, 3 or 4 hetero atoms selected from the group consisting of oxygen, sulfur and nitrogen atoms. It is further more preferable that B is the compound defined as the groups preferable as B.

Further, it is preferable that, in the general formula (1),

C represents a hydrogen atom or a lower alkyl group,

J and J' represent a hydrogen group, and in the general formulae (2) and (3), Arm represents a benzene ring or an aromatic ring containing 1, 2, 3 or 4 hetero atoms selected from the group consisting of oxygen, sulfur and nitrogen atoms, V and X represent any of group of C(═O), S(═O)$_2$ or C(—R5)(—R6), U represents any of group of C(═O), S(═O)$_2$, C(—R5)(—R6), C(═C(R5)(R6)), C(═S), S(═O), P(═O)(—OH) and P(—H)(═O). It is further more preferable that B is the compound defined as the groups preferable as B.

It is also preferred that, in the general formula (1), C represents a hydrogen atom and T represents C(═O). It is further more preferable that B is the compound defined as the groups preferable as B.

It is still preferred that, in the general formula (1), A represents the following formula (3-3):

(3-3)

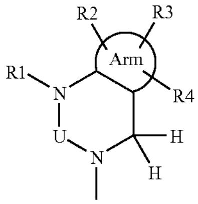

wherein Arm, U and R1 to R4 are the same as those described above.

In the general formula (3-3), Arm is preferably an aromatic ring, and particularly preferably a benzene ring or substituted benzene ring. R1 in the general formula (3-3) is preferably a hydrogen atom, lower alkyl group or a lower alkyl group substituted with phenyl group, cyano group or carboxyl group. R2 to R4 in the general formula (3-3) are preferably a hydrogen atom, halogen atom, hydroxyl group, lower alkyl group, lower alkoxyl group, cyano group, nitro group, an unsubstituted amino group or amino group substituted with a lower alkyl group(s). It is further more preferable that B is the compound defined as the groups preferable as B.

In the general formula (1), A preferably represents the following formula (3-4) or (3-5):

(3-4)

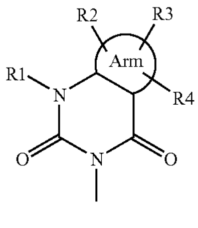

(3-5)

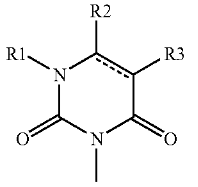

wherein Arm and R1 to R4 are the same as those described above, and the composite line of solid line and dotted line in the formula (3-5) represents a single bond or a double bond. It is further more preferable that B is the compound defined as the groups preferable as B.

In the general formula (1), D preferably represents the following formulae (4-1), (4-2), (4-3) or (4-4):

(4-1)

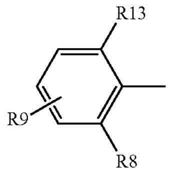

(4-2)

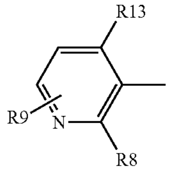

(4-3)

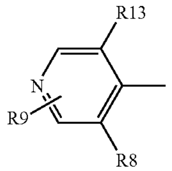

(4-4)

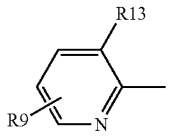

wherein R13 represents a halogen atom or methyl group, R8 represents a halogen atom, methyl group, trifluoromethyl group, methoxy group or a hydrogen atom, R9 represents a hydrogen atom, halogen atom, hydroxyl group, lower alkyl group, cycloalkyl group which may contain a hetero atom(s) in the ring thereof, lower alkyl group substituted with a cycloalkyl group(s) which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), trialkylammonium group, methanesulfonyl amino group and tetrazolyl group. It is further more preferable that B is the compound defined as the groups preferable as B.

In the above formulae, the formula (4-1) is preferable. Particularly, it is preferable that in the formula (4-1), R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogeno alkoxyl group, lower halogenoalkylthio group, nitro group, cyano group, amino group, amino group substituted with a lower alkyl group(s) or trialkylammonium group.

It is also preferable that in the general formula (1), A represents the formula (3-4), Arm is a benzene ring, pyridine ring, pyrazole ring or cyclohexane ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group. It is further more preferable that B is the compound defined as the groups preferable as B.

Further, it is preferred that in the general formula (1), A represents the formula (3-4) or (3-5), D represents (4-1), (4-2), (4-3) or (4-4), C is a hydrogen atom, each of J and J' is a hydrogen atom and T is C(=O). It is further more preferable that B is the compound defined as the groups preferable as B.

In the present invention, it is preferable that in the general formula (1), A represents the formula (3-4) wherein Arm is a benzene ring, pyridine ring, pyrazole ring or cyclohexane ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, D represents the formula (4-1) wherein R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogeno alkoxyl group, lower halogenoalkylthio group, nitro group, cyano group, amino group, amino group substituted with a lower alkyl group(s) or trialkylammonium group, C is a hydrogen atom, each of J and J' is a hydrogen atom and T is C(=O). It is further more preferable that B is the compound defined as the groups preferable as B.

In the present invention, it is also preferred that in the general formula (1), A represents the formula (3-3), and in the formula (3-3), U represents C(=O) or C(=S), R1 represents a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, C represents a hydrogen atom, D represents the formula (4-1), (4-2), (4-3) or (4-4), T represents C(=O). It is further more preferable that B is the compound defined as the groups preferable as B.

Further, in the present invention, it is preferred that A represents the formula (3-3), and in the formula (3-3), U represents C(=O) or C(=S), R1 represents a methyl group or ethyl group, R2, R3 and R4 may be the same or different from one another and each represent a hydrogen atom, a halogen atom, a hydroxyl group, a lower alkyl group, a cycloalkyl group-which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, C represents a hydrogen atom, D represents the formula (4-1), wherein R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s) or trialkylammonium group, T is C(=O) and each of J and J' is a hydrogen atom. It is further more preferable that B is the compound defined as the groups preferable as B.

In the present invention, phenylalanine derivatives of the following general formula and pharmaceutically acceptable salts thereof is preferable:

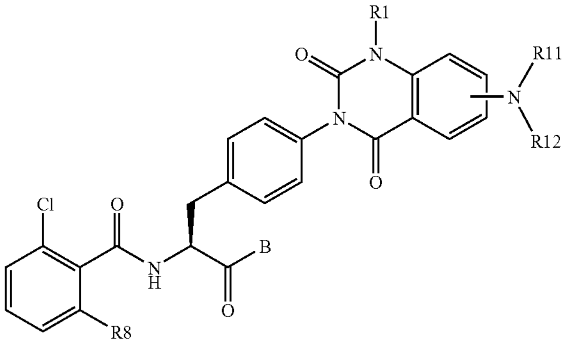

wherein R1 represents a methyl group or ethyl group, R8 represents a halogen atom or methyl group, R11 and R12 may be the same or different from each other and each represents a hydrogen atom, methyl group, ethyl group or propyl group, R11 and R12 may be bonded together to form a ring, and in that case, R11-R12 represent trimethylene, tetramethylene or pentamethylene and B is the same as the formula (1). It is further more preferable that B is the compound defined as the groups preferable as B.

More concretely, the compounds described in Examples are preferable though they are not particularly limited.

Especially, the following compounds are preferred:

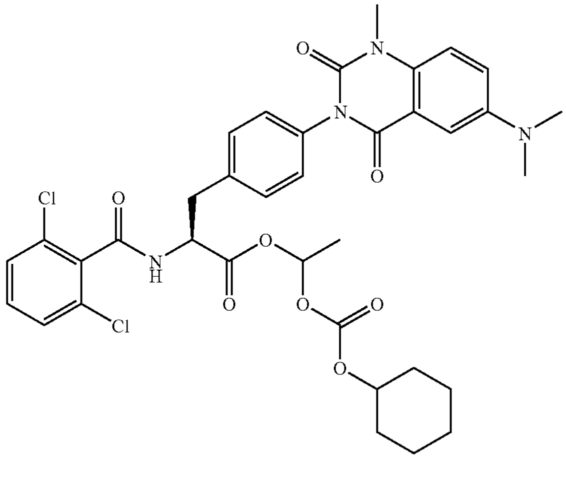

-continued
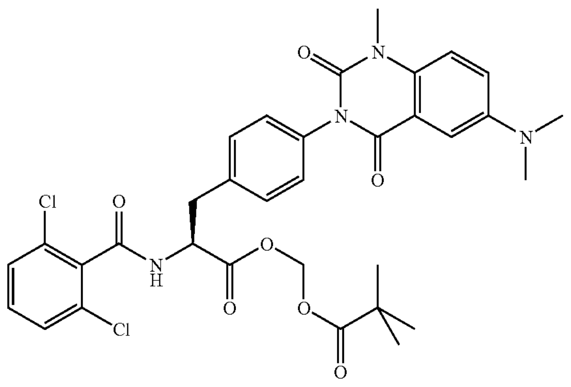
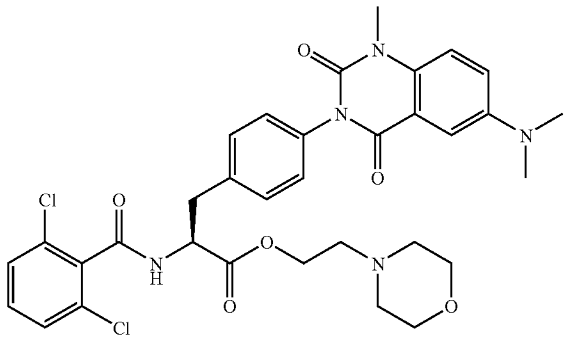
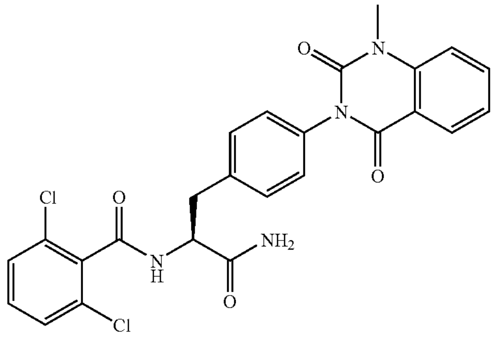
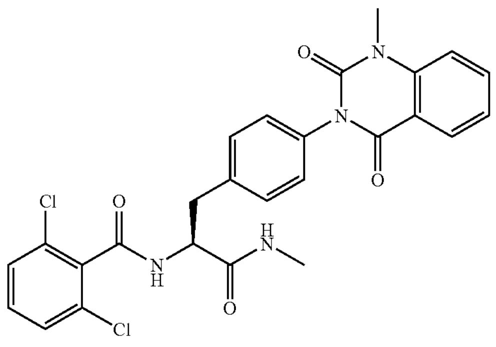
-continued
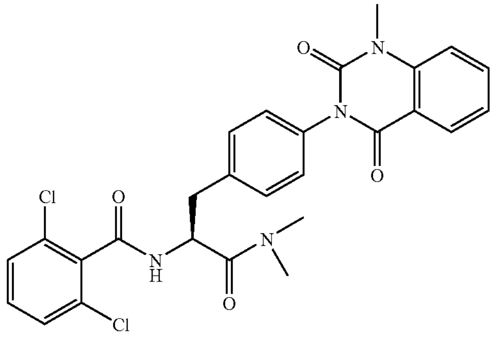
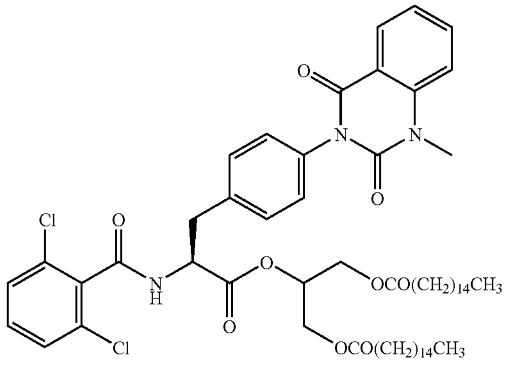
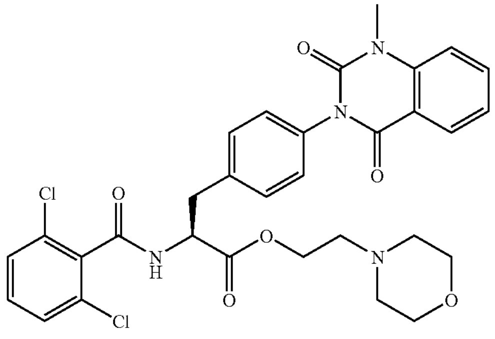
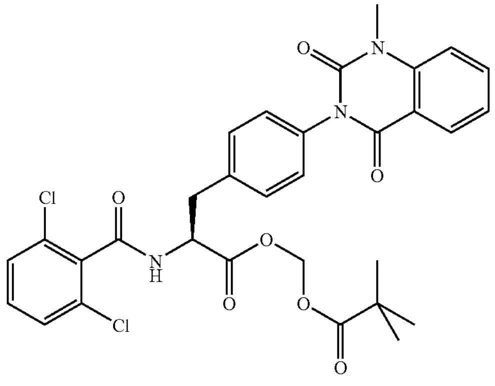

-continued
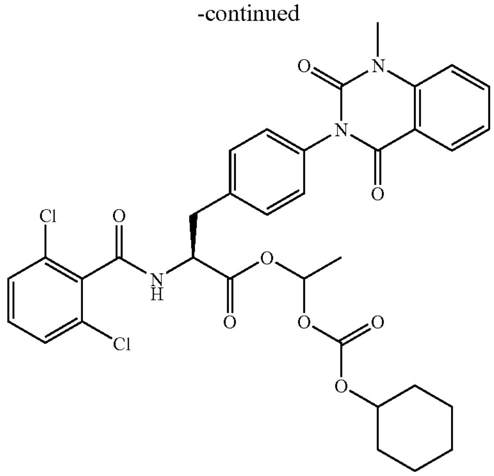
The following compounds are also preferred:
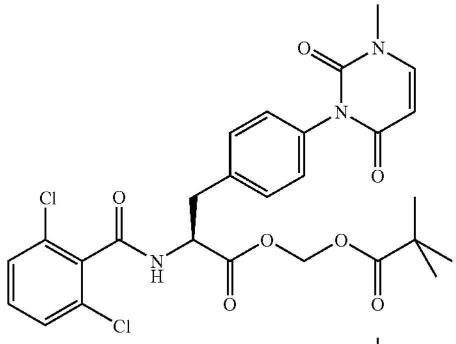
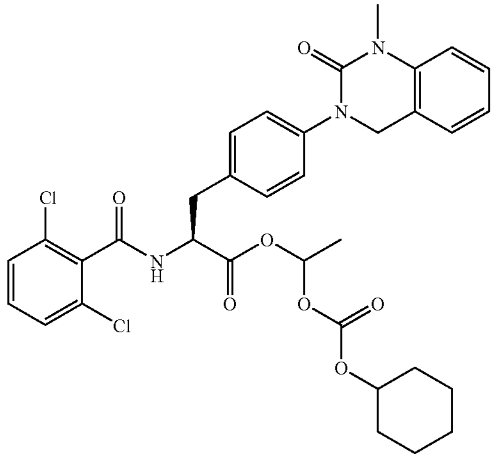
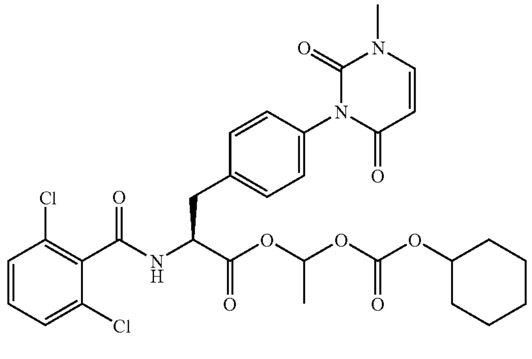
-continued
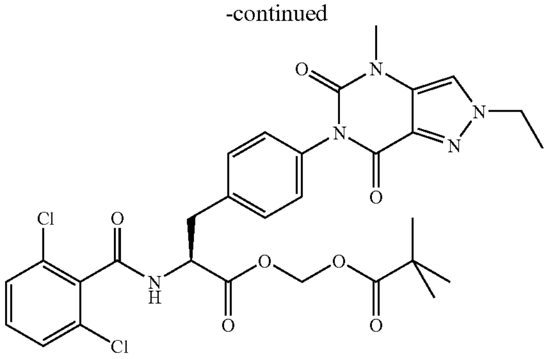
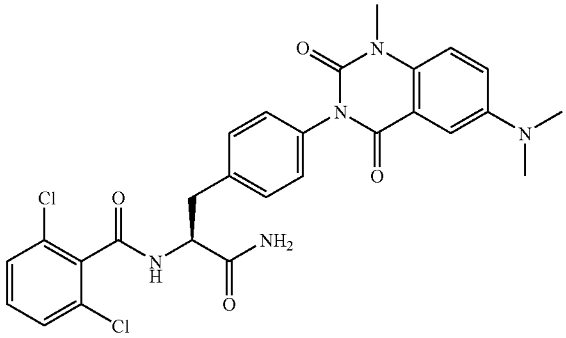
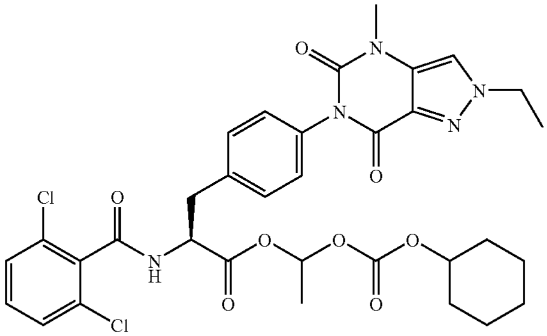
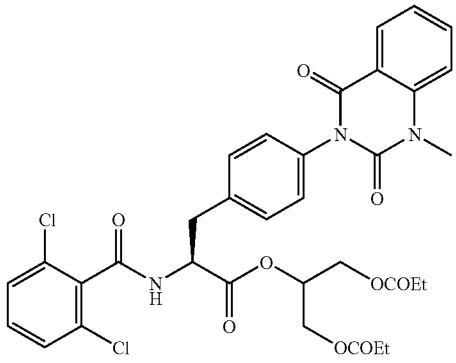
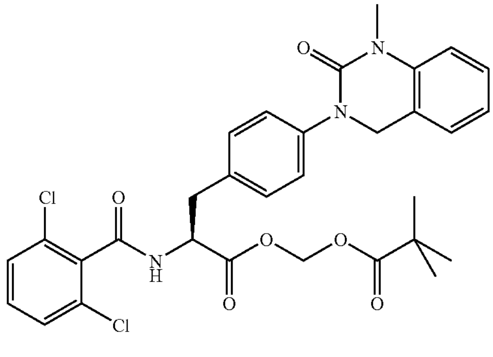

-continued
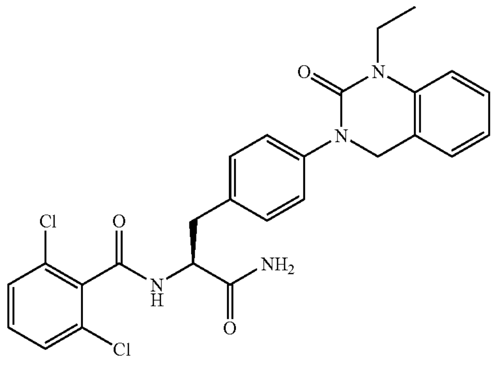
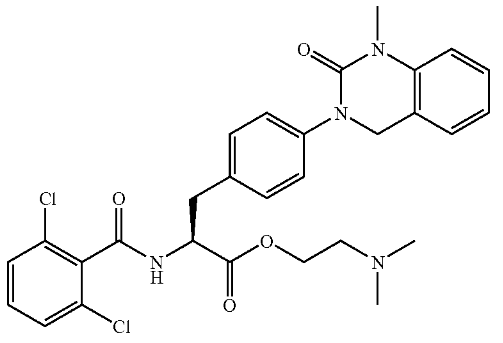
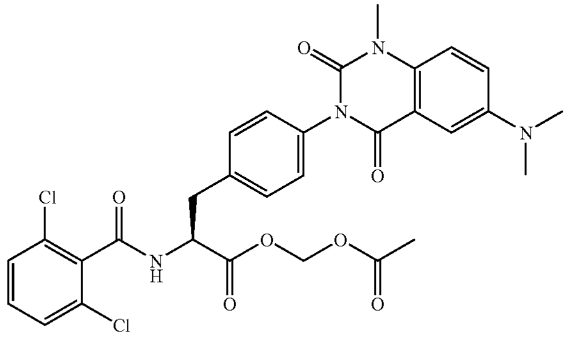
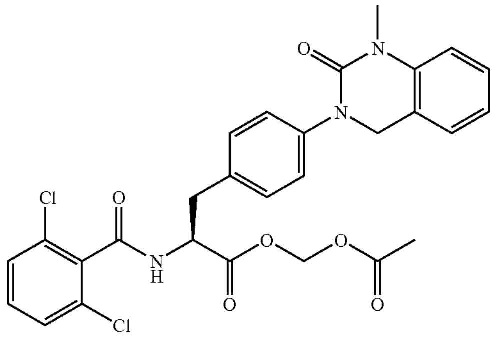
-continued
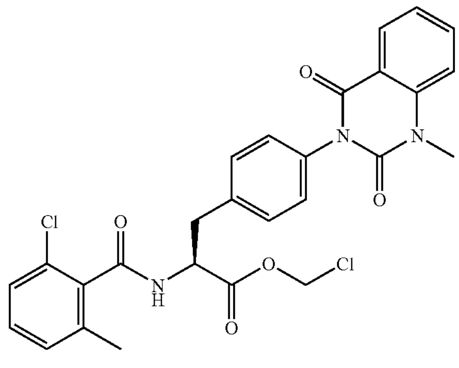
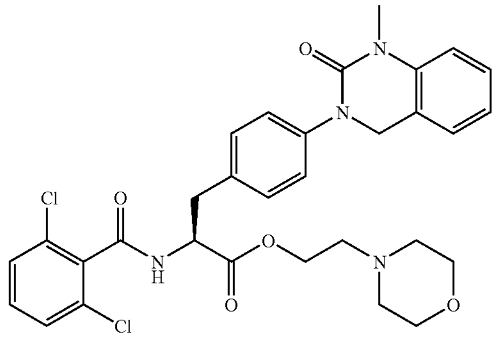
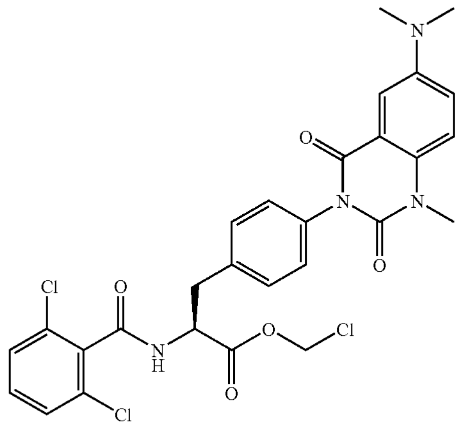
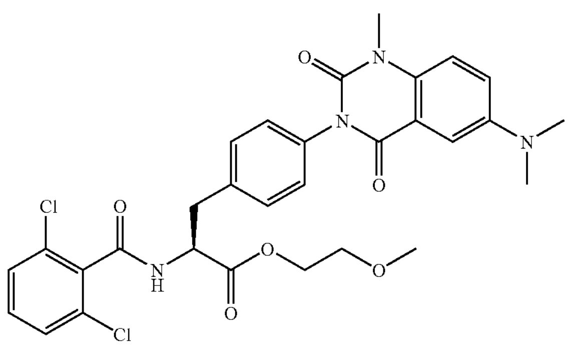

-continued

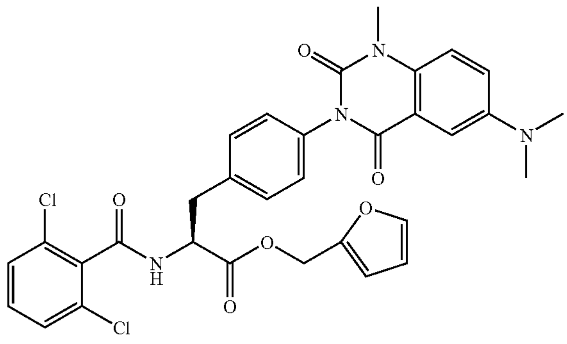

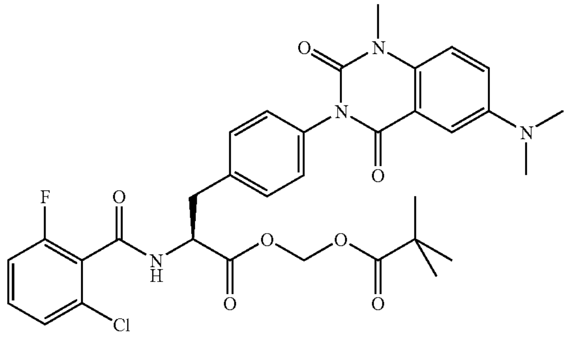

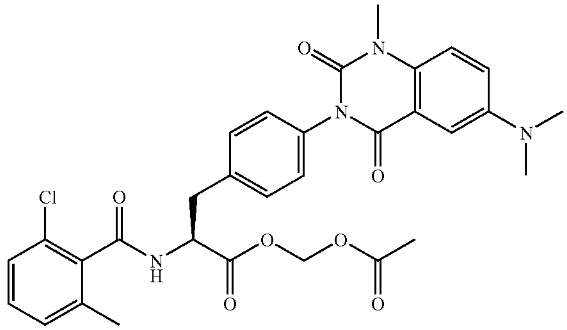

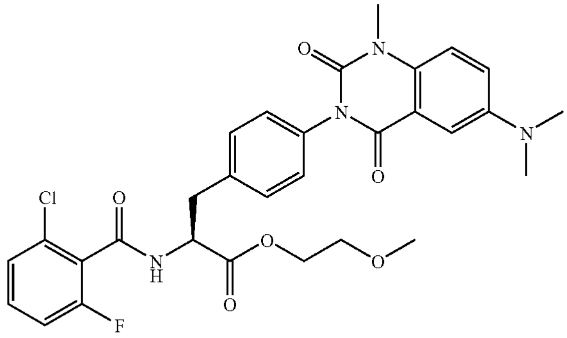

The phenylalanine derivatives (1) of the present invention can be synthesized by, for example, the following methods:

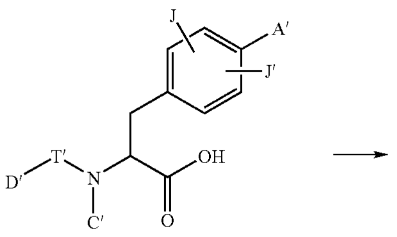

(1)

In the carboxylic acids (X-1), A', C', T' and D' are groups having the structures of A, C, T and D in formula (1), respectively, or groups convertible into them. The carboxyl group in formula (X-1) can be converted into —CO—B group by the known esterification, amidation or thioesterification reaction. Concretely, the reaction can be conducted by methods described below. The compound is treated with a suitable alcohol in the presence of an acid catalyst under dehydration conditions. The compound is treated with an O-alkylating agent such as an alkyl halide in the presence of, if necessary, a base or an acid. For example, the compound is converted into an acid halide with thionyl chloride or the like and then, the obtained compound is treated with a suitable alcohol, amine or thiol, if necessary in the presence of a base. In another example, the compound is treated with ethyl chloroformate under basic conditions to convert it into a corresponding acid anhydride, which is then treated with a suitable alcohol, amine or thiol in, if necessary the presence of a base. In still another example, the compound is treated with a suitable alcohol, amine or thiol in the presence of a condensing agent such as dicyclocarbodiimide and, if necessary, a catalyst such as dimethylaminopyridine.

Thereafter, A', C', T' and D' in the obtained compound is converted to obtain the compound (1) of the present invention.

An example of the methods for synthesizing the carboxylic acids (X-1) used as the starting material in the synthesizing methods described above is as follows:

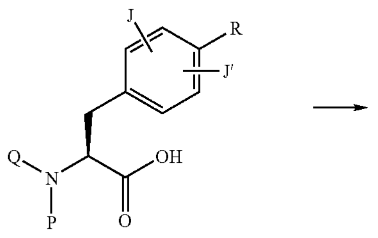

(4)

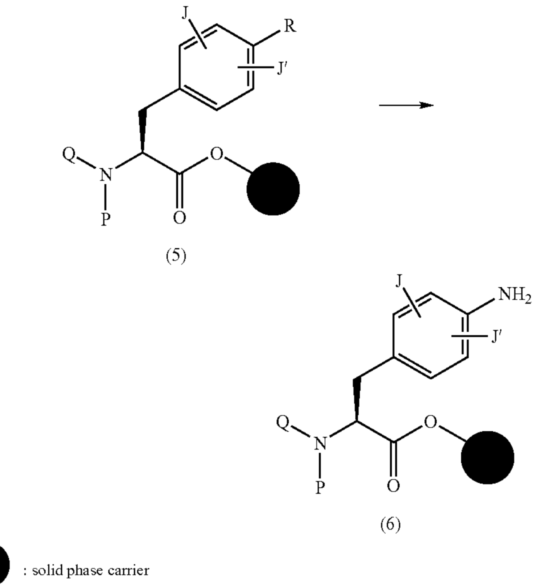

(5)

(6)

: solid phase carrier

A suitably protected carboxylic acid (4) is loaded into a resin by a usual method. The substituent P of the carboxylic acid (4) has a structure of C as described above with reference to the general formula (1), it is a substituent which can be converted into C in any stage of the synthesis or it is suitably protected form of these substituents. The substituent Q of the carboxylic acid (4) has a structure of D-T as described above with reference to the general formula (1), it is a substituent which can be converted into D-T in any stage of the synthesis or it is suitably protected form of these substituents. Further, the substituent R of the carboxylic acid (4) has a structure of a substituent which can be converted into $NH_2$ or suitably protected form of group of $NH_2$.

As for the loading reaction conditions, the reaction can be conducted by using, if necessary, a suitable additive such as HOAt (1-hydroxy-7-azabenzotriazole), HOBt (1-hydroxybenzotriazole) or DMAP (dimethylaminopyridine) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of pyridine and 2,6-dichlorobenzoyl chloride in DMF to obtain an ester (5). The ester (5) can be changed to an amine (6) under suitable conditions depending on the substituent R. For example, when nitro group is used as R, the ester (5) can be changed to the amine (6) in the presence of a reducing agent such as $SnCl_2$ or hydrates thereof in a solvent such as NMP, DMF or ethanol. In the case of an amine protected with Fmoc group (9-fluorenylmethoxycarbonyl group) (FmocNH), the protective group can be removed with a base such as piperidine in a solvent such as DMF to obtain the amine (6).

A quinazolinedione (9) which is an intermediate of a compound of the general formula (X-1) wherein A' represents the general formula (2) and U and V are both C(═O) can be obtained by the following method. First, an urea (7) is obtained by reacting the amine (6) with an isocyanate having a carboxylate ester group in the ortho position. Then, a quinazolinedione (8) can be obtained by a ring closure reaction with a base such as a piperidine or TMG (tetramethylguanidine) in a solvent such as DMF. Further, reagents such as alkyl halide and aryl halide are reacted thereto to obtain the quinazolinedione (9), or the said compound can also be obtained by Mitsunobu reaction using alcohol.

(6)

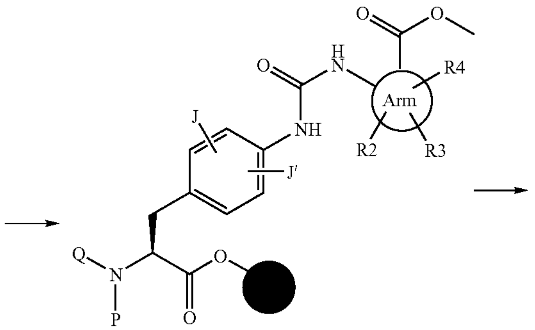

(7)

-continued

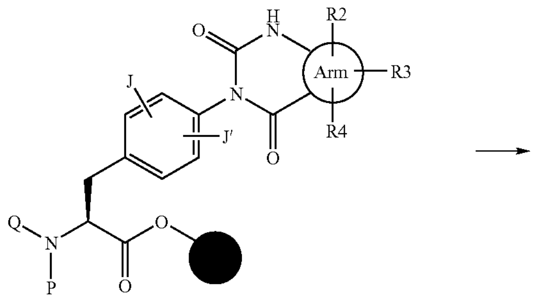

(8)

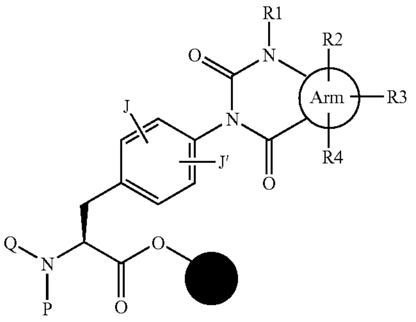

(9)

A quinazolinedione (9) which is an intermediate of a compound of the general formula (X-1) wherein A' represents the general formula (2) and U and V are both C(═O) can also be synthesized by the following method. First, an amide (10) can be obtained by reacting the amine (6) with an acylchloride having nitro group in the ortho position under the existence of 2,6-lutidine base in a solvent such as NMP, or by reacting it with a carboxylic acid having nitro group in the ortho position activated by using a condensing agent such as DIC and, if necessary, a suitable additive such as HOAt or HOBt in an organic solvent such as DMF, NMP or dichloromethane. Then, an amine (11) is obtained by reducing the nitro group with $SnCl_2$ or hydrates thereof and cyclized by reagents such as CDI (carbonyldiimidazole), triphosgene or p-nitrophenylchloroformate to obtain the quinazolinedione (8).

As other synthesizing methods, the quinazolinedione (8) can also be obtained by the following method. First, an amide (11) can be obtained by reacting the amine (6) with a carboxylic acid having a amino group in the ortho position activated by using a condensing agent such as DIC and, if necessary, a suitable additive such as HOAt or HOBt in an organic solvent such as DMF, NMP or dichloromethane. Then, an amide (11) is cyclized by reagents such as CDI, triphosgene or p-nitrophenylchloroformate to obtain the quinazolinedione (8). This method applies to one of the synthesizing methods in case that A' represents the general formula (3-1) and U and V are both C(═O) in the general formula (X-1) of the intermediate, when a variety of salicylic acids is used instead of the above carboxylic acid and the resulting amide (11) is cyclized by reagents such as CDI, triphosgene or p-nitrophenylchloroformate after adding a base such as ethanolamine.

(6)

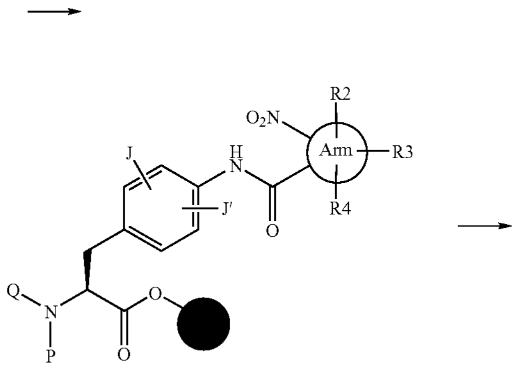

(10)

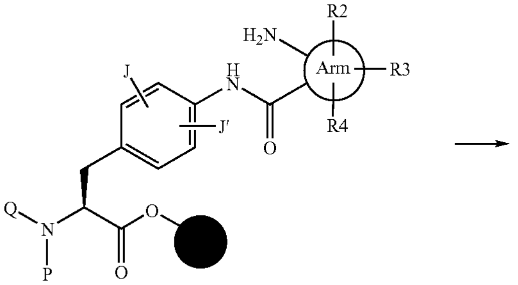

(8)

(11)

A quinazolinedione (9) which is an intermediate of a compound of the general formula (X-1) wherein A' represents the general formula (2), U and V are both C(=O) and R2, R3 or R4 is an electron withdrawing substituent such as nitro group can also be synthesized by the following method. First, an amide (42) can be obtained by reacting the amine (6) with a carboxylic acid having a fluoro group in the ortho position activated by using a condensing agent such as DIC and, if necessary, a suitable additive such as HOAt or HOBt in an organic solvent such as DMF, NMP or dichloromethane. Then, after an amine (43) is obtained by substituting a fluoro group with an amine, the amine (43) is cyclized by reagents such as CDI, triphosgene or p-nitrophenylchloroformate to obtain the quinazolinedione (9).

(6)

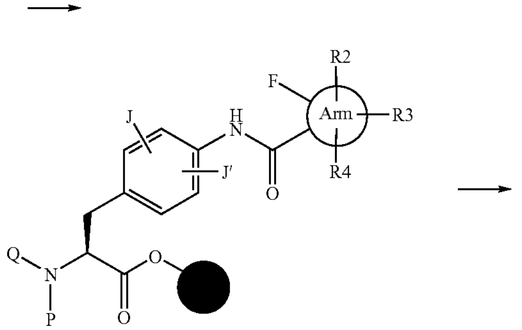

(42)

-continued

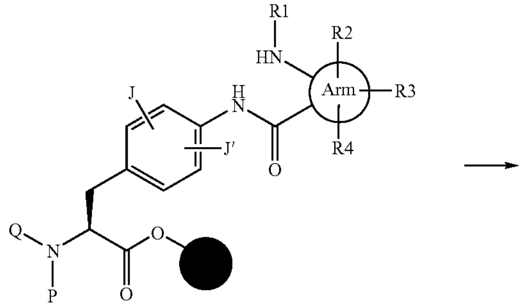

(9)

(43)

In an example of the methods for synthesizing an ester (12) which is an intermediate of a compound of the general formula (X-1) wherein A' represents the general formula (2), U is C(=S) and V is C(=O) can be obtained by reacting the amine (6) with an isothiocyanate having a carboxylate group in the ortho position in a solvent such as NMP.

(8)

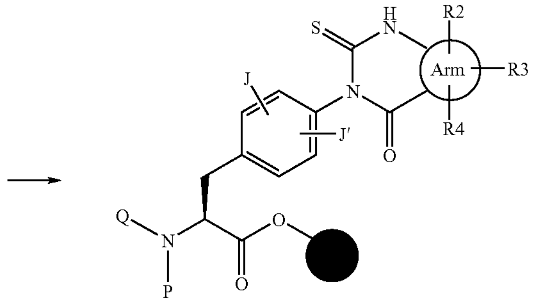

(12)

In an example of the methods for synthesizing an ester (44) which is an intermediate of a compound of the general formula (X-1) wherein A' represents the general formula (2), U is C(=S) and V is C(=O), the said ester can be obtained by reacting the amine (43) with a thiocarbonyldiimidazole in a solvent such as decahydronaphthalene or toluene.

(43)

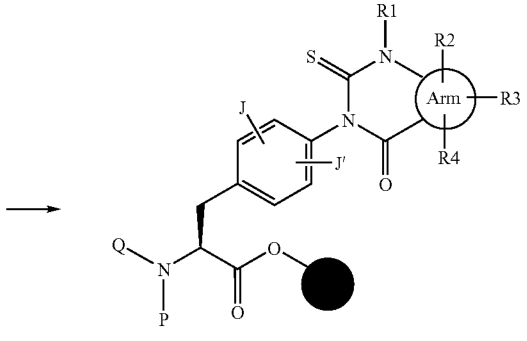

(44)

Among esters (13) which are intermediates of compounds of the general formula (X-1) wherein A' represents the general formula (3) and W is C(—R7), particularly those wherein R7 is a lower alkylthio group, a lower alkylthio group substituted with a cycloalkyl group which may contain a hetero atom(s) in the ring thereof, a lower alkylthio group substituted with an aryl group or a lower alkylthio group substituted with a heteroaryl group can be obtained by reacting the ester (12) with reagents such as alkyl halide and aryl halide.

(12)

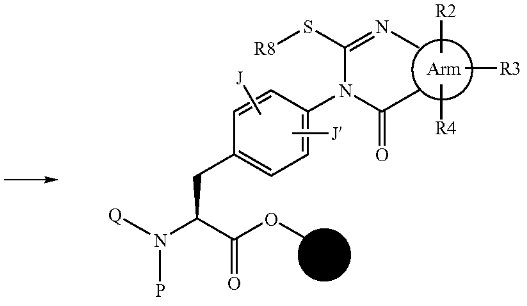

(13)

Further, among esters (14) which are intermediates of compounds of the general formula (X-1) wherein A' represents the general formula (3) and W is C(—R7), particularly those wherein R7 is a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group can be obtained by reacting the amine (11) with various orthoformates or equivalents thereof. The said ester can also be obtained by the oxidation after the reaction with aldehyde or acetal.

(11)

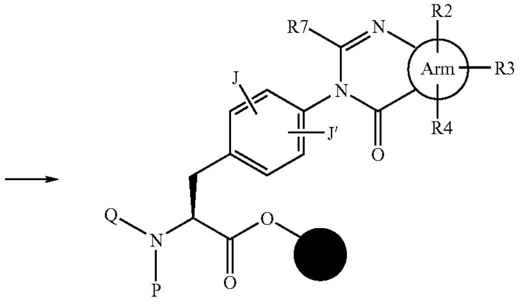

(14)

Among esters (14) which are intermediates of compounds of the general formula (X-1) wherein A' represents the general formula (3) and W is C(—R7), particularly those wherein R7 is a substituted amino group can be synthesized as follows.

First, Y in an ester (15) is a group such as an azide group or amino group and each can be changed to an iminophosphine (16) by reacting with triphenylphosphine or with triphenylphosphine under the existence of diisopropylazodicarboxylic acid respectively. Then, carbodiimide (17) (n is 0 to 4.) is obtained by Aza-Wittig reaction of the iminophosphine (16) with an isocyanate having a carboxylate group in the ortho position. After the nucleophilic attack to the carbodiimide of the amine and the ring closure thereafter, the ester (18) can be synthesized.

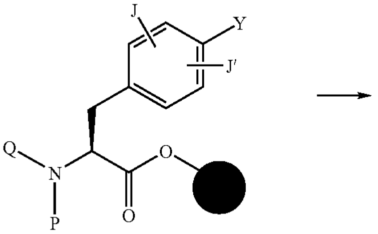

(15)

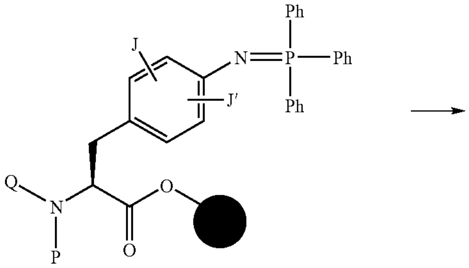

(16)

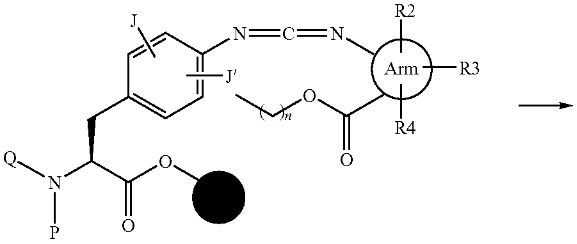

(17)

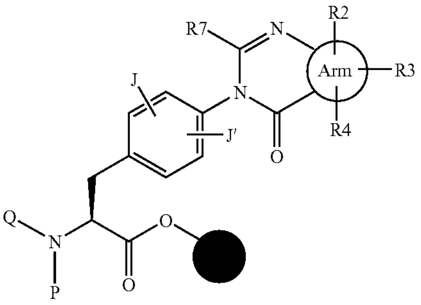

(18)

In an example of the methods for synthesizing an ester (45) which is an intermediate of a compound of the general formula (X-1) wherein A' represents the general formula (3), W is N and X is C(=O), the said ester can be obtained by reacting the amine (11) with sodium nitrite in a solvent such as acetic acid.

(11)

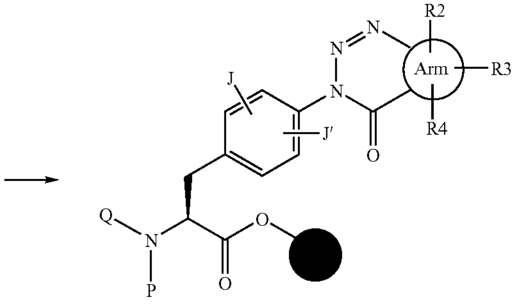

(45)

In an example of the methods for synthesizing an ester (46) which is an intermediate of a compound of the general formula (X-1) wherein A' represents the general formula (2), U is S(=O) and V is C(=O), the said ester can be obtained by reacting the amine (43) with, for example, thionyl chloride in a solvent such as dichloromethane.

(43)

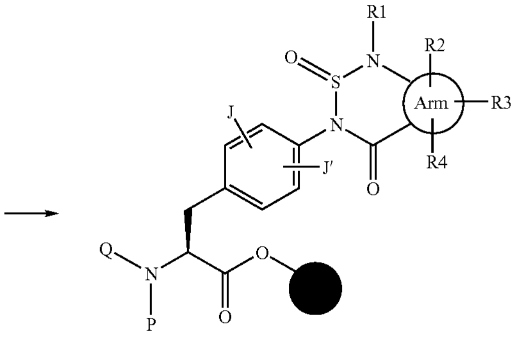

(46)

In an example of the methods for synthesizing an ester (50) of the general formula (X-1) wherein A' represents the general formula (2), U is C(=O) and V is $S(=O)_2$, the said ester can be obtained by the following method. First, a sulfonamide (47) can be obtained by reacting the amine (6) with a sulfonyl chloride having nitro group in the ortho position under the existence of a base such as 2,6-lutidine in a solvent such as NMP and dichloromethane. Then, an amine (48) is obtained by reducing nitro group with $SnCl_2$ or hydrates thereof and cyclized by reagents such as CDI, triphosgene or p-nitrophenylchloroformate to obtain (49). Further, the alkyl halide is reacted thereto to obtain the said ester.

(6)

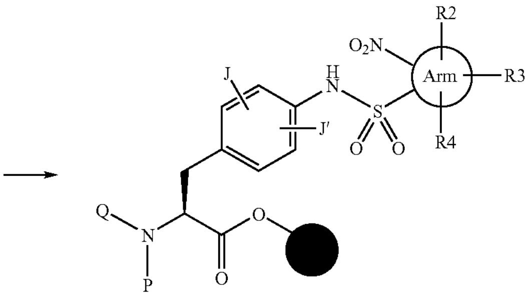

(47)

-continued

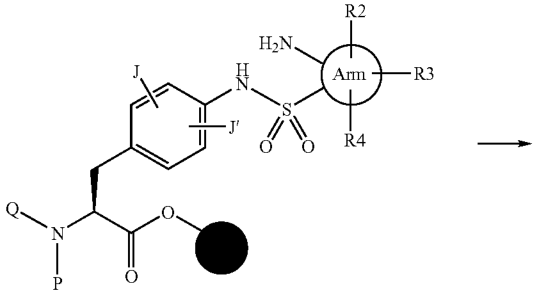

(48)

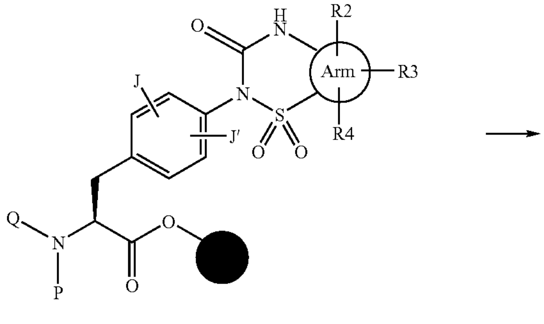

(49)

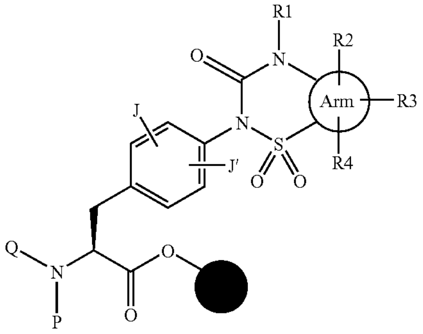

(50)

In an example of the methods for synthesizing an ester (54) which is an intermediate of a compound of the general formula (X-1) wherein A' represents the general formula (2), U and V are both C(=O) and R2, R3 or R4 is an amino group, the said ester can be obtained by the following method. First, an amide (51) is obtained by reacting the amine (6) with a carboxylic acid having nitro group as a substituent(s) and an amino group in the ortho position, activated by using a condensing agent such as DIC and, if necessary, a suitable additive such as HOAt or HOBt in an organic solvent such as DMF, NMP or dichloromethane. Then, (52) is obtained by being cyclized by a reagent such as CDI, triphosgene or p-nitrophenylchloroformate. After the reaction with an alkyl halide, the amine (54) can be obtained by reducing the nitro group with $SnCl_2$, a hydrate thereof or the like.

(6)

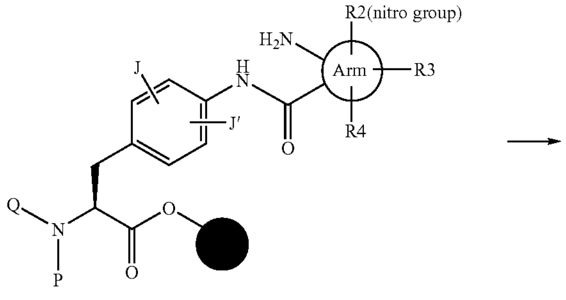

(51)

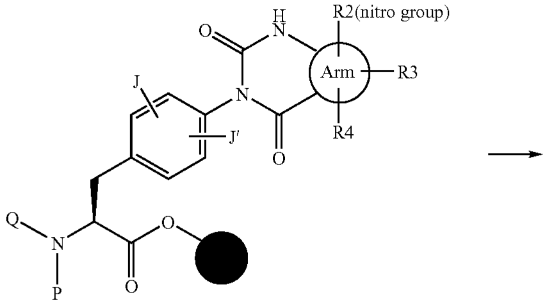

(52)

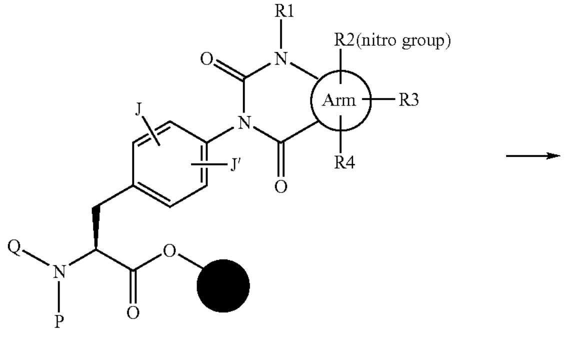

(53)

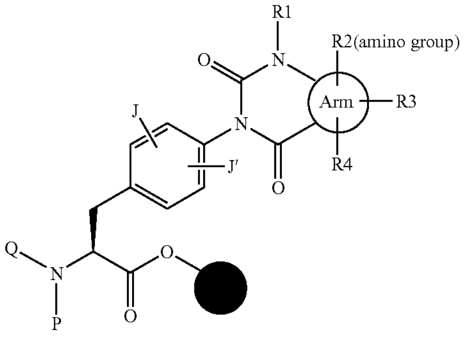

(54)

In an example of the methods for synthesizing an ester (55) which is an intermediate of a compound of the general formula (X-1) wherein A' represents the general formula (2), U and V are both C(═O) and R2, R3 or R4 is an acylamino group, the said ester can be obtained by reacting (54) with an acyl halide under the existence of a base such as pyridine in an organic solvent such as DMF, NMP or dichloromethane.

(54)

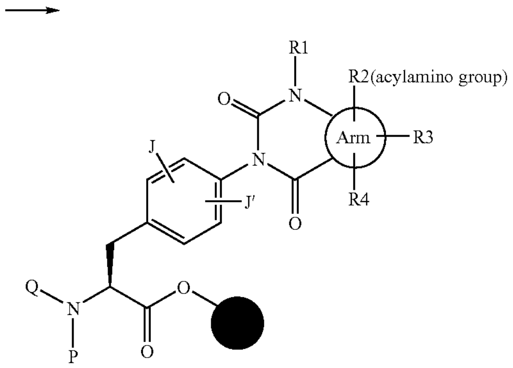

(55)

In an example of the methods for synthesizing an ester (61) which is an intermediate of a compound of the general formula (X-1) wherein A' represents the general formula (2), U and V are both C(═O) and R2, R3 or R4 is a substituted amino group, the said ester can be obtained by the following method. First, an amide (56) is obtained by reacting the amine (6) with a carboxylic acid having a fluoro group as a substituent(s) and nitro group in the ortho position, activated by using a condensing agent such as DIC and, if necessary, a suitable additive such as HOAt or HOBt in an organic solvent such as DMF, NMP or dichloromethane. Then, an amine (57) can be obtained by reacting amide (56) with a substituted amine in a solvent such as NMP and DMSO, and (58) is obtained by reducing the nitro group with $SnCl_2$, a hydrate thereof or the like. After obtaining (60) by cyclizing (58) with a reagent such as CDI, triphosgene or p-nitrophenylchloroformate, (61) can be obtained by Mitsunobu reaction using an alcohol, diisopropylazodicarboxylic acid or the like.

(6)

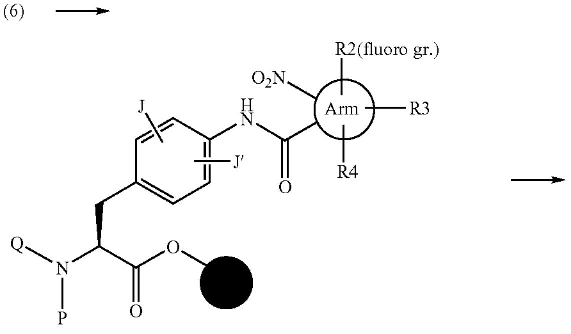

(56)

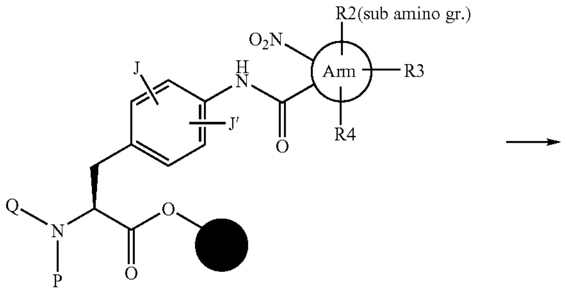

(57)

-continued

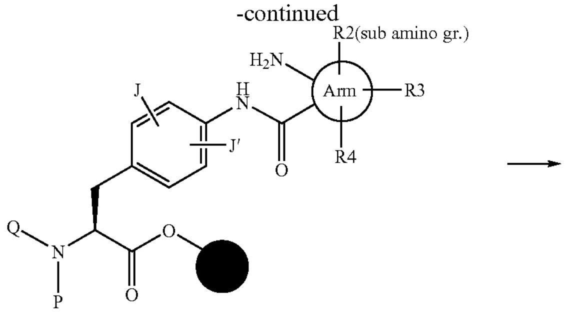

(58)

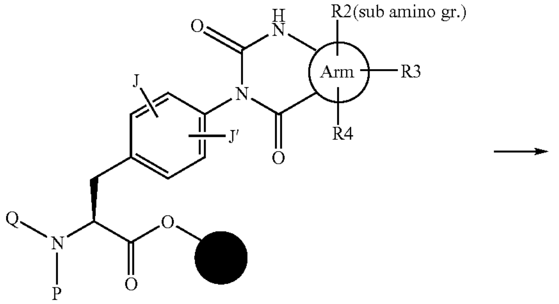

(60)

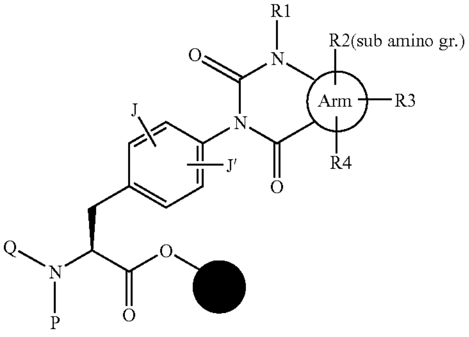

(61)

In an example of the methods for synthesizing an ester (62) which is an intermediate of a compound of the general formula (X-1) wherein A' represents the general formula (2), U and V are both C(=O) and R2, R3 or R4 is an ammonium group, the said ester can be obtained by reacting (61) with an alkyl halide under the existence of a base such as diisopropylethylamine in an organic solvent such as DMF or NMP.

(61)

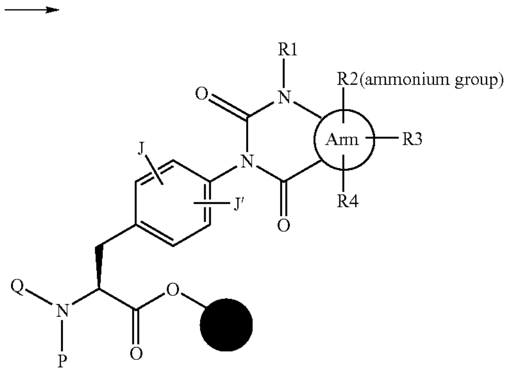

(62)

In an example of the methods for synthesizing an ester (68) which is an intermediate of a compound of the general formula (X-1) wherein A' represents the general formula (3-2), the said ester can be obtained by the following method. First, an amide (63) is obtained by reacting the amine (6) with a carboxylic acid having an amino group protected with Fmoc in β-position activated by using a condensing agent such as DIC and, if necessary, a suitable additive such as HOAt or HOBt in an organic solvent such as DMF, NMP or dichloromethane. Then, an amine (64) is obtained by removing Fmoc and then a sulfonamide (65) is obtained by reacting (64) with sulfonyl chloride having nitro group as a substituent(s) under the existence of a base such as 2,6-lutidine in a solvent such as NMP or dichloromethane. Further, (66) is obtained by reacting (65) with an alkyl halide under the existence of a base such as diisopropylethylamine, and then an amine (67) is obtained by reacting (66) with mercaptoethanol, diazabicycloundecene or the like. The compound is cyclized by reagents such as CDI, triphosgene and p-nitrophenyl chloroformate to obtain the ester (68).

(6)

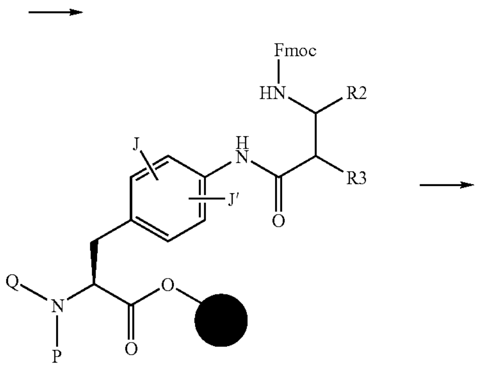

(63)

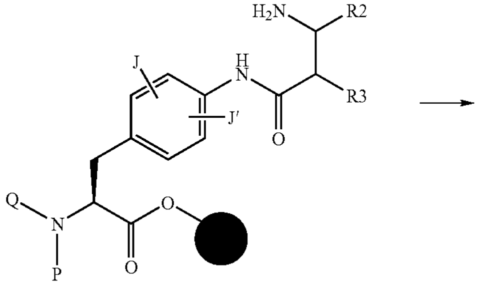

(64)

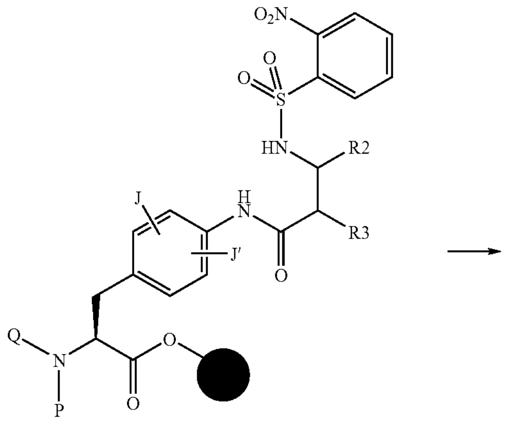

(65)

-continued

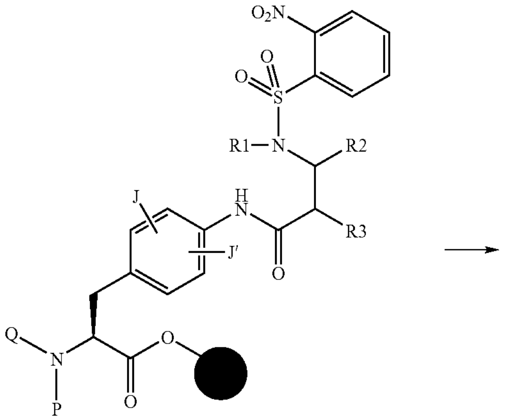

(66)

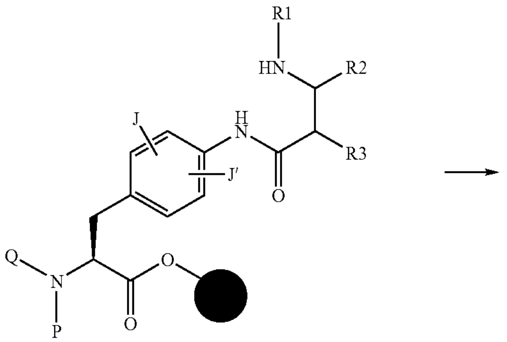

(67)

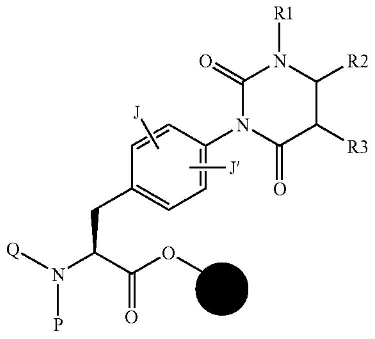

(68)

An ester (72), which is an intermediate of a compound of the general formula (X-1) wherein A' represents the general formula (3-3) and Arm is a benzene ring, can be synthesized in accordance with the following method. The same method can be applied when Arm is other than the benzene ring.

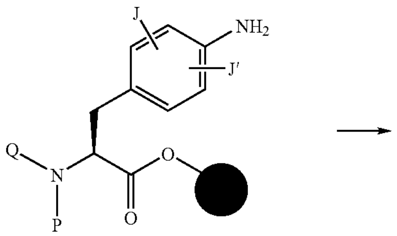

(6)

-continued

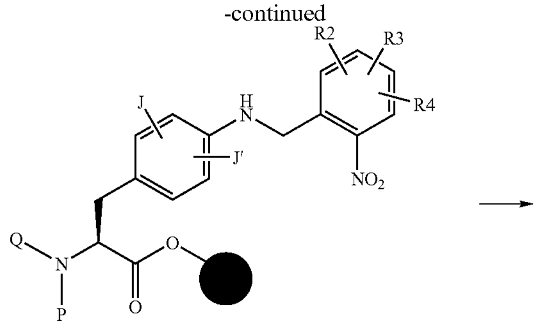

(69)

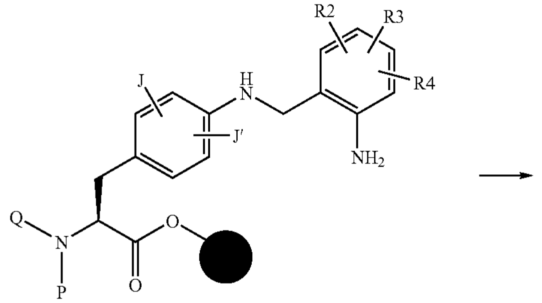

(70)

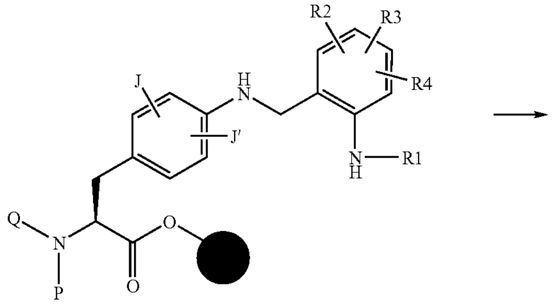

(71)

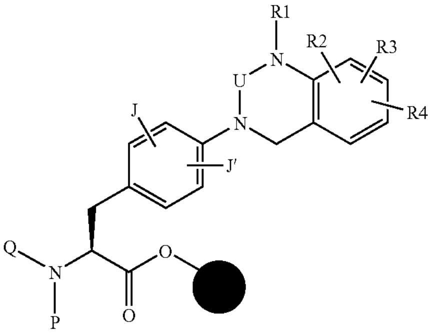

(72)

First, an amine (6) is reacted with a halogenated methylbenzene having nitro group in the ortho position under the existence of N,N-diisopropylethylamine in a solvent such as NMP to obtain a benzylamine (69). After the said benzylamine is reduced by tin chloride or the like to obtain an amine (70), an amine (71) can be obtained by converting the amine on the benzene ring of the introduced benzyl part into mono R1 substituted group by various methods. An ester (72) can be obtained by being finally cyclized by reagents such as CDI, triphosgene and p-nitrophenylchloroformate.

D'-T' part in the general formula (X-1) can be constructed as follows. For example, when T' is C(═O) in the formula (X-1), if, in the ester (19), the substituent G has C structure, the substituent(s) which can be converted into C in a certain point of the synthesizing process or the substituent(s) which have suitably protected structure, then the substituent Z has the structure of (2), (3), (3-1), (3-2) or the substituent(s) which can be converted into A in a certain point of the synthesizing process or the substituent(s) has suitably protected structure, the ester (19) can be converted in the amine (20) by removing a protective group(s) under suitable conditions depending on the protective group E. For instance, when Fmoc group (9-fluorenylmethoxycarbonyl group) is used as E, the protective groups can be removed with a base such as piperidine in a solvent such as DMF. The amine (20) can be converted into the amide (21) by condensing a suitable carboxylic acid by using a condensing agent such as DIC and, if necessary, a suitable additive such as HOAt or HOBt in an organic solvent such as DMF, NMP and dichloromethane.

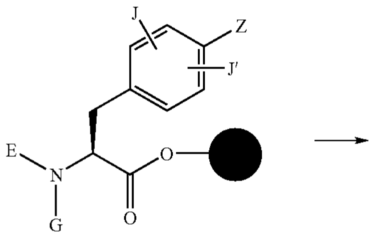

(19)

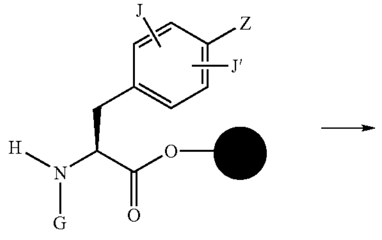

(20)

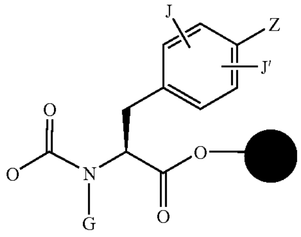

(21)

Further, the amine (20) is reacted with acyl halide, carboxylic anhydride, sulfonyl halide or sulfonyl anhydride under the existence of an organic base such as triethylamine, diisopropylethylamine, pyridine or N,N-dimethylaminopyridine or an inorganic base such as potassium carbonate or sodium carbonate in an organic solvent such as DMF, NMP or dichloromethane to form the corresponding amide structure or sulfonamide structure.

Further, the amine (20) is reacted with one of various isocyanates and isothiocyanates under the existence of, if necessary, an organic base such as triethylamine, diisopropylethylamine, pyridine or N,N-dimethylaminopyridine in an organic solvent such as DMF, toluene or dichloromethane and then can form the corresponding urea structure and thiourea structure.

The esters synthesized by the above-described methods such as (9), (12), (13), (14), (18), (21), (44), (45), (46), (50), (54), (55), (61), (62), (68) and (72) are cleaved from a resin under suitable conditions to obtain a carboxylic acid (X-1). For example, when Wang resin is used, if, in the ester (22), A1, C1 and D1 are A', C' and D' respectively or groups which are converted in A', C', and D' respectively under the cleavage condition, the ester (22) is treated with an acidic solution including TFA (trifluoroacetic acid) or the like to obtain a solution of the carboxylic acid (X-1). Further, the pure carboxylic acid (X-1) can be obtained by well-known isolating and purification methods such as concentration, extraction, crystallization, column chromatography, HPLC and recrystallization of the thus-obtained carboxylic acid (x-1).

The carboxylic acid (X-1) can be synthesized by applying solid phase methods shown above to solution phase methods, by selecting a suitable protective group and using well-known isolating and purification methods.

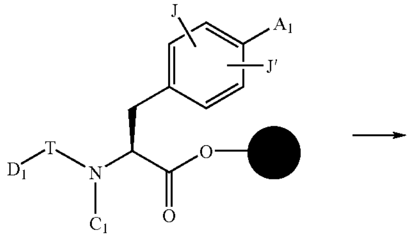

(X-1)

(22)

When the compounds of general formula (1) of the present invention can form salts thereof, the salts must be pharmaceutically acceptable ones. When the compounds have an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compounds have a basic group, the salts can be those with inorganic acids, e.g. hydrochloric acid, sulfuric acid and phosphoric acid; those with organic acids, e.g. acetic acid, citric acid, benzoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersant or by the cation exchange or anion exchange reaction with another salt.

The compounds of the general formula (1) of the present invention include also solvates thereof such as hydrates and alcohol adducts thereof.

The compounds of general formula (1) and salts thereof are administered as they are or in the form of various pharmaceutical compositions to patients. The dosage forms of the pharmaceutical compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylalanine derivative, the active ingredient of the present invention, with any of known adjuncts such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; flavors, e.g. peppermint and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, invert sugars, glucose and vegetable oils.

The group represented by —CO—B in the compounds (1) of the present invention is carboxyl group chemically modified to form a prodrug which can be converted into carboxyl group in vivo as described, for example, in Prog. Med. 5: 2157-2161 (1985), "*Iyakuhin no Kaihatsu*" (Development of Medicines) (published by Hirokawa Book Publishing Store in 1990), Vol. 7, *Bunshi Sekkei*, pages 163 to 198 or *Saishin Souyaku Kagaku* (published by Technomic in 1999), Vol. 2, pages 271 to 298.

The compounds of the general formula (1) wherein B represents hydroxyl group have an excellent α4 integrin-inhibiting activity as will be shown in Referential Test Examples given below.

When the new phenylalanine derivatives of the present invention are applied to the living body, they can exhibit the excellent α4 integrin-inhibiting activity.

Thus, the antagonist containing a compound(s) of above general formula (1) or a salt(s) thereof as active ingredient is usable as a therapeutic agent or preventing agent for diseases in which α4 integrin-depending adhesion process participates in the pathology, such as inflammatory diseases, rheumatoid arthritis, inflammatory bowel diseases, systemic lupus erythematodes, multiple sclerosis, Sjögren's syndrome, asthma, psoriasis, allergy, diabetes, cardiovascular diseases, arterial sclerosis, restenosis, tumor proliferation, tumor metastasis, transplantation rejection, etc. The above-described inflammatory bowel diseases include Crohn's disease and ulcerative colitis.

The dose of the compound of general formula (1) or salt thereof used for the above-described purpose varies depending on the intended therapeutic effect, administration method, period of the treatment, and age and body weight of the patient. The dose is usually 1 μg to 5 g a day for adults in the oral administration, and 0.01 μg to 1 g a day for adults in the parenteral administration.

For this purpose, the compounds of the present invention have high bioavailability and/or blood level when it is administered orally. Therefore, the compounds are usable as oral medicines.

Further, the compounds of the present invention are highly stable in an acidic or alkaline solution and they are useful. They are usable in various dosage forms.

EXAMPLES

The following Examples will further illustrate the present invention, which are only preferred embodiments of the invention and which by no means limit the invention. For reference, processes for producing the starting compounds for the compounds of the present invention will be described below.

Example 1

Synthesis of 1-[[(cyclohexyloxy)carbonyl]oxy]ethyl (2S)-2-[(2,6-dichlorobenzoyl)amino]-3-[4-[6-(dimethylamino)-1-methyl-2,4-dioxo-1,4-tetrahydro-3-(2H)quinazolinyl]phenyl]propionate trifluoroacetate Chloroethyl chloroformate (4 ml) was added to a solution of cyclohexyl alcohol (4.3 ml) and pyridine (3.3 ml) in dichloromethane (60 ml) at −78° C., and they were stirred at room temperature for 15 hours. The reaction mixture was diluted with dichloromethane, washed with saturated aqueous sodium chloride solution and dried over magnesium sulfate. The solvent was evaporated to obtain crude 1-chloroethylcyclohexyl carbonate (7.5 g).

Sodium iodide (1.6 g) and acetonitrile (16 ml) were added to the obtained crude product (7.5 g), and they were stirred at 60° C. for 2 hours. The reaction mixture was diluted with ethyl acetate, washed with water and dried over magnesium sulfate. The solvent was evaporated to obtain a mixture (420 mg) of 1-chloroethylcyclohexyl carbonate and 1-iodoethylcyclohexyl carbonate.

The compound obtained in Referential Example 108 (50 mg), triethylamine (26 ul) and dichloromethane (750 ul) were added to the obtained mixture (54 mg), and they were stirred at room temperature for 16 hours. After the evaporation of the reaction mixture followed by the purification by the reversed-phase high-performance liquid chromatography (reversed-phase HPLC) [water-acetonitrile each containing 0.1% trifluoroacetic acid (TFA)], the title compound (25 mg) was obtained.

MS(ESI MH+): 725

CHNO: C36H38Cl2N4O8

Example 2

Synthesis of [[(2S)-2-[(2,6-dichlorobenzoyl)amino]-3-[4-[6-dimethylamino-1-methyl-2,4-dioxo-1,4-tetrahydro-3-(2H)quinazolinyl]-phenyl]propanoyl]oxy] methyl Pivalate Trifluoroacetate N,N'-Dimethylformamide (10 ml), triethylamine (150 ul) and chloromethyl pivalate (900 ul) were added to the compound obtained in Referential Example 108, and they were stirred at room temperature for 4 days. The reaction mixture was diluted with ethyl acetate, washed with water and dried over magnesium sulfate. The solvent was evaporated to obtain the crude title compound. The crude compound was purified by the reversed-phase high-performance liquid chromatography (reversed-phase HPLC) [water-acetonitrile each containing 0.1% trifluoroacetic acid (TFA)] to obtain the title compound (31 mg).

MS(ESI MH+): 669

CHNO: C33H34Cl2N4O7

NMR data of the compound of Example 2:

$^1$H-NMR (300 MHz, $CDCl_3$) 1.24 (9H, s), 3.13 (6H, s), 3.34 (2H, m), 3.62 (3H, s), 5.33 (1H, m), 5.80 (1H, d, J=5.4 Hz), 5.92 (1H, d, J=5.4 Hz), 6.48 (1H, d, J=8.1 Hz), 7.16-7.42 (8H, m), 7.71 (1H, d, J=8.7 Hz), 7.95 (1H, s).

Example 3

Synthesis of 2-(4-morpholinyl)ethyl (2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate Bistrifluoroacetate Dichloromethane (10 ml), 1-(3-dimethylaminopropyl)-3-ethylcarbodiimide hydrochloride (18 mg), 4-dimethylaminopyridine (11 mg) and N-(2-hydroxyethyl)morpholine (70 ul) were added to the compound (hydrochloride) (50 mg) obtained in Referential Example 108), and they were stirred at room temperature for 4 days. The reaction mixture was concentrated. Ethyl acetate was added to the concentrate. The reaction mixture was washed with saturated aqueous sodium hydrogencarbonate solution and saturated aqueous sodium chloride solution, and then dried over magnesium sulfate. The solvent was evaporated to obtain the crude title compound. The crude compound was purified by the reversed-phase high-performance liquid chromatography (reversed-phase HPLC) [water-acetonitrile each containing 0.1% trifluoroacetic acid (TFA)] to obtain the title compound (11 mg).

MS(ESI MH+): 668.

CHNO: C33H35Cl2N5O6

Example 4

Synthesis of Compound Shown in Table A Given Below

Pyridine (0.05 ml) was added to a mixture of the compound (29.6 mg) obtained in Referential Example 1, $Boc_2O$ (27.5 mg), ammonium hydrogencarbonate (11.6 mg) and 1,4-dioxane (1.5 ml), and they were stirred for one day. Water was added to the reaction mixture, and the crystals thus precipitated were filtered under suction to obtain 18.6 mg (63%) of the intended product.

1H-NMR(300 MHz, DMSO-$d_6$): δ 2.92 (1H, dd, J=14 and 10 Hz), 3.15 (1H, dd, J=10 and 3 Hz), 4.76 (1H, m), 7.18 (2H, d, J=8 Hz), 7.20 (1H, s), 7.40 (8H, m), 7.83 (1H, t, J=8 Hz), 8.05 (1H, d, J=8 Hz), 8.99 (1H, d, J=8 Hz).

MS(ESI MH+): 511

CHNO: C25H20Cl2N4O4

Example 5

Synthesis of Compound Shown in Table A Given Below

The compound (30.0 mg) obtained in Referential Example 1 was dissolved in dichloromethane (2 ml). A solution obtained by diluting thionyl chloride (42.8 μl) with dichloromethane (0.5 ml) was added to the obtained solution. 20 minutes after, one drop of DMF was added to the reaction mixture, and they were further stirred. 10 minutes after, the solvent was evaporated under reduced pressure and the residue was again dissolved in dichloromethane (2 ml). The obtained solution was added dropwise to a solution (147 μl) obtained by dissolving 2M methylamine in tetrahydrofuran and diluting the solution with dichloromethane (2 ml). After stirring for 1 h, the solvent was evaporated, and the residue was purified by the thin-layer silica gel chromatography to obtain 5.0 mg (16%) of the intended product.

1H-NMR(300 MHz, CDCl3): δ 2.76 (3H, d, J=5 Hz), 3.13 (1H, dd, J=14 and 8 Hz), 3.46 (1H, dd, J=14 and 6 Hz), 3.64 (3H, s), 4.93 (1H, td, J=8 and 6 Hz), 5.95 (1H, d, J=5 Hz), 6.53 (1H, d, J=8 Hz), 7.28 (7H, m), 7.46 (2H, d, J=9 Hz), 7.74 (1H, td, J=8 and 1 Hz), 8.23 (1H, dd, J=8 and 1 Hz).

MS(ESI MH+): 525

CHNO: C26H22Cl2N4O4

Example 6

Synthesis of the Compound Shown in Table A Given Below 13.8 mg (44%) of the intended compound was obtained from the compound (30.0 mg) obtained in Referential Example 1 and a 2 M solution (147 μl) of dimethylamine in tetrahydrofuran by the same method as that in Example 5.

1H-NMR(300 MHz, $CDCl_3$): δ 2.57 (3H, s), 2.88 (3H, s), 3.08 (1H, dd, J=13 and 10 Hz), 3.46 (1H, dd, J=13 and 5 Hz), 3.65 (3H, s), 5.39 (1H, ddd, J=10, 8 and 5 Hz), 6.83 (1H, d, J=8 Hz), 7.21 (2H, d, J=9 Hz), 7.28 (5H, m), 7.44 (2H, d, J=9 Hz), 7.74 (1H, td, J=8 and 1 Hz), 8.24 (1H, dd, J=8 and 1 Hz).

MS(ESI MH+): 539

CHNO: C27H24Cl2N4O4

Example 7

Synthesis of the Compound Shown in Table A Given Below

The intended compound was obtained from the compound obtained in Referential Example 1 and 1,3-dipalmitin by the same method as that in Example 3.

1H-NMR(300 MHz, $CDCl_3$): δ 0.95 (6H, t), 1.30 (48H, s), 1.60 (4H, m), 2.35 (4H, m), 3.35 (2H, d), 3.60 (3H, s), 4.15 (2H, m), 4.35 (2H, m), 5.25-5.40 (2H, m), 6.40 (1H, d), 7.15-7.50 (9H, m), 7.75 (1H, t), 8.25 (1H, d).

Example 8

Synthesis of 1-[[(cyclohexyloxy)carbonyl]oxy]ethyl (2S)-2-[(2,6-dichlorobenzoyl)amino]-3-[4-[1-methyl-2,4-dioxo-1,4-tetrahydro-3-(2H)quinazolinyl] phenyl]Propionate The title compound was obtained from the compound obtained in Referential Example 1 by the same method as that in Example 1.

MS(ESI MH+): 682

Example 9

Synthesis of [[(2S)-2-[(2,6-dichlorobenzoyl)amino]-3-[4-[1-methyl-2,4-dioxo-1,4-tetrahydro-3-(2H) quinazolinyl]phenyl]propanoyl]-oxy]methyl Pivalate The title compound was obtained from the compound obtained in Referential Example 1 by the same method as that in Example 2.

MS(ESI MH+): 626

Example 10

Synthesis of 2-(4-morpholinyl)ethyl(2S)-2-[(2,6-dichlorobenzoyl)amino]-3-[4-(1-methyl-2,4-dioxo-1,4-tetrahydro-3-(2H)quinazolinyl)phenyl]propionate The title compound was obtained from the compound obtained in Referential Example 1 by the same method as that in Example 3.

MS(ESI MH+): 625

Example 11

Synthesis of 2-(dimethylamino)ethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate Bistrifluoroacetate The title compound was obtained from 2-dimethylamino-ethanol by the same method as that in Example 3.

MS(ESI MH+): 626

Example 12

Synthesis of tetrahydrofuran-2-ylmethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroAcetate The title compound was obtained from 2-hydroxymethyltetrahydrofuran by the same method as that in Example 3.

MS(ESI MH+): 639

Example 13

Synthesis of acetoxymethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroacetate The title compound was obtained by using bromomethyl acetate as the alkyl halide and dichloromethane as the solvent by the same method as that in Example 2.

MS(ESI MH+): 627

Example 14

Synthesis of chloromethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate Trifluoroacetate:

The title compound was obtained by using chloroiodomethane as the alkyl halide by the same method as that in Example 2.

MS(ESI MH+): 603

Example 15

Synthesis of 2-methoxyethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroacetate:

The title compound was obtained from 2-methoxyethanol by the same method as that in Example 3.

MS(ESI MH+): 613

Example 16

Synthesis of furan-2-ylmethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroacetate The title compound was obtained by using furfuryl alcohol by the same method as that in Example 3.

MS(ESI MH+): 635

Example 17

Synthesis of 2-(2-oxoimidazolidin-1-yl)ethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroacetate The title compound was obtained from 1-(2-hydroxyethyl)-2-imidazolidinone by the same method as that in Example 3.

MS(ESI MH+): 667

Example 18

Synthesis of 2-(piperidin-1-yl)ethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate bistrifluoroacetate The title compound was obtained from N-(2-hydroxyethyl)piperidine by the same method as that in Example 3.

MS(ESI MH+): 666

Example 19

Synthesis of 2-diethylaminoethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate bistrifluoroacetate The title compound was obtained from diethylaminoethanol by the same method as that in Example 3.

MS(ESI MH+): 654

Example 20

Synthesis of 2-(2-oxo-pyrrolidin-1-yl)ethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroacetate The title compound was obtained from 1-(2-hydroxyethyl)-2-pyrrolidone by the same method as that in Example 3.

MS(ESI MH+): 666

Example 21

Synthesis of dimethylcarbamoylmethyl(2S)-2-[(2,6-dichlorobenzoyl)amino]-3-[4-(6-dimethylamino-1-methyl-2,4-dioxo-1,4-tetrahydro-3-(2H)quinazolinyl)phenyl]propionate trifluoroacetate The title compound was obtained from N,N-dimethylchloroacetamide by the same method as that in Example 2.

MS(ESI MH+): 640

Example 22

Synthesis of acetoxymethyl(2S)-2-[(2,6-dichlorobenzoyl)amino]-3-[4-(1-methyl-2-oxo-1,4-tetrahydro-3-(2H)-quinazolinyl)phenyl]propionate A mixture of 30 mg of the compound obtained in Referential Example 147, 18 μl of triethylamine, 19 mg of bromomethyl acetate and 1 ml of dichloromethane was stirred at room temperature overnight. The solvent was evaporated and the obtained product was purified by the reversed-phase high-performance liquid chromatography (reversed-phase HPLC) [water-acetonitrile each containing 0.1% trifluoroacetic acid (TFA)] to obtain the title compound (10 mg).

MS(ESI MH+): 570

Example 23

Synthesis of 2-(4-morpholinyl)ethyl(2S)-2-[(2,6-dichlorobenzoyl)amino]-3-[4-(1-methyl-2-oxo-1,4-tetrahydro-3-(2H)-quinazolinyl)phenyl]propionate Trifluoroacetate The title compound was obtained from the compound obtained in Referential Example 147 by the same method as that in Example 3.

MS(ESI MH+): 611

The structural formulae of the compounds obtained in Examples 1 to 23 are shown in the form of the free compounds in Table A given below.

TABLE A

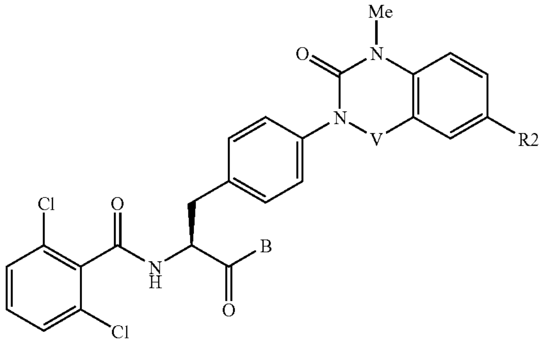

| Example | B | R2 | V |
|---|---|---|---|
| 1 | 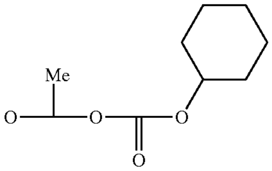 | NMe2 | C═O |
| 2 | 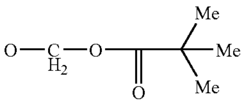 | NMe2 | C═O |
| 3 | 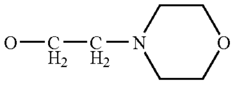 | NMe2 | C═O |
| 4 | $NH_2$ | H | C═O |
| 5 | 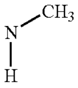 | H | C═O |
| 6 | 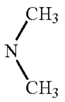 | H | C═O |

TABLE A-continued

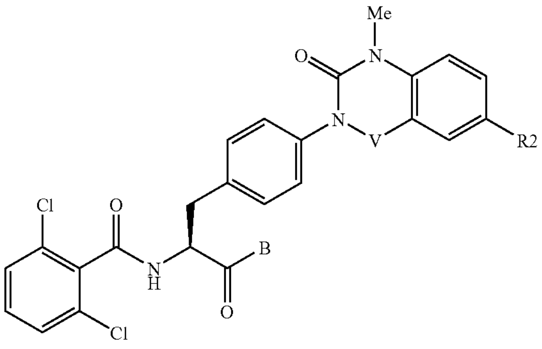

| Example | B | R2 | V |
|---|---|---|---|
| 7 | 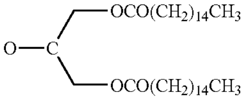 | H | C═O |
| 8 | 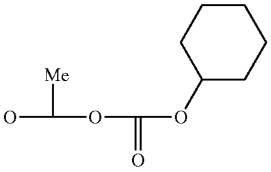 | H | C═O |
| 9 | 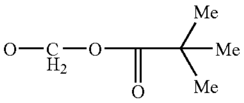 | H | C═O |
| 10 | 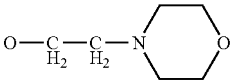 | H | C═O |
| 11 | 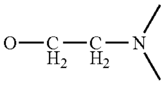 | NMe2 | C═O |
| 12 | 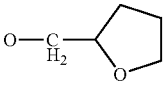 | NMe2 | C═O |
| 13 | 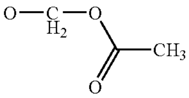 | NMe2 | C═O |
| 14 | 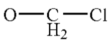 | NMe2 | C═O |
| 15 | 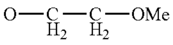 | NMe2 | C═O |
| 16 | 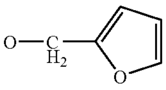 | NMe2 | C═O |
| 17 | 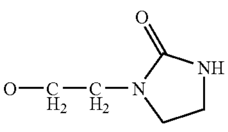 | NMe2 | C═O |

TABLE A-continued
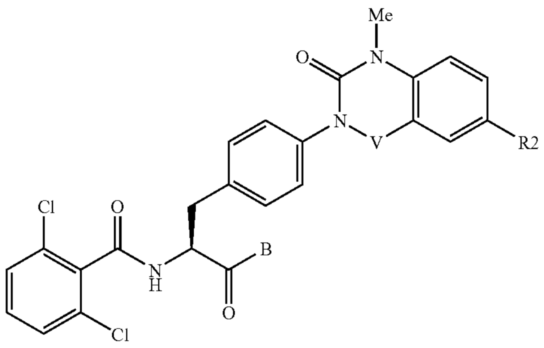
| Example | B | R2 | V |
|---|---|---|---|
| 18 | 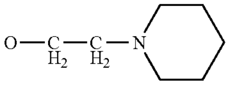 | NMe2 | C=O |
| 19 | 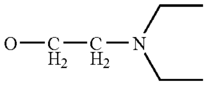 | NMe2 | C=O |
| 20 | 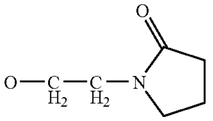 | NMe2 | C=O |
| 21 | 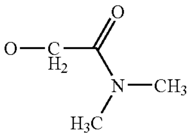 | NMe2 | C=O |
| 22 | 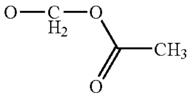 | H | $CH_2$ |
| 23 | 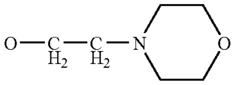 | H | $CH_2$ |
Compounds having the following chemical structures can be easily produced as shown in the above-described Examples or production methods or by slightly modified methods which are self-evident for those skilled in the art.
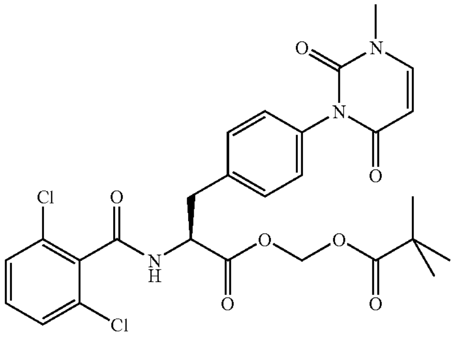
-continued
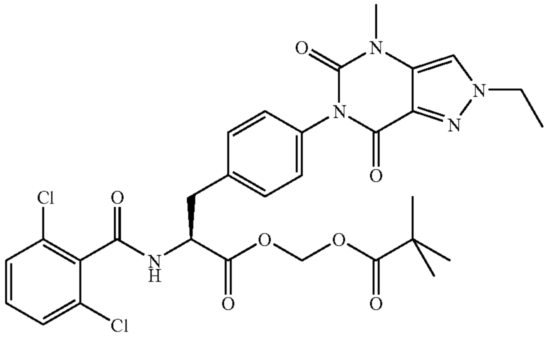
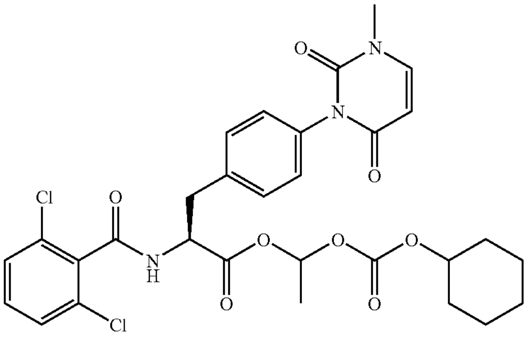
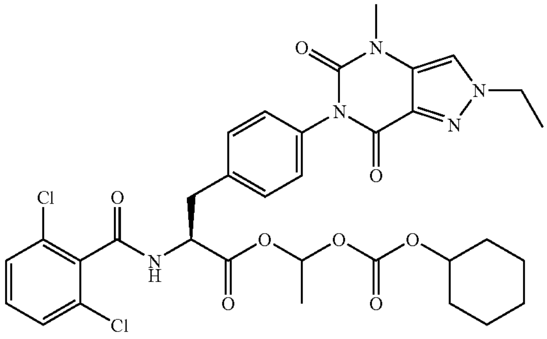
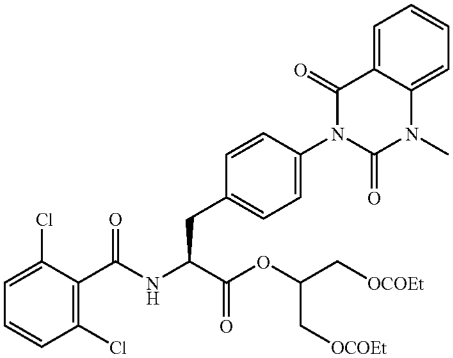

-continued
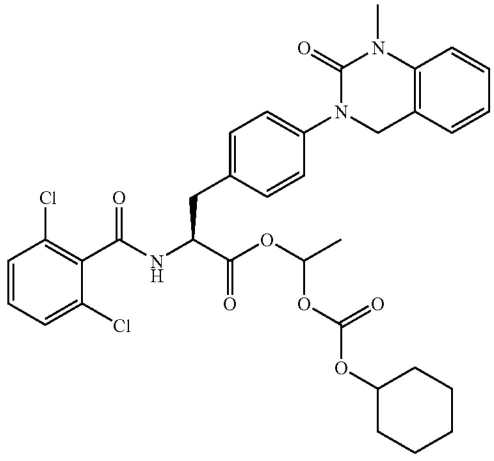
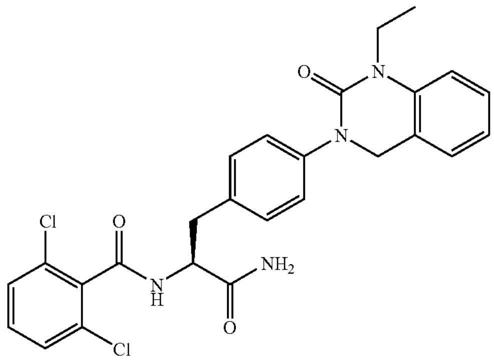
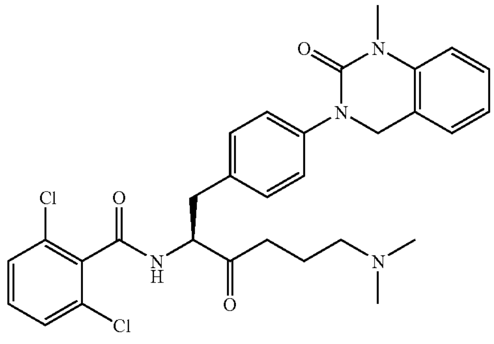
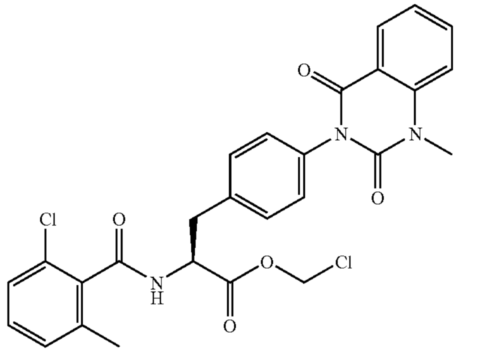
-continued
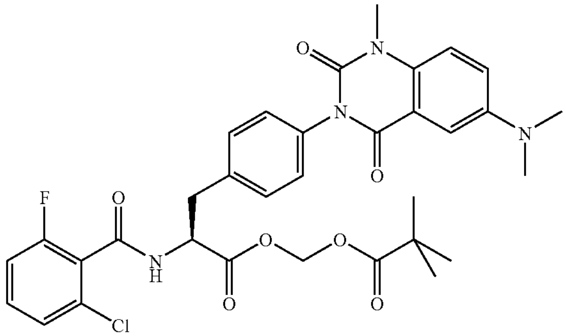
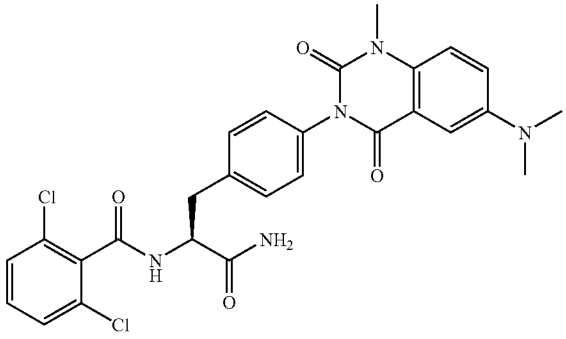
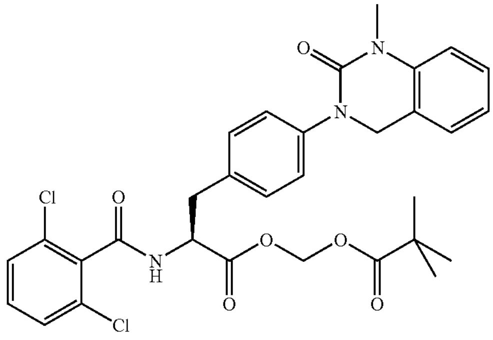
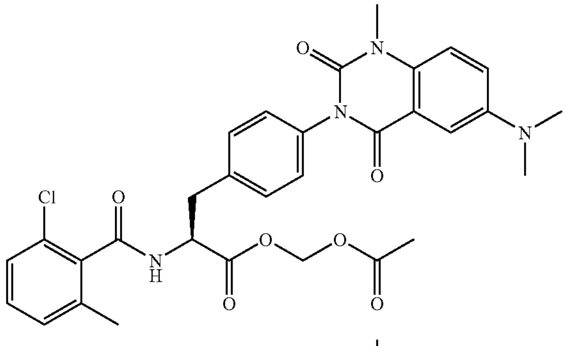
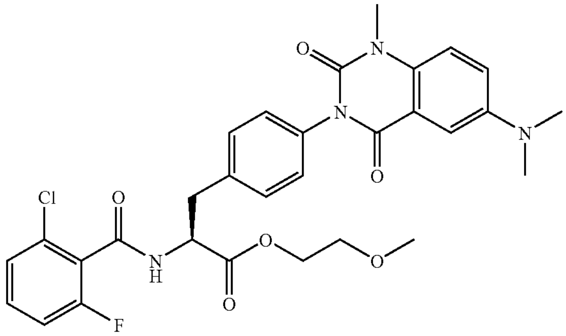

The new phenylalanine derivatives of the present invention are prodrugs which can be converted into carboxyl compounds in vivo. The conversion of those derivatives into the carboxyl compounds can be confirmed by using various metabolic enzyme systems, particularly the liver or small intestine S9 fraction with reference to, for example, a method described in *Yakubutsu Taisha Koso, Seibutsuyaku Kagaku Jikken Koza*, Vol. 15 (published by Hirokawa Book Publishing Store in 2001). The conversion can also be confirmed by administering the compounds of the present invention to animals such as mice and rats (including human beings) and analyzing the medicines in the blood.

Further, when the new phenylalanine derivative of the present invention is administered to a living body, it exhibits an excellent α4 integrin-inhibiting activity. This fact is proved by the fact that the active compound of the general formula (1) wherein B represents hydroxyl group exhibited an excellent α4 integrin-inhibiting activity in the evaluation methods shown in Referential Test Examples 1 and 2. This fact can also be proved by applying the compounds of the present invention to animals such as mice and rats (including human beings) and determining α4 integrin-inhibiting activity in the plasma taken by the animals by the methods shown in Referential Test Examples 1 and 2.

The following Reference Examples will illustrate processes for producing the starting compounds for the compounds of the present invention, which by no means limit the starting materials or the production processes.

Reference Example 1

Synthesis of the Compound of the Following General Formula (23) Which has a Substituent(s) of Reference Example 1 of Table 1

Process 1 Preparation of Resin

Fmoc-Phe(4-nitro)-OH (2.5 g), 2,6-dichlorobenzoyl chloride (0.745 mL) and pyridine (1.5 mL) in a solution of NMP (25 mL) were added to Wang resin (0.76 mmol/g, 2.3 g) and stirred at room temperature for 16 hours. After removing the excess solvent, the resin was washed with DMF three times, dichloromethane three times and NMP twice. In order to conduct capping of an unreacted hydroxyl group on the resin, the resin was treated with acetic anhydride (20 mL), pyridine (20 mL) and NMP (20 mL) for 2 hours. After removing the excess solvent, the resin was washed with DMF three times and dichloromethane three times, and dried under reduced pressure.

Process 2 Removal of Fmoc Group

A DMF solution of 20% piperidine (25 mL) was added to the resin obtained in Process 1 and reacted for 15 minutes. After removing the solvent, the resin was washed with DMF and dichloromethane three times each, and dried under reduced pressure.

Process 3 Acylation Reaction 2,6-dichlorobenzoyl chloride (10.1 mL), 2,6-lutidine (1.6 mL) and NMP (26 mL) were added to 2.0 g of the resin obtained in Process 2 and reacted for 6 hours. After removing the excess solvent, the resin was washed with DMF and dichloromethane three times each, and dried under reduced pressure.

Process 4 Reduction of Nitro Group

NMP (30 mL).EtOH (1.5 mL) solution of $SnCl_2.2H_2O$ (15.0 g) was added to 1.5 g of the resin obtained in Process 3 and reacted for 16 hours. After removing the reaction solvent, the resin was washed with DMF and dichloromethane three times each.

Process 5 Construction of quinazoline-2,4-dione Ring 2 g of the resin obtained in Process 4 was reacted in NMP solution (32 mL) of methyl 2-isocyanatebenzoate (1.92 g) for 16 hours. After removing the reaction solvent, the resin was washed with DMF and dichloromethane three times each. DMF solution of 20% piperidine was added to the resin for 1 hour. After removing the reaction solvent, the resin was washed with DMF and dichloromethane three times each and dried under reduced pressure.

Process 6 Alkylation

Methyl iodide (0.75 mmol), 18-crown-6 (30 mg), NMP (1 mL) and $K2CO_3$ (35 mg) were added to 20 mg of the resin obtained in Process 5 and reacted for 3 days. After removing the reaction solvent, the resin was washed with DMF, water, DMF and dichloromethane three times each and dried under reduced pressure.

Process 7 Cleavage from Resin

The resin obtained in Process 6 was treated with trifluoroacetic acid containing 5% of water for 1 hour. After filtration, the filtrate was concentrated under reduced pressure. The residue was purified with high-pressure liquid chromatography (water/acetonitrile) to obtain 8 mg of the intended compound.

MS(ESI MH+): 512

CHNO: C25H19Cl2N3O5

Reference Examples 2 to 7

The compounds described below were synthesized by the same procedure as that of Reference Example 1 except that corresponding alkylation reagents were used in Process 6 of Reference Example 1. Meanwhile, R in Table 1 is a substituent(s) in the following general formula (23) and the same procedure as that of Reference Example 1 was repeated in Reference Example 2 except that Process 6 of Reference Example 1 was not carried out.

TABLE 1

(23)

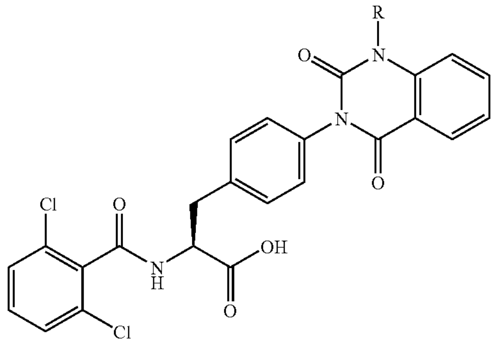

| Ref. Example | R— | MS Found (MH+) |
|---|---|---|
| 1 | Me- | 512 |
| 2 | H— | 498 |
| 3 | Et- | 526 |
| 4 | 2,6-difluorobenzyl | 624 |
| 5 | 4-(1-pyrrolidino)benzenecarbonylmethyl | 685 |
| 6 | NCCH2— | 537 |
| 7 | HOC(═O)CH2— | 556 |

Reference Example 8

Synthesis of the Compound of the Following General Formula (24) which has a Substituent(s) of Reference Example 8 of Table 2

Process 1 Construction of quinazoline-2,4-dione Ring and Removal of Fmoc Group

A nitro group of the resin (1 g) obtained in Process 1 of Reference Example 1 was reduced in accordance with Process 4 of Reference Example 1, and quinazoline-2,4-dione ring was constructed and Fmoc group was removed in accordance with Process 5 of Reference Example 1.

Process 2 Acylation, Alkylation, and Cleavage from Resin

Acylation was conducted by using the resin obtained in Process 1 of Reference Example 8 (25 mg), 2,6-dimethyl benzoic acid (0.4 mmol), DIC (0.4 mmol), HOAt (0.4 mmol) and NMP (2 mL). Then, alkylation was conducted in accordance with Process 6 of Reference Example 1 and cleavage from resin and purification was performed by the same process as Process 7 of Reference Example 1 to obtain the intended compound (9 mg).

MS(ESI MH+) 472

CHNO: C27H25N3O5

Reference Examples 9 to 13

The compounds described below were synthesized by the same procedure as that of Reference Example 8 except that corresponding carboxylic acid was used in Process 2 of Reference Example 8. R in Table 2 is a substituent(s) in the following general formula (24). Further, twice as much as DIC and HOAt used in Process 2 of Reference Example 8 were used in Reference Example 13, to obtain the intended compound (7 mg).

TABLE 2

(24)

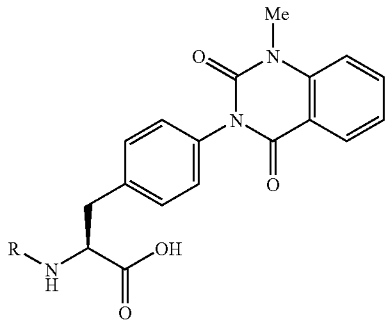

| Ref. Example | R— | MS Found (MH+) |
|---|---|---|
| 8 | 2,6-dimethylbenzoyl | 472 |
| 9 | 2,6-dimethoxybenzoyl | 504 |
| 10 | 2-ethoxybenzoyl | 488 |
| 11 | 3,4-dimethoxycinnamyl | 530 |
| 12 | cyclohexylcarbonyl | 450 |
| 13 | trans-4-carboxycyclohexanecarbonyl | 494 |

Reference Example 14

Synthesis of the Compound of the Following General Formula (25) which has a Substituent(s) of Reference Example 14 of Table 3

Process 1 Construction of quinazoline-2-thioxo-4-one Ring

The resin obtained in Process 4 of Reference Example 1 (2.00 g) was reacted in NMP solution (25 mL) of methyl 2-isothiocyanatebenzoate (1.40 g) for 16 hours. After removing the reaction solvent, the resin was washed with DMF and dichloromethane three times each and dried under reduced pressure.

Process 2 Cleavage from Resin

The resin obtained in Process 1 (25 mg) was treated in accordance with Process 7 of Reference Example 1 to obtain the intended compound (10 mg).

MS(ESI MH+): 513

CHNO: C24H17Cl2N3O4S

Reference Example 15

Synthesis of the Compound of the Following General Formula (25) which has a Substituent(s) of Reference Example 15 of Table 3

Process 1 Acylation

Acylation was conducted by using the resin obtained in Process 2 of Reference Example 1 (25 mg), 2,6-dimethylbenzoic acid (0.4 mmol), DIC (0.4 mmol), HOAt (0.4 mmol) and NMP (2 mL).

Process 2 Construction of quinazoline-2-thioxo-4-one Ring

The resin obtained in Process 1 (2.00 g) was reacted in NMP solution (25 mL) of methyl 2-isothiocyanatebenzoate (1.40 g) for 16 hours. After removing the reaction solvent, the resin was washed with DMF and dichloromethane three times each and dried under reduced pressure.

Process 3 Cleavage from Resin

The resin obtained in Process 1 (25 mg) was treated in accordance with Process 7 of Reference Example 1 to obtain the intended compound (8 mg).

MS(ESI MH+): 474.

CHNO: C26H23N3O4S

TABLE 3

(25)

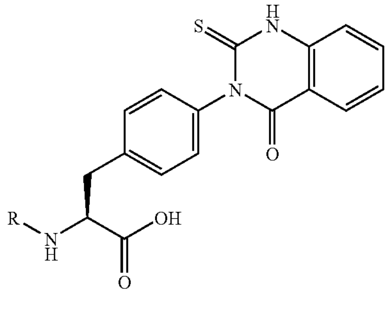

| Ref. Example | R— | MS Found (MH+) |
|---|---|---|
| 14 | 2,6-dichlorobenzoyl | 513 |
| 15 | 2,6-dimethylbenzoyl | 474 |

Reference Example 16

Synthesis of the Compound of the Following General Formula (26) which has a Substituent(s) of Reference Example 16 of Table 4

Process 1 Alkylation

Allylbromide (0.5 mmol), diisopropylethylamine (11.0 mmol) and NMP (2 mL) were added to the resin obtained in Process 1 of Reference Example 14 (25 mg) and reacted for 16 hours. After removing the reaction solvent, the resin was washed with DMF and dichloromethane three times each and dried under reduced pressure.

Process 2 Cleavage from Resin

The resin obtained in Process 1 was treated in accordance with Process 7 of Reference Example 1 to obtain the intended compound (6 mg).

MS(ESI MH+): 554

CHNO: C27H21Cl2N3O4S

Reference Examples 17 to 30

The compounds shown in Table 4 were synthesized by the same procedure as that of Reference Example 16 except that the resin obtained in Process 1 of Reference Example 14 or Process 2 of Reference Example 15 was used and the corresponding halide was used in Process 1 of Reference Example 16. Meanwhile, R1 and R2 in Table 4 are a substituent(s) in the following general formula (26).

TABLE 4

(26)

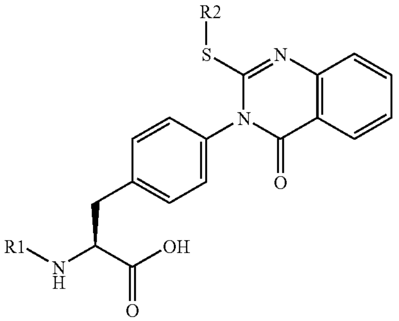

| Ref. Example | R1— | R2— | MS Found (MH+) |
|---|---|---|---|
| 16 | 2,6-dichlorobenzoyl | allyl | 554 |
| 17 | 2,6-dichlorobenzoyl | ethyl | 542 |
| 18 | 2,6-dichlorobenzoyl | methyl | 528 |
| 19 | 2,6-dichlorobenzoyl | isoamyl | 584 |
| 20 | 2,6-dichlorobenzoyl | 2,6-difluorobenzyl | 640 |
| 21 | 2,6-dichlorobenzoyl | 2-methylbenzyl | 618 |
| 22 | 2,6-dichlorobenzoyl | 1-phenylethyl | 618 |
| 23 | 2,6-dichlorobenzoyl | 4-methoxyphenacyl | 662 |
| 24 | 2,6-dimethylbenzoyl | methyl | 488 |
| 25 | 2,6-dimethylbenzoyl | ethyl | 502 |
| 26 | 2,6-dimethylbenzoyl | allyl | 514 |
| 27 | 2,6-dimethylbenzoyl | isoamyl | 544 |
| 28 | 2,6-dimethylbenzoyl | 2,6-difluorobenzyl | 600 |
| 29 | 2,6-dimethylbenzoyl | 2-methylbenzyl | 578 |
| 30 | 2,6-dimethylbenzoyl | 1-phenylethyl | 578 |

NMR data of the compound of Reference Example 18: $^1$H-NMR (CDCl3) δ=2.53 (3H, s), 3.40 (2H, t, J=5.3 Hz), 5.20 (1H, t, J=5.3 Hz), 7.21-7.35 (6H, m), 7.41 (1H, t, J=7.5 Hz), 7.50 (2H, d, J=8.7 Hz), 7.65 (1H, d, J=8.4 Hz), 7.76 (1H, t, J=6.9 Hz), 8.19 (1H, d, J=7.5 Hz)

Reference Example 31

Synthesis of the Compound of the Following General Formula (27) which has a Substituent(s) of Reference Example 31 of Table 5

Process 1 Acylation 2-nitrobenzoylchloride (4 mmol), 2,6-lutidine (8 mmol) and NMP were added to the resin obtained in Process 4 of Reference Example 1 (1.00 g) and stirred for 16 hours. After that, the resin was washed with DMF and dichloromethane three times each and dried under reduced pressure.

Process 2 Reduction of Nitro Group

The resin obtained in Process 1 (25 mg) was treated in accordance with Process 4 of Reference Example 1 to obtain the intended resin.

Process 3 Cyclization by Ortho Ester and Cleavage from Resin

Trimethylorthoacetate (1 mL), AcOH (50 μL) and NMP (1 mL) were added to the resin obtained in Process 2 (25 mg) and stirred at 50° C. for 16 hours. After washing it with DMF and dichloromethane three times each and drying under reduced pressure, the resin was treated in accordance with Process 7 of Reference Example 1 to obtain the intended compound (8 mg).

MS(ESI MH+): 496

CHNO: C25H19Cl2N3O

Reference Examples 32 to 44

The compounds shown in Table 5 were synthesized by the same procedure as that of Reference Example 31 except that the resin obtained in Process 4 of Reference Example 1 or Process 1 of Reference Example 15 was used in Process 1 of Reference Example 31 and the corresponding ortho ester was used in Process 3 of Reference Example 31. Meanwhile, R1 and R2 in Table 5 are a substituent(s) in the following general formula (27).

TABLE 5

(27)

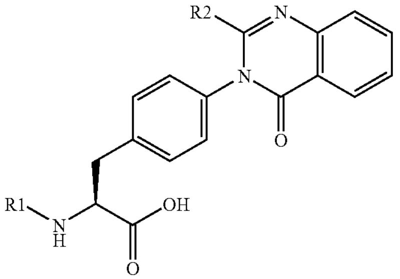

| Ref. Example | R1— | R2— | MS Found (MH+) |
|---|---|---|---|
| 31 | 2,6-dichlorobenzoyl | methyl | 496 |
| 32 | 2,6-dichlorobenzoyl | ethyl | 510 |
| 33 | 2,6-dichlorobenzoyl | n-propyl | 524 |
| 34 | 2,6-dichlorobenzoyl | n-butyl | 538 |
| 35 | 2,6-dichlorobenzoyl | phenyl | 558 |
| 36 | 2,6-dichlorobenzoyl | methoxy | 512 |
| 37 | 2,6-dichlorobenzoyl | ethoxy | 526 |
| 38 | 2,6-dichlorobenzoyl | chloromethyl | 530 |
| 39 | 2,6-dimethylbenzoyl | methyl | 456 |
| 40 | 2,6-dimethylbenzoyl | n-propyl | 484 |
| 41 | 2,6-dimethylbenzoyl | n-butyl | 498 |

TABLE 5-continued (27)

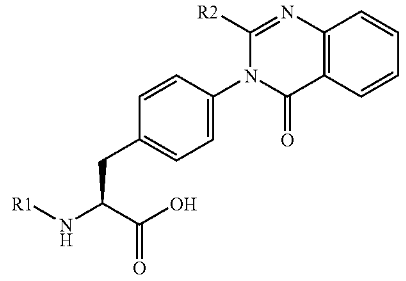

| Ref. Example | R1— | R2— | MS Found (MH+) |
|---|---|---|---|
| 42 | 2,6-dimethylbenzoyl | phenyl | 518 |
| 43 | 2,6-dimethylbenzoyl | ethoxy | 486 |
| 44 | 2,6-dimethylbenzoyl | chloromethyl | 490 |

NMR data of the compound of Reference Example 32: $^1$H-NMR (CDCl3) δ=1.21 (3H, t, J=7.4 Hz), 2.47 (2H, q, J=7.4 Hz), 3.32-3.42 (2H, m), 5.19 (1H, t, J=5.4 Hz), 7.10-7.20 (2H, m), 7.22-7.35 (4H, m), 7.43-7.54 (3H, m), 7.70-7.83 (2H, m), 8.21 (1H, d, J=7.8 Hz)

Reference Example 45

Synthesis of the Compound of the Following General Formula (28) which has a Substituent(s) of Reference Example 45 of Table 6

Process 1 Acylation 3-chloro-2-nitrobenzoic acid (210 mg, 1.04 mmol), HOAt (141 mg, 1.04 mmol), DIC (161 uL, 1.04 mmol) and NMP (2 mL) were added to the resin obtained in Process 4 of Reference Example 1 (200 mg) and stirred for 64 hours. After that, the resin was washed with DMF and dichloromethane three times each and dried under reduced pressure.

Process 2 Reduction of Nitro Group

The resin obtained in Process 1 was treated in accordance with Process 4 of Reference Example 1.

Process 3 Construction of quinazoline-2,4-dione Ring

Carbonyldiimidazole (844 mg, 5.21 mmol) and NMP (2 mL) were added to the resin obtained in Process 2 and stirred at 80° C. for 16 hours. After washing it with DMF and dichloromethane three times each and drying under reduced pressure, the resin was treated in accordance with Process 7 of Reference Example 1 to obtain the intended compound.

MS(ESI MH+): 532

CHNO: C24H16Cl3N3O5

Reference Examples 46 to 54

The compounds shown in Table 6 were synthesized by the same procedure as that of Reference Example 45 except that respective corresponding substituted 2-nitrobenzoic acid was used in Process 1 of Reference Example 45. Meanwhile, R1, R2, R3 and R4 in Table 6 are a substituent(s) in the following general formula (28).

TABLE 6

(28)

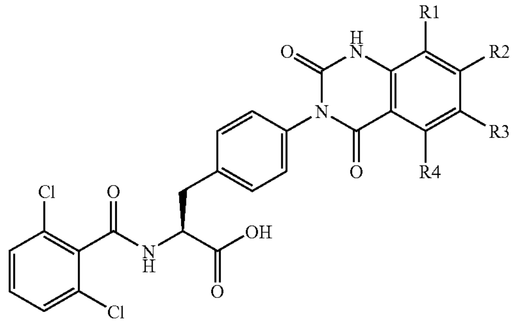

| Ref. Exam. | R1— | R2— | R3 | R4 | MS Found (MH+) |
|---|---|---|---|---|---|
| 45 | chloro | H— | H— | H— | 532 |
| 46 | methoxy | H— | H— | H— | 528 |
| 47 | H— | H— | chloro | H— | 532 |
| 48 | H— | H— | methoxy | H— | 528 |
| 49 | H— | trifluoromethyl | H | H— | 566 |
| 50 | methyl | H— | H— | H— | 512 |
| 51 | H— | methoxy | methoxy | H— | 558 |
| 52 | H— | H— | fluoro | H— | 516 |
| 53 | H— | H— | H— | methyl | 512 |
| 54 | H— | H— | H— | chloro | 532 |

Reference Example 57

Synthesis of the Compound of the Following General Formula (29) which has a Substituent(s) of Reference Example 57 of Table 8

Process 1 Acylation 2-fluoro-5-nitrobenzoic acid (1.63 g, 8.81 mmol), HOAt (1.2 g, 8.81 mmol), DIC (675 uL, 4.36 mmol) and NMP (25 mL) were added to the resin obtained in Process 4 of Reference Example 1 (1 g) and stirred for 14 hours. After that, the resin was washed with DMF and dichloromethane three times each and dried under reduced pressure.

Process 2 Substitution of Fluoro Group with Amine

Isopropylamine (400 uL) and NMP (2 mL) were added to the resin obtained in Process 1 (200 mg) and stirred for 21 hours. After that, the resin was washed with DMF and dichloromethane three times each and dried under reduced pressure.

Process 3 Construction of quinazoline-2,4-dione Ring

Carbonyldiimidazole (200 mg) and trans-decahydronaphthalene (2 mL) were added to the resin obtained in Process 2 and stirred at 95° C. for 15 hours. After washing it with DMF, methanol and dichloromethane three times each and drying under reduced pressure, the resin was treated in accordance with Process 7 of Reference Example 1 to obtain the intended compound.

MS(ESI MH+): 585

CHNO: C27H22Cl2N4O7

Reference Examples 58 to 65

The compounds shown in Table 8 were synthesized by the same procedure as that of Reference Example 57 except that respective corresponding amine was used in Process 2 of Reference Example 57. Meanwhile, R in Table 8 is a substituent in the following general formula (29).

TABLE 8

(29)

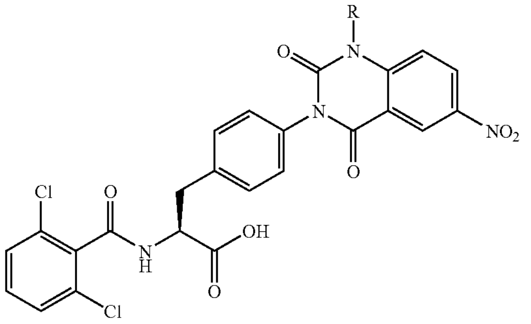

| Ref. Example | R— | MS Found (MH+) |
|---|---|---|
| 57 | isopropyl | 585 |
| 58 | sec-butyl | 599 |
| 59 | cyclobutyl | 597 |
| 60 | cyclopentyl | 611 |
| 61 | isobutyl | 599 |
| 62 | cyclohexylmethyl | 639 |
| 63 | methyl | 557 |
| 64 | cyclopropyl | 583 |
| 65 | benzyl | 633 |

Reference Example 66

Synthesis of the Compound of the Following General Formula (30) which has a Substituent(s) of Reference Example 66 of Table 9

Process 1 Substitution of Fluoro Group with Amine

THF solution of 2.0M methylamine (3 mL) and NMP (2 mL) were added to the resin obtained in Process 1 of Reference Example 57 (150 mg) and stirred for 14 hours. After that, the resin was washed with DMF and dichloromethane three times each and dried under reduced pressure.

Process 2 Construction of quinazoline-2-thioxo-4-one

Thiocarbonyldiimidazole (200 mg) and trans-decahydronaphthalene (2 mL) were added to the resin obtained in Process 1 and stirred at 95° C. for 15 hours. After washing it with DMF, methanol and dichloromethane three times each and drying under reduced pressure, the resin was treated in accordance with Process 7 of Reference Example 1 to obtain the intended compound.

MS(ESI MH+): 573

CHNO: C25H18Cl2N4O6S

Reference Examples 67 to 69

The compounds shown in Table 9 were synthesized by the same procedure as that of Reference Example 66 except that respective corresponding amine was used in Process 1 of Reference Example 66. Meanwhile, R in Table 9 is a substituent in the following general formula (30).

TABLE 9

(30)

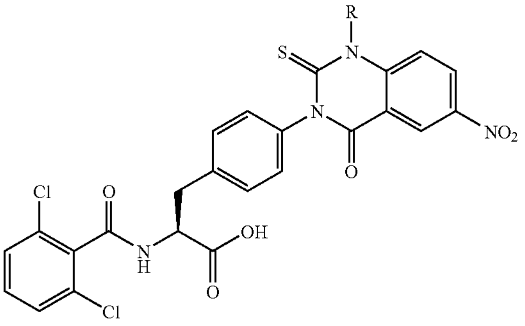

| Ref. Example | R— | MS Found (MH+) |
|---|---|---|
| 66 | methyl | 573 |
| 67 | ethyl | 587 |
| 68 | cyclopropyl | 599 |
| 69 | benzyl | 649 |

Reference Example 70

Synthesis of the Compound of the Following General Formula (31) which has a Substituent(s) of Reference Example 70 of Table 10

Process 1 Acylation 2-amino-3,6-dichlorobenzoic acid (845 mg, 4.10 mmol), HOAt (558 g, 4.10 mmol), DIC (317 uL, 2.05 mmol) and NMP (11.5 mL) were added to the resin obtained in Process 4 of Reference Example 1 (500 mg) and stirred for 24 hours. After that, the resin was washed with DMF, methanol and dichloromethane three times each and dried under reduced pressure.

Process 2 Construction of quinazoline-2,4-dione Ring

Carbonyldiimidazole (200 mg) and trans-decahydronaphthalene (2 mL) were added to the resin obtained in Process 1 (200 mg) and stirred at 95° C. for 15 hours. After that the resin was washed with DMF, methanol and dichloromethane three times each and dried under reduced pressure.

Process 3 Alkylation

The resin obtained in Process 2 was alkylated in accordance with Process 6 of Reference Example 1.

Process 4 Cleavage from Resin

The intended compound was obtained by being treated in accordance with Process 7 of Reference Example 1.

MS(ESI MH+): 580

CHNO: C25H17Cl4N3O5

Reference Examples 71 to 80

The compounds of Reference Examples 71 to 75 were synthesized by the same procedure as that of Reference Example 70 except that respective corresponding benzoic acid derivatives were used in Process 1 of Reference Example 70. The same procedure as that of Reference Example 70 was repeated in Reference Examples 76 to 80 except that alkylation in Process 3 of Reference Example 70 was not conducted. Meanwhile, R in Table 10 is substituents in the following general formula (31).

TABLE 10

(31)

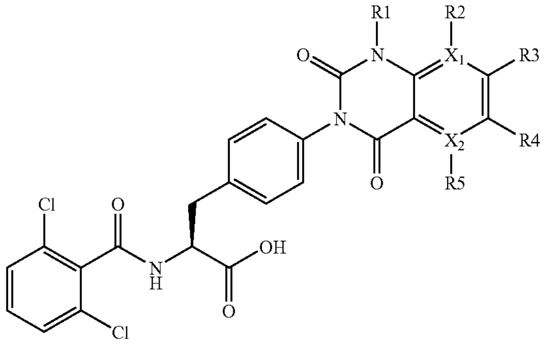

| Ref. Example | R1— | R2— | R3— | R4— | R5— | X1 | X2 | MS Found (MH+) |
|---|---|---|---|---|---|---|---|---|
| 70 | methyl | chloro | H | H | chloro | C | C | 580 |
| 71 | methyl | chloro | H | chloro | H | C | C | 580 |
| 72 | methyl | H | fluoro | H | H | C | C | 530 |
| 73 | methyl | H | H | Br | H | C | C | 591 |
| 74 | methyl | — | H | H | H | N | C | 513 |
| 75 | methyl | — | H | H | — | N | N | 514 |
| 76 | H | chloro | H | H | chloro | C | C | 566 |
| 77 | H | chloro | H | chloro | H | C | C | 566 |
| 78 | H | H | fluoro | H | H | C | C | 516 |
| 79 | H | — | H | H | H | N | C | 499 |
| 80 | H | — | H | H | — | N | N | 500 |

Reference Example 81

Synthesis of the Compound of the Following General Formula (32) which has a Substituent(s) of Reference Example 81 of Table 11

Process 1 Acylation

The resin obtained in Process 4 of Reference Example 1 was acylated in accordance with Process 1 of Example 70.

Process 2 Construction of Triazene Ring

Sodium nitrite (150 mg) and acetic acid (4.5 ml) were added to the resin obtained in Process 1 (90 mg) and stirred for 24 hours. After washing it with DMF, methanol and dichloromethane three times each and drying under reduced pressure, the intended compound was obtained by being treated in accordance with Process 7 of Reference Example 1.

MS(ESI MH+): 551

CHNO: C23H14Cl4N4O4

Reference Examples 82 and 83

The compounds of Reference Examples 82 and 83 shown in Table 11 were synthesized by the same procedure as that of Reference Example 81 except that respective corresponding 2-aminobenzoic acid was used in Process 1 of Reference Example 81. Meanwhile, R1, R2, R3 and R4 in Table 11 are substituents in the following general formula (32).

Reference Example 84

Synthesis of the Compound of the Following General Formula (32) which has a Substituent(s) of Reference Example 84 of Table 11

Process 1 Acylation, Reduction of Nitro Group

Acylation was conducted by using the resin obtained in Process 4 of Reference Example 1 (1 g), 5-methoxy-2-nitrogenzoic acid (1.62 g, 8.21 mmol), DIC (635 uL, 4.11 mmol), HOAt (1.12 g, 8.21 mmol) and NMP 23 mL). Then, the nitro group was reduced in accordance with Process 2 of Reference Example 31.

Process 2 Construction of Triazene Ring, Cleavage from Resin

The resin obtained in Process 1 was treated in accordance with Process 2 of Reference Example 81 and then treated in accordance with Process 7 of Reference Example 1 to obtain the intended compound.

MS(ESI MH+): 513

CHNO: C24H18Cl2N4O5

Reference Examples 85 to 89

The compounds of Reference Examples 85 to 89 shown in Table 11 were synthesized by the same procedure as that of Reference Example 84 except that respective corresponding 2-nitrobenzoic acid was used in Process 1 of Reference Example 84. Meanwhile, R1, R2, R3 and R4 in Table 11 are substituents in the following general formula (32).

Reference Example 90

Synthesis of the Compound of the Following General Formula (32) which has a Substituent(s) of Reference Example 90 of Table 11

Process 1 Construction of Triazene Ring, Cleavage from Resin

The resin obtained in Process 2 of Reference Example 31 was treated in accordance with Process 2 of Reference Example 81 and then treated in accordance with Process 7 of Reference Example 1 to obtain the intended compound.

MS(ESI MH+): 483.

CHNO: C23H16Cl2N4O4

TABLE 11

(32)

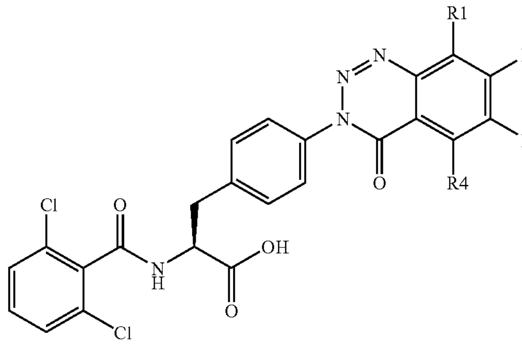

| Ref. Exam. | R1— | R2— | R3 | R4 | MS Found (MH+) |
|---|---|---|---|---|---|
| 81 | chloro | H— | H— | chloro | 551 |
| 82 | chloro | H— | chloro | H— | 551 |
| 83 | H— | fluoro | H— | H— | 501 |
| 84 | H— | H— | methoxy | H— | 513 |
| 85 | H— | H— | fluoro | H— | 501 |
| 86 | methyl | H— | H— | H— | 497 |
| 87 | H— | H— | chloro | H— | 517 |
| 88 | chloro | H— | H— | H— | 517 |
| 89 | H— | H— | H— | methyl | 497 |
| 90 | H— | H— | H— | H— | 483 |

Reference Example 91

Synthesis of the Compound of the Following General Formula (33) which has a Substituent(s) of Reference Example 91 of Table 12

Process 1 Acylation, Reduction of Nitro Group

Acylation and reduction of a nitro group were conducted in accordance with Process 1 of Reference Example 84 by using the resin obtained in Process 4 of Reference Example 1.

Process 2 Cyclization by Ortho Ester and Cleavage from Resin

Tetraethoxymethane (800 ul), acetic acid (200 ul), and NMP (2 ml) were added to the resin obtained in Process 1 (150 mg) and stirred at 55° C. for 15 hours. After washing it with DMF, methanol and dichloromethane three times each and drying under reduced pressure, the resin was treated in accordance with Process 7 of Reference Example 1 to obtain the intended compound.

MS(ESI MH+): 556

CHNO: C27H23Cl2N3O6

Reference Examples 92 to 94

The compounds of Reference Examples 92 to 94 shown in Table 12 were synthesized by the same procedure as that of Reference Example 91 except that respective corresponding 2-nitrobenzoic acid was used in Process 1 of Reference Example 91. Meanwhile, R1, R2, R3 and R4 in Table 12 are substituents in the following general formula (33).

Reference Example 95

Synthesis of the Compound of the Following General Formula (33) which has a Substituent(s) of Reference Example 95 of Table 12

Process 1 Acylation 2-amino-4-fluorobenzoic acid (636 mg, 4.10 mmol), HOAt (558 g, 4.10 mmol), DIC (317 uL, 2.05 mmol) and NMP (11.5 mL) were added to the resin obtained in Process 4 of Reference Example 1 (500 mg) and stirred for 24 hours. After that, the resin was washed with DMF, methanol and dichloromethane three times each and dried under reduced pressure.

Process 2 Cyclization with Ortho Ester and Cleavage from Resin

The resin obtained in Process 1 was cyclized in accordance with Process 2 of Reference Example 91 and then the intended compound was obtained by being treated in accordance with Process 7 of Reference Example 1.

MS(ESI MH+): 544

CHNO: C26H20Cl2FN3O5

TABLE 12

(33)

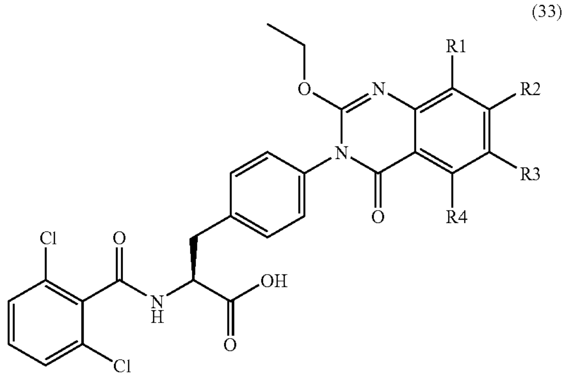

| Ref. Exam. | R1— | R2— | R3 | R4 | MS Found (MH+) |
|---|---|---|---|---|---|
| 91 | H— | H— | methoxy | H— | 556 |
| 92 | H— | H— | fluoro | H— | 544 |
| 93 | H— | H— | chloro | H— | 560 |
| 94 | H— | H— | H— | methyl | 540 |
| 95 | H— | fluoro | H— | H— | 544 |

Reference Example 96

Synthesis of the Compound of the Following General Formula (34) which has a Substituent(s) of Reference Example 96 of Table 13

Process 1 Acylation, Reduction of Nitro Group

Acylation was conducted by reacting the resin obtained in Process 4 of Reference Example 1 (1 g) with 6-methyl-2- nitrobenzoic acid (1.49 g, 8.21 mmol), DIC (635 uL, 4.11 mmol), HOAt (1.12 g, 8.21 mmol) and NMP (23 mL) for 18 hours. Then, the nitro group was reduced in accordance with Process 2 of Reference Example 31.

Process 2 Cyclization

Carbonyldiimidazole (400 mg) and NMP (2 mL) were added to the resin obtained in Process 1 (200 mg) and stirred at 95° C. for 15 hours. After that, the resin was washed with DMF, methanol and dichloromethane three times each and dried under reduced pressure.

Process 3 Alkylation

Ethyl iodide (200 ul) and tetramethyl guanidine (200 ul) were added to the resin obtained in Process 2 (200 mg) and stirred for 24 hours. After washing it with water, DMF, methanol and dichloromethane three times each and drying under reduced pressure, the resin was treated in accordance with Process 7 of Reference Example 1 to obtain the intended compound.

MS(ESI MH+): 540

CHNO: C27H23Cl2N3O5

Reference Example 97

The compounds of Reference Examples 97 shown in Table 13 was synthesized by the same procedure as that of Reference Example 96 except that the corresponding halide was used in Process 3 of Reference Example 96. Meanwhile, R in Table 13 is a substituent in the following general formula (34).

TABLE 13

(34)

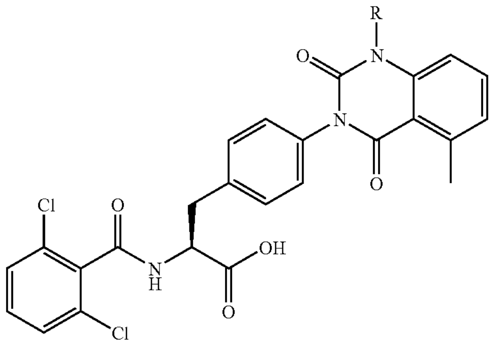

| Ref. Example | R— | MS Found (MH+) |
|---|---|---|
| 96 | ethyl | 540 |
| 97 | benzyl | 602 |

Reference Example 98

Synthesis of the Compound of the Following General Formula (35) which has a Substituent(s) of Reference Example 98 of Table 14

Process 1 Sulfonamidation, Reduction of Nitro Group 2-nitrobenzenesulfonyl chloride (450 mg), 2,6-lutidine (450 ul) and dichloromethane (10 ml) were added to the resin obtained in Process 4 of Reference Example 1 (400 mg) and stirred for 14 hours. After washing it with DMF, methanol and dichloromethane three times each and drying under reduced pressure, the nitro group was reduced in accordance with Process 2 of Reference Example 31.

Process 2 Cyclization

Carbonyldiimidazole (400 mg) and NMP (2 mL) were added to the resin obtained in Process 1 (200 mg) and stirred at 95° C. for 15 hours. After that the resin was washed with DMF, methanol and dichloromethane three times each and dried under reduced pressure.

Process 3 Alkylation, Cleavage from Resin

Methyl iodide (400 ul), diisopropylethylamine (400 ul) and NMP (2 ml) were added to the resin obtained in Process 2 (200 mg) and stirred for 17 hours. After washing it with water, DMF, methanol and dichloromethane three times each and drying under reduced pressure, the resin was treated in accordance with Process 7 of Reference Example 1 to obtain the intended compound.

MS(ESI MH+): 548

CHNO: C24H19Cl2N3O6S

Reference Examples 99 to 103

The compounds shown in Table 14 were synthesized by the same procedure as that of Reference Example 98 except that respective corresponding sulfonyl chlorides were used in Process 1 of Reference Example 98. Meanwhile, R1, R2, R3, R4 and R5 in Table 14 are substituents in the following general formula (35) and the same procedure as that of Reference Example 98 was repeated in Reference Examples 101 to 103 except that alkylation in Process 3 of Reference Example 98 was not conducted.

TABLE 14

(35)

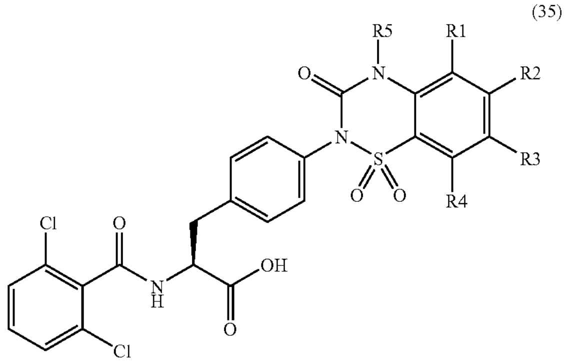

| Ref. Exam. | R1— | R2— | R3— | R4— | R5— | MS Found (MH+) |
|---|---|---|---|---|---|---|
| 98 | H— | H— | H— | H— | methyl | 548 |
| 99 | H— | methoxy | H— | H— | methyl | 578 |
| 100 | H— | trifluoromethyl | H— | H— | methyl | 616 |
| 101 | H— | H— | H— | H— | H— | 534 |
| 102 | H— | methoxy | H— | H— | H— | 564 |
| 103 | H— | trifluoromethyl | H— | H— | H— | 602 |

Reference Example 104

Synthesis of the Compound of the Following General Formula (36) which has a Substituent(s) of Reference Example 104 of Table 15

Process 1 Acylation, Construction of quinazoline-2,4-dione ring, Alkylation and Reduction of Nitro Group Acylation was conducted by using the resin obtained in Process 4 of Reference Example 1 (500 mg), 2-amino-5-nitrobenzoic acid (746 mg, 4.10 mmol), DIC (317 ul, 2.05 mmol), HOAt (558 mg, 4.10 mmol) and NMP (11.5 ml). Then quinazoline-2,4-dione ring was constructed in accordance with Process 2 of Reference Example 96 and alkylation was conducted in accordance with Process 6 of Reference Example 1. Further, the nitro group was reduced in the same way of Process 4 of Reference Example 1.

Process 2 Acylation

Acetic anhydride (600 ul), pyridine (600 ul) and NMP (3 ml) were added to the resin obtained in Process 1 and stirred for 19 hours. After washing it with water, DMF, methanol and dichloromethane three times each and drying under reduced pressure, the resin was treated in accordance with Process 7 of Reference Example 1 to obtain the intended compound.

MS(ESI MH+): 569

CHNO: C27H22Cl2N4O6

Reference Examples 105 to 107

The compounds shown in Table 15 were synthesized by the same procedure as that of Reference Example 104 except that the corresponding acid chloride was used in Process 2 of Reference Example 104. Meanwhile, R in Table 15 is a substituent in the following general formula (36) and the same procedure as that of Reference Example 104 was repeated in Reference Example 107 except that acylation in Process 2 of Reference Example 104 was not conducted.

TABLE 15

(36)

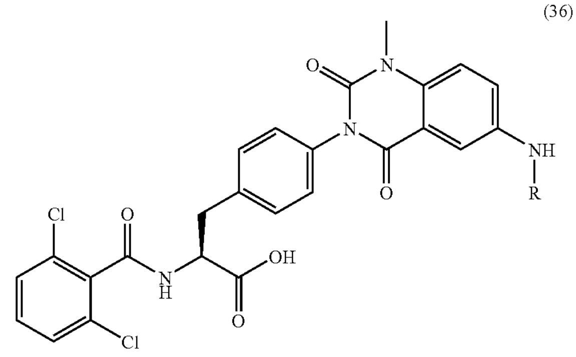

| Ref. Example | R— | MS Found (MH+) |
|---|---|---|
| 104 | acetyl | 569 |
| 105 | methoxyacetyl | 599 |
| 106 | pivaloyl | 611 |
| 107 | H | 527 |

Reference Example 108

Synthesis of the Compound of the Following General Formula (37) which has a Substituent(s) of Reference Example 108 of Table 16

Process 1 Acylation

The resin obtained in Process 4 of Reference Example 1 (1 g) was acylated by using 5-fluoro-2-nitrobenzoic acid (1.63 g, 8.81 mmol), DIC (675 ul, 4.36 mmol), HOAt (1.2 g, 8.81 mmol) and NMP (25 ml).

Process 2 Substitution of Fluoro Group with Amine, Reduction of Nitro Group

THF solution of 2.0M dimethylamine (3 mL) and NMP (2 mL) were added to the resin obtained in Process 1 (200 mg) and stirred for 14 hours. After washing it with water, DMF and dichloromethane three times each and drying under reduced pressure, the nitro group was reduced in accordance with Process 2 of Reference Example 31.

Process 3 Construction of quinazoline-2,4-dione Ring

The resin obtained in Process 2 was treated in accordance with Process 2 of Reference Example 96 to construct quinazoline-2,4-dione ring.

Process 4 Alkylation

Triphenylphosphine (520 mg), methanol (80 ul), 40% toluene solution of diisopropylazodicarboxylic acid (1 ml) and dichloromethane (2 ml) were added to the resin obtained in Process 3 and stirred for 7 hours. After washing it with water, DMF, methanol and dichloromethane three times each and drying under reduced pressure, the resin was treated in accordance with Process 7 of Reference Example 1 to obtain the intended compound.

MS(ESI MH+): 555

CHNO: C27H24Cl2N4O5

Reference Examples 109 to 111

The compounds of Reference Examples 109 to 111 shown in Table 16 were synthesized by the same procedure as that of Reference Example 108 except that the corresponding amine was used in Process 2 of Reference Example 108. Meanwhile, R in Table 16 is a substituent in the following general formula (37).

Reference Example 112

Synthesis of the Compound of the Following General Formula (37) which has a Substituent(s) of Reference Example 112 of Table 16

Process 1 Substitution of Fluoro Group by Amine, Reduction of Nitro Group

THF solution of 2.0M dimethylamine (3 mL) and NMP (2 mL) were added to the resin obtained in Process 1 (200 mg) of Reference Example 108 and stirred for 14 hours. After washing it with water, DMF and dichloromethane three times each and drying under reduced pressure, the nitro group was reduced in accordance with Process 2 of Reference Example 31.

Process 3 Construction of quinazoline-2,4-dione Ring

The resin obtained in Process 2 was treated in accordance with Process 2 of Reference Example 96 to construct quinazoline-2,4-dione ring.

Process 4 Alkylation

Methyl iodide (400 ul), diisopropylethylamine (400 ul) and NMP (2 ml) were added to the resin obtained in Process 3 (200 mg) and stirred for 17 hours. After washing it with water, DMF, methanol and dichloromethane three times each and drying under reduced pressure, the resin was treated in accordance with Process 7 of Reference Example 1 to obtain the intended compound.

MS(ESI MH+): 569

CHNO: C28H27Cl2N4O5

Reference Example 113

The compound of Reference Example 113 shown in Table 16 was synthesized by the same procedure as that of Reference Example 112 except that the corresponding amine was used in Process 1 of Reference Example 112. Meanwhile, R in Table 16 is a substituent in the following general formula (37).

TABLE 16

(37)

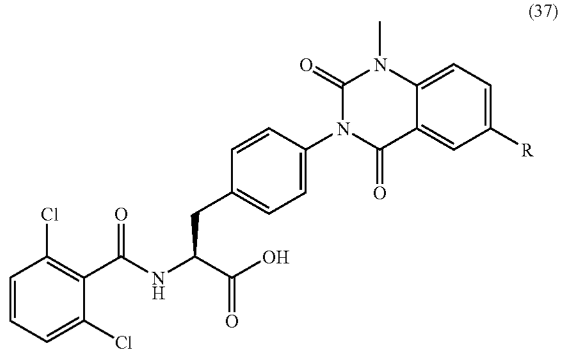

| Ref. Example | R— | MS Found (MH+) |
|---|---|---|
| 108 | dimethylamino | 555 |
| 109 | ethylmethylamino | 569 |
| 110 | pyrrolidyl | 581 |
| 111 | diethylamino | 583 |
| 112 | formula X 1 | 569 |
| 113 | formula X 2 | 595 |

Formulae X1 and X2 are described below.

NMR data of the compound of Reference Example 108: $^{1}$H-NMR (400 MHz, DMSO-$d_6$) δ 2.94 (6H, m), 3.02 (1H, dd, J=10.2, 14.1 Hz), 3.22 (1H, m, J=4.4, 14.1 Hz), 3.49 (3H, s), 4.82 (1H, m), 7.17 (2H, d), 7.24 (1H, d), 7.30 (1H, m), 7.36-7.45 (5H, m), 9.15 (1H, d). $^{13}$C-NMR (100 MHz, DMSO-$d_6$) δ 30.90, 36.64, 40.77, 53.68, 109.21, 116.00, 116.22, 121.37, 128.26, 128.93, 129.90, 131.23, 131.82, 132.10, 135.23, 136.56, 137.57, 146.72, 150.38, 161.88, 163.91, 172.72.

Formula X1

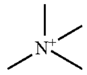

Formula X2

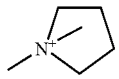

Reference Example 114

Synthesis of the Compound of the Following General Formula (38) which has a Substituent(s) of Reference Example 114 of Table 17

Process 1 Alkylation 2,6-dichlorobenzyl alcohol (531 mg), triphenylphosphine (786 mg), dichloromethane (3 ml) and 40% toluene solution of diisopropylazodicarboxylic acid (1.5 ml) were added to the resin obtained in Process 5 of Reference Example 1 (150 mg) and stirred for 14 hours. After washing it with water, DMF, methanol and dichloromethane three times each and drying under reduced pressure, the resin was treated in accordance with Process 7 of Reference Example 1 to obtain the intended compound.

MS(ESI MH+): 656

CHNO: C31H21Cl4N3O5

Reference Examples 115 to 123

The compounds of Reference Examples 115 to 123 shown in Table 17 were synthesized by the same procedure as that of Reference Example 114 except that respective corresponding alcohol was used in Process 1 of Reference Example 114. Meanwhile, R1, R2, R3, R4, R5 and n in Table 17 are substituents in the following general formula (38).

Reference Example 124

Synthesis of the Compound of the Following General Formula (38) which has a Substituent(s) of Reference Example 124 of Table 17

Process 1 Acylation

The resin obtained in Process 4 of Reference Example 1 (150 mg) was acylated by using N-phenylanthranilic acid (437 mg, 2.05 mmol), HOAt (279 mg, 2.05 mmol), DIC (106 ul, 1.03 mmol) and NMP(6 ml).

Process 2 Construction of quinazoline-2,4-dione Ring

The resin obtained in Process 1 was treated in accordance with Process 2 of Reference Example 96. After quinazoline-2,4-dione ring was constructed, the resin was treated in accordance with Process 7 of Reference Example 1 to obtain the intended compound.

MS(ESI MH+): 574

CHNO: C30H21Cl2N3O5

TABLE 17

(38)

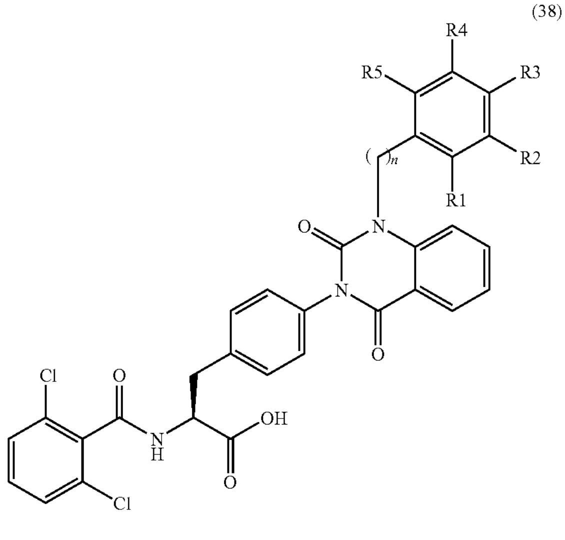

| Ref. Exam. | R1— | R2— | R3— | R4— | R5— | n= | MS Found (MH+) |
|---|---|---|---|---|---|---|---|
| 114 | chloro | H | H | H | chloro | 1 | 656 |
| 115 | H | chloro | chloro | H | H | 1 | 656 |
| 116 | chloro | H | chloro | H | H | 1 | 656 |
| 117 | H | H | chloro | H | H | 1 | 622 |
| 118 | H | H | methyl | H | H | 1 | 602 |
| 119 | chloro | H | H | H | H | 1 | 622 |

TABLE 17-continued (38)

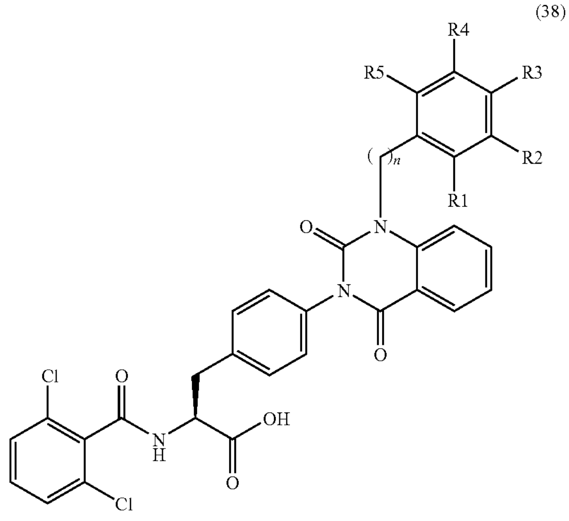

| Ref. Exam. | R1— | R2— | R3— | R4— | R5— | n= | MS Found (MH+) |
|---|---|---|---|---|---|---|---|
| 120 | methyl | H | H | H | H | 1 | 602 |
| 121 | chloro | H | H | H | fluoro | 1 | 640 |
| 122 | H | H | H | H | H | 1 | 588 |
| 123 | H | H | H | H | H | 2 | 602 |
| 124 | H | H | H | H | H | 0 | 574 |

Reference Example 125

Synthesis of the Compound of the Following General Formula (39) which has a Substituent(s) of Reference Example 125 of Table 18

Process 1 Synthesis of Iminophosphine

Triphenylphosphine (7.86 g), 40% toluene solution of diisopropylazodicarboxylic acid (30 ml) and toluene (30 ml) were added to the resin obtained in Process 4 of Reference Example 1 (1 g) and stirred for 16 hours. After that, the resin was washed with dichloromethane ten times and dried under reduced pressure.

Process 2 Synthesis of Carbodiimide, Nucleophilic Addition of Amine and Ring Closure Methyl 2-isocyanatebenzoate (200 mg) and dichloromethane (1 ml) were added to the resin obtained in Process 1 (100 mg), stirred for 1 hour and washed with DMF and dichloromethane three times each. Cyclobutylamine (600 ul) and NMP (3 ml) were added to the obtained resin and stirred for 13 hours. After washing it with DMF, methanol and dichloromethane and drying under reduced pressure, the resin was treated in accordance with Process 7 of Reference Example 1 to obtain the intended compound.

MS(ESI MH+): 551

CHNO: C28H24Cl2N4O4

Reference Examples 126 to 130

The compounds shown in Table 18 were synthesized by the same procedure as that of Reference Example 125 except that respective corresponding amine was used in Process 2 of Reference Example 125. Meanwhile, R in Table 18 is a substituent in the following general formula (39).

TABLE 18

(39)

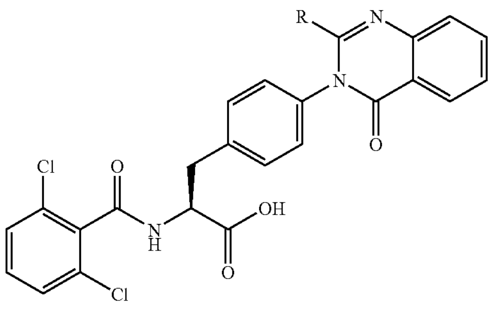

| Ref. Example | R— | MS Found (MH+) |
|---|---|---|
| 125 | cyclobutylamino | 551 |
| 126 | isobutylamino | 553 |
| 127 | isopropylamino | 539 |
| 128 | dimethylamino | 525 |
| 129 | ethylmethyamino | 539 |
| 130 | azetidino | 537 |

Reference Example 131

Synthesis of the Compound of the Following General Formula (40) which has a Substituent(s) of Reference Example 131 of Table 18

Process 1 Substitution of Fluoro Group with Amine

THF solution of 2.0M methylamine (3 mL) and NMP (2 mL) were added to the resin obtained in Process 1 of Reference Example 57 (150 mg) and stirred for 14 hours. Then the resin was washed with DMF and dichloromethane three times each and dried under reduced pressure.

Process 2 Ring Closure with Thionyl Chloride

Triazole (250 mg), thionyl chloride (80 ul), dichloromethane (1 ml) and diisopropylethylamine (400 ul) were added to the resin obtained in Process 1 and stirred for 15 hours. After washing it with DMF, methanol and dichloromethane three times each and drying under reduced pressure, the resin was treated in accordance with Process 7 of Reference Example 1 to obtain the intended compound.

MS(ESI MH+): 576

CHNO: C24H18Cl2N4O7S

Reference Examples 132 and 133

The compounds shown in Table 18 were synthesized by the same procedure as that of Reference Example 131 except that respective corresponding amine was used in Process 1 of Reference Example 131. Meanwhile, R in Table 18 is a substituent in the following general formula (40).

TABLE 18

(40)

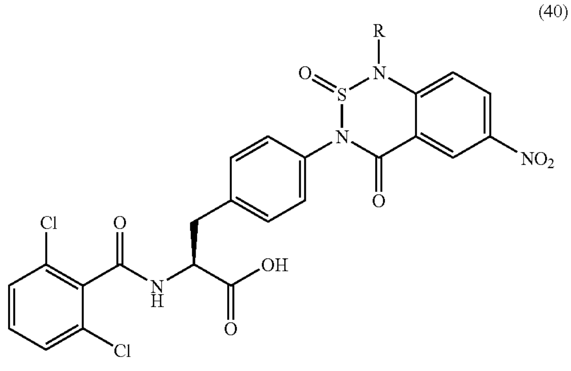

| Ref. Example | R— | MS Found (MH+) |
|---|---|---|
| 131 | methyl | 576 |
| 132 | ethyl | 590 |
| 133 | benzyl | 652 |

Reference Example 134

Synthesis of the Compound of the Following General Formula (41) which has a Substituent(s) of Reference Example 134 of Table 19

Process 1 Acylation, Removal of Fmoc Group

Acylation was conducted by reacting the resin obtained in Process 4 of Reference Example 1 (500 mg) with Fmoc-β-alanine (810 mg, 2.60 mmol), DIC (200 ul, 1.30 mmol), HOAt (351 mg, 2.60 mmol) and NMP (10 ml) for 18 hours and then Fmoc group was removed in accordance with Process 2 of Reference Example 1.

Process 2 Ring Closure with Carbonyldiimidazole

Carbonyldiimidazole (400 mg) and NMP (2 ml) were added to the resin obtained in Process 1 and stirred for 3 hours. Then, the resin was washed with DMF, methanol and dichloromethane three times each and dried under reduced pressure. Further, NMP (2 ml) was added to the obtained resin and stirred at 95° C. for 15 hours. After washing it with DMF, methanol and dichloromethane three times each and drying under reduced pressure, the resin was treated in accordance with Process 7 of Reference Example 1 to obtain the intended compound.

MS(ESI MH+): 450

CHNO: C20H17Cl2N3O5

Reference Example 135

Synthesis of the Compound of the Following General Formula (41) which has a Substituent(s) of Reference Example 135 of Table 19

Process 1 2-nitrosulfonylation, Alkylation 2-nitrosulfonyl chloride (176 mg), 2,6-lutidine (184 ul) and dichloromethane (4 ml) were added to the resin obtained in Process 1 of Reference Example 134 (250 mg) and stirred at 4° C. for 16 hours. After washing it with DMF, methanol and dichloromethane three times each and drying under reduced pressure, the obtained resin was alkylated in accordance with Process 4 of Reference Example 108.

Process 2 Removal of 2-nitrosulfonyl Group 2-mercaptoethanol (600 ul), diazabicycloundecene (300 ul) and NMP (3 ml) were added to the resin obtained in Process 1 and stirred for 1 hour. Then, the resin was washed with DMF, methanol and dichloromethane three times each and dried under reduced pressure.

Process 3 Ring Closure with Carbonyldiimidazole

Carbonyldiimidazole (500 mg) and dichloromethane (2.5 ml) were added to the resin obtained in Process 2 and stirred for 10 hours. Then, the resin was washed with DMF, methanol and dichloromethane three times each and dried under reduced pressure. Further, potassium carbonate (200 mg) and NMP (1 ml) were added to the obtained resin and stirred at 95° C. for 17 hours. After washing it with water, DMF, methanol and dichloromethane three times each and drying under reduced pressure, the resin was treated in accordance with Process 7 of Reference Example 1 to obtain the intended compound.

MS(ESI MH+): 464

CHNO: C21H19Cl2N3O5

TABLE 19

(41)

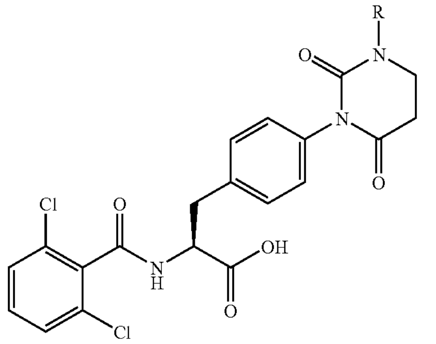

| Ref. Example | R— | MS Found (MH+) |
|---|---|---|
| 134 | H | 450 |
| 135 | methyl | 464 |

Reference Example 136

Synthesis of the Compound of the Following General Formula (73) which has a Substituent(s) of Reference Example 136 of Table 20

Process 1 Acylation, Removal of 0-acyl Group

Salicylic acid (74 mg, 0.535 mmol), PyBOP (278 mg, 0.535 mmol), HOBt (120 mg, 0.89 mmol), DIEA (0.186 ml, 1.068 mmol) and DMF (3.6 ml) were added to the resin obtained in Process 4 of Reference Example 1 and stirred for 19 hours. Then, the resin was washed with DMF, methanol and dichloromethane eight times each and 30% ethanolamine/DMF (5 ml) was added to the obtained resin and stirred for 4 hours. The resin was again washed with DMF, methanol and dichloromethane eight times each.

Process 2 Ring Closure with Carbonyldiimidazole, Cleavage from Resin

Carbonyldiimidazole (98 mg) and DCM (6 ml) were added to the resin obtained in Process 1 (50 mg), stirred for 1 hour and washed with dichloromethane five times. Further, dichloromethane (4 ml) was added to the obtained resin, stirred at room temperature for 3 hours and washed with dichloromethane five times. Then, the intended compound was obtained by cleavage from the resin and HPLC purification in the same way of Process 7 of Reference Example 1 (3 mg).

MS(ESI MH+): 499

CHNO: C24H16CL2N2O6

Reference Examples 137 to 144

The compounds shown in Table 20 were synthesized by the same procedure as that of Reference Example 136 except that the corresponding salicylic acid was used in Process 1 of Reference Example 136. Meanwhile, R1, R2 and R3 in Table 20 are substituents in the following general formula (73).

TABLE 20

(73)

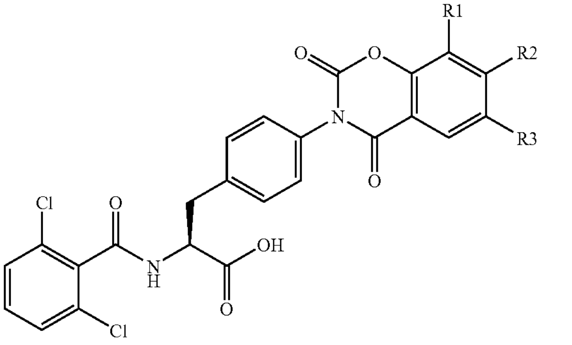

| Ref. Exam. | R1 | R2 | R3 | MS Found (MH+) |
|---|---|---|---|---|
| 136 | H | H | H | 499 |
| 137 | —CH═CH—CH═CH— | | H | 549 |
| 138 | H | H | CHO | 527 |
| 139 | H | OMe | H | 529 |
| 140 | OH | H | H | 515 |
| 141 | H | OH | H | 515 |
| 142 | H | NH2 | H | 514 |
| 143 | H | H | Cl | 533 |
| 144 | H | H | F | 517 |

Reference Example 145

Synthesis of the Compound of the Following General Formula (74)

Process 1 Ring Closure With Thiocarbonyldiimidazole

Thiocarbonyldiimidazole (500 mg) and dichloromethane (2.5 ml) were added to the resin obtained in Process 1 of Reference Example 98 and stirred at room temperature for 16 hours. Then the resin was washed with methanol, DMF and dichloromethane three times each and dried under reduced pressure.

Process 2 Cleavage from Resin

The resin obtained in Process 1 (100 mg) was treated in accordance with Process 7 of Reference Example 1 to obtain 1.2 mg of the intended compound.

MS(ESI MH+): 550

CHNO: C23H17Cl2N3O5S2

(74)

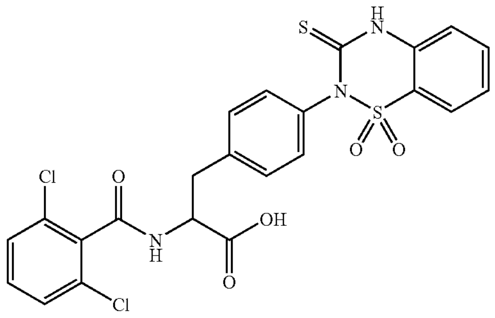

Reference Example 146

Synthesis of the Compound of the Following General Formula (75)

Methylation and Cleavage from Resin

Diisopropylethylamine (200 ul), methyl iodide (100 ul) and NMP (3 ml) were added to 100 mg of the resin obtained in Process 1 of Reference Example 145 and stirred at room temperature for 16 hours. After washing it with methanol, DMF and dichloromethane three times each and drying under reduced pressure, the resin was treated in accordance with Process 7 of Reference Example 1 to obtain 13 mg of the intended compound.

MS(ESI MH+): 564

CHNO: C24H19Cl2N3O5S2

(75)

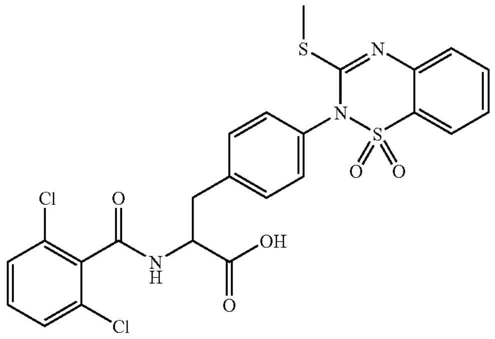

Reference Example 147

Synthesis of the Compound of the Following General Formula (76) which has a Substituent(s) of Reference Example 147 of Table 21

The resin obtained in Process 4 of Reference Example 1 was prepared to be a starting material. 500 mg of 2-nitrobenzylbromide, 500 μl of diisopropylethylamine and 5 ml of NMP were added to 100 mg of the said resin and stirred at room temperature for 12 hours. After removing the reaction solvent, the resin was washed with dichloromethane, NMP and dichloromethane three times each. NMP (0.5 mL)·EtOH(3 mL) solution of $SnCl_2.2H_2O$ (1.5 g) was added to the obtained resin and reacted for 16 hours. The reaction solvent was removed and the resin was washed with NMP and dichloromethane three times each. Further, 200 mg of 2-nitrobenzenesulfonyl chloride, 400 μl of 2,6-lutidine and 2 ml of dichloromethane were added to the obtained resin and reacted at 0° C. for 24 hours. After removing the reaction solvent, the resin was washed with dichloromethane, NMP and dichloromethane three times each. 200 μl of methyl iodide, 0.5 g of potassium carbonate and 7.5 ml of NMP were added to the sulfonamide resin and shaken at 45° C. for 24 hours. After removing the reaction solvent, the resin was washed with dichloromethane, NMP and dichloromethane three times each. 200 μl of Diazabicycloundecene, 400 μl of 2-mercaptoethanol and 500 μl of NMP were added to the obtained resin and stirred at room temperature for 24 hour. Then, the reaction solvent was removed and the resin was washed with dichloromethane, NMP and dichloromethane three times each. Further, 500 mg of carbonyldiimidazole and 4 ml of dichloromethane were added to the obtained resin and shaken at 50° C. form 24 hours. Then, the reaction solvent was removed and the resin was washed with dichloromethane, NMP and dichloromethane three times each and dried under reduced pressure. The obtained resin was treated with 100% trifluoroacetic acid for 1 hour and the resin was filtrated. The obtained filtrate was concentrated and purified by reverse phase HPLC (SYMMETRY 19*50 mm mobile phase water:acetonitrile both of which contained 0.1% TFA) to obtain 0.9 mg of the intended compound.

MS(ESI MH+): 498, 500

CHNO: C25H21Cl2N3O4

Reference Example 148

Synthesis of the Compound of the Following General Formula (76) which has a Substituent(s) of Reference Example 148 of Table 21

The resin as a starting material was prepared in the same way as that of Reference Example 147. Thiocarbonyldiimidazole instead of carbonyldiimidazole used in Reference Example 147 was used to obtain 0.8 mg of the intended compound.

MS(ESI MH+): 514, 516

CHNO: C25H21Cl2N3O3S

Reference Example 149

Synthesis of the Compound of the Following General Formula (76) which has a Substituent(s) of Reference Example 149 of Table 21

The resin obtained in Process 4 in Reference Example 1 was prepared to be a starting material. 500 mg of 2-nitrobenzylbromide, 500 μl of diisopropylethylamine and 5 ml of NMP were added to 100 mg of the resin and stirred at room temperature for 12 hours. After removing the reaction solvent, the resin was washed with dichloromethane, NMP and dichloromethane three times each. NMP (0.5 mL).EtOH (3 mL) solution of $SnCl_2.2H_2O$ (1.5 g) was added to the obtained resin and reacted for 16 hours. After removing the reaction solvent, the resin was washed with DMF and dichloromethane three times each. Further, 500 mg of carbonyldiimidazole and 4 ml of dichloromethane were added to the resin and shaken at 50° C. for 24 hours. After removing the reaction solvent, the resin was washed with dichloromethane, NMP and dichloromethane three times each and dried under reduced pressure. The obtained resin was treated with 100% solution of trifluoroacetic acid for 1 hour and the resin was filtrated. The obtained filtrate was concentrated and purified by reverse phase HPLC (SYMMETRY 19*50 mm mobile phase water:acetonitrile both of which contained 0.1% TFA) to obtain 0.9 mg of the intended compound.

MS(ESI MH+): 484, 486

CHNO: C24H19Cl2N3O4

Reference Example 150

Synthesis of the Compound of the Following General Formula (76) which has a Substituent(s) of Reference Example 150 of Table 21

1.6 mg of the intended compound was synthesized in the same way as that of Reference Example 149 by using 2-fluoro-6-nitrobenzyl bromide.

MS(ESI MH+): 502, 504

CHNO: C24H18Cl2FN3O4

Reference Examples 151 to 159

The compounds shown in Table 21 were synthesized by the same procedure as that of Reference Example 147 except that respective corresponding alkylation reagent was used instead of methyl iodide used in the synthesizing process of Reference Example 147. Meanwhile, R1, RA1, RA2, RA3 and RA4 in Table 21 are substituents in the following general formula (76).

TABLE 21

(76)

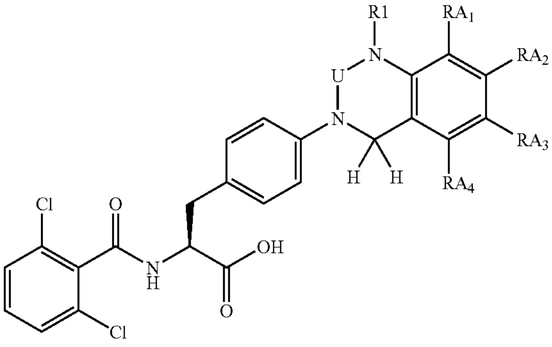

| Ref. Exam. | U | R1 | RA1 | RA2 | RA3 | RA4 | MS Found (MH+) |
|---|---|---|---|---|---|---|---|
| 147 | CO | Me | H | H | H | H | 498,500 |
| 148 | CS | Me | H | H | H | H | 514,516 |
| 149 | CO | H | H | H | H | H | 484,486 |
| 150 | CO | H | H | H | H | F | 502,504 |
| 151 | CO | Et | H | H | H | H | 512,514 |
| 152 | CO | n-Pr | H | H | H | H | 526,528 |
| 153 | CO | n-Bu | H | H | H | H | 540,542 |
| 154 | CO | iso-Pr | H | H | H | H | 526,528 |
| 155 | CO | iso-Bu | H | H | H | H | 540,542 |
| 156 | CO | sec-Butyl | H | H | H | H | 540,542 |
| 157 | CO | 2-Phenylethyl | H | H | H | H | 588,590 |
| 158 | CO | Benzyl | H | H | H | H | 574,576 |
| 159 | CO | 2,6-DifluoroBenzyl | H | H | H | H | 610,612 |

Reference Example 160

Synthesis of (2S)-2-amino-3-[4-(1-methyl-2,4-dioxo-1,3-dihydroquinazoline-3-yl)phenyl]propionic Acid Methylester Hydrochloride Process 1 Synthesis of 4-nitrophenylalanine Methylester Hydrochloride 1.49 ml of thionylchloride and 25 ml of methanol were mixed, cooled by dry-ice-acetonitrile bath and 2 g of Boc-Phe(4-NO2)—OH was added thereto. After stirring it for 1 hour and removing the bath, the solution was warmed up till room temperature and further stirred for 2.5 hours. The reaction solvent was concentrated under reduced pressure to obtain 1.83 g of the intended compound as white powder.

MS(ESI MH+): 225

CHNO: C10H12N2O4 HCl

Process 2 Synthesis of N-tertiary butyloxycarbonyl-4-nitrophenylalanine Methylester 521 mg of 4-nitrophenylalanine methylester hydrochloride obtained in Process 1 was dissolved in the solution of 554 μl of triethylamine in 10 ml of tetrahydrofuran and 480 mg of $(Boc)_2O$ was added thereto under being cooled with ice. The ice bath was removed 5 minutes later and the solution was stirred for 4.5 hours. The ethyl acetate (15 ml) was added to the reaction solvent and washed with 10% aqueous solution of citric acid, water and saturated NaCl aqueous solution respectively. After drying the ethyl acetate layer, the solution was concentrated under reduced pressure to obtain 735 mg of the intended compound.

MS(ESI MH+): 325

CHNO: C15H20N2O6

Process 3 Synthesis of (2S)-2-tertiary butyloxycarbonylamino-3-(4-aminophenyl)propionic Acid Methylester.

648 mg of N-tertiary butyloxycarbonyl-4-nitrophenylalanine methylester obtained in Process 2 was dissolved in 20 ml of ethanol and 150 mg of 5% Pd/C was added and the solution was stirred at room temperature for 18 hours under hydrogen atmosphere (1 atm). After the Celite filtration, the obtained product was purified by silica gel column (hexane:ethyl acetate; 4:1→2:1) to obtain 441 mg of the intended compound.

MS(ESI MH+): 295

CHNO: C15H22N2O4

Process 4 Synthesis of (2S)-2-tertiary butyloxycarbonylamino-3-[4-(2,4-dioxo-1,3-dihydroquinazoline-3-yl)phenyl]propionic Acid Methylester 683 mg of (2S)-2-tertiary butyloxycarbonylamino-3-(4-aminophenyl)propionic acid methylester obtained in Process 3 was dissolved in 20 ml of acetonitrile and 412 mg of methyl 2-isocyanobenzoate was added and stirred at 70° C. for 16.5 hours. After cooling down to room temperature, the produced powder was picked up by filtration and dried to obtain 588 mg of the intended compound as white powder.

MS(ESI MH+): 440

CHNO: C23H25N3O6

Process 5 Synthesis of (2S)-2-tertiary butyloxycarbonylamino-3-[4-(1-methyl-2,4-dioxo-1,3-dihydroquinazoline-3-yl)phenyl]propionic Acid Methylester 1.0 g of (2S)-2-tertiary butyloxycarbonylamino-3-[4-(2,4-dioxo-1,3-dihydroquinazoline-3-yl)phenyl]propionic acid methylester obtained in Process 4 was dissolved in 20 ml of N,N-dimethylformamide and 378 mg of potassium carbonate and 0.284 ml of iodomethane were added and stirred for 1 hour. 70 ml of ethyl acetate was further added to the reaction solvent and washed with water and saturated NaCl solution. After drying the ethyl acetate layer the solvent was concentrated under reduced pressure to obtain 1.04 g of the intended compound as yellow powder.

MS(ESI MH+): 454

CHNO: C24H27N3O6

Process 6 Synthesis of (2S)-2-amino-3-[4-(1-methyl-2,4-dioxo-1,3-dihydroquinazoline-3-yl)phenyl]propionic Acid Methylester Hydrochloride 500 mg of (2S)-2-tertiary butyloxycarbonylamino-3-[4-(1-methyl-2,4-dioxo-1,3-dihydroquinazoline-3-yl)phenyl]propionic acid methylester obtained in Process 5 was dissolved in 11 ml of 4N hydrochloric acid-dioxan solution and stirred at room temperature for 1 hour. The reaction solvent was concentrated under reduced pressure to obtain 426 mg of the intended compound as white powder.

MS(ESI MH+): 354

CHNO: C19H19N3O4HCl

Reference Example 161

Synthesis of the Compound of the Following General Formula (77) which has a Substituent(s) of Reference Example 161 of Table 22

The mixture of 88.2 mg of 2-chloro-6-methyl benzoic acid, 99.1 mg of 1-(3-dimethylaminopropyl)-3-ethylcarbodiimide hydrochloride, 79.1 mg of 1-hydroxybenzotriazole.monohydrate, 107 μl of triethylamine, 100 mg of (2S)-2-amino-3-[4-(1-methyl-2,4-dioxo-1,3-dihidroquinazoline-3-yl)phenyl] propionic acid methylester hydrochloride and 1 ml of dichloromethane was stirred at 45° C. overnight. The mixture was purified respectively by silica gel chromatography (hexane-ethyl acetate) and reverse phase HPLC to obtain the intended compound.

MS(ESI MH+): 506

CHNO: C27H24N3O5Cl

Reference Example 162

Synthesis of the Compound of the Following General Formula (77) which has a Substituent(s) of Reference Example 162 of Table 22

The mixture of 20 mg of methylester compound obtained in Reference Example 161, 2 mg of lithium hydroxide-monohydrate, 1 ml of tetrahydrofuran and 0.2 ml of water was stirred at room temperature for 1 hour. After 1M hydrochloric acid was added and the solution was neutralized, the solvent was evaporated. The intended compound (6.0 mg) was obtained by purifying with reverse phase HPLC.

MS(ESI MH+): 492

CHNO: C26H22N3O5Cl

Reference Examples 163, 166, 168, 170, 172, 174 and 176

Synthesis of the Compound of the General formula (77) which has a Substituent(s) of the Corresponding Reference Example of Table 22

The intended compound was obtained in the same manner as that of Reference Example 161 except that 2-chloro-6-methyl benzoic acid was replaced with a corresponding carboxylic acid in the synthesizing process of Reference Example 161. See Table 22.

Reference Examples 164, 165, 167, 169, 171, 173 and 175

Synthesis of the Compound of the General formula (77) which has a Substituent(s) of the Corresponding Reference Example of Table 22

The intended compound was obtained in the same manner as that of Reference Example 162 except that a corresponding methylester compound obtained in the above Reference Examples was used. See Table 22.

Reference Example 177

Synthesis of the Compound of the General Formula (77) which has a Substituent(s) of the Corresponding Reference Example of Table 22

A methylester compound was obtained in the same manner as that of Reference Example 161 except that 2-chloro-6-methyl benzoic acid was replaced with a 2,6-dichlorocinnamic acid in the synthesizing process of Reference Example 161. Then the intended compound was obtained in the same manner as that of Reference Example 162 except that the above resulting methylester was used. See Table 22.

TABLE 22

(77)

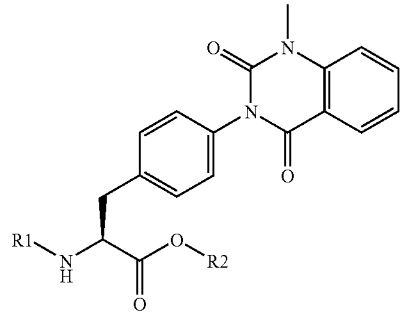

| Ref. Example | R1— | R2— | MS Found |
|---|---|---|---|
| 161 | 2-chloro-6-methylbenzoyl | Me | 506 (MH+) |
| 162 | 2-chloro-6-methylbenzoyl | H | 492 (MH+) |
| 163 | 2-chloro-6-trifluoromethylbenzoyl | Me | 560 (MH+) |
| 164 | 2-chloro-6-trifluoromethylbenzoyl | H | 544 (MH−) |
| 165 | 2-chloro-6-bromobenzoyl | H | 556 (MH+) |
| 166 | 2-chloro-6-bromobenzoyl | Me | 570 (MH+) |
| 167 | 2-chloro-6-fluorobenzoyl | H | 496 (MH+) |
| 168 | 2-chloro-6-fluorobenzoyl | Me | 510 (MH+) |
| 169 | 3,5-dichloroisonicotinoyl | H | 513 (MH+) |
| 170 | 3,5-dichloroisonicotinoyl | Me | 527 (MH+) |
| 171 | 2,6-dichloro-3-methylbenzoyl | H | 526 (MH+) |
| 172 | 2,6-dichloro-3-methylbenzoyl | Me | 540 (MH+) |
| 173 | 2,4,6-trichlorobenzoyl | H | 546 (MH+) |
| 174 | 2,4,6-trichlorobenzoyl | Me | 560 (MH+) |
| 175 | 2,6-dichloro-3-nitrobenzoyl | H | 557 (MH+) |
| 176 | 2,6-dichloro-3-nitrobenzoyl | Me | 588 (M + NH4+) |
| 177 | 2,6-dichlorocinnamoyl | H | 538 (MH+) |

Reference Example 178

Synthesis of the Compound of the Following General Formula (78) which has a Substituent(s) of Reference Example 178 of Table 23

Process 1 2-nitrosulfonylation, Methylation

The resin obtained in Process 1 of Reference Example 104 was 2-nitrosulfonylated and methylated in accordance with Reference Example 147.

Process 2 Removal of 2-nitrosulfonyl Group

The resin obtained in Process 1 was treated in accordance with Process 2 of Reference Example 135 and 2-nitrosulfonyl group was removed. The intended compound was obtained in accordance with Process 7 of Reference Example 1.

MS(ESI MH+): 541

CHNO: C26H22Cl2N4O5

Reference Example 179

Synthesis of the Compound of the Following General Formula (78) which has a Substituent(s) of Reference Example 179 of Table 23

The intended compound was obtained in the same manner as that of Reference Example 178 except that ethyl bromide was used in Process 1 of Reference Example 178.

MS(ESI MH+): 555

CHNO: C27H24Cl2N4O5

Meanwhile, R in Table 23 is a substituent of the following general formula (78).

TABLE 23

(78)

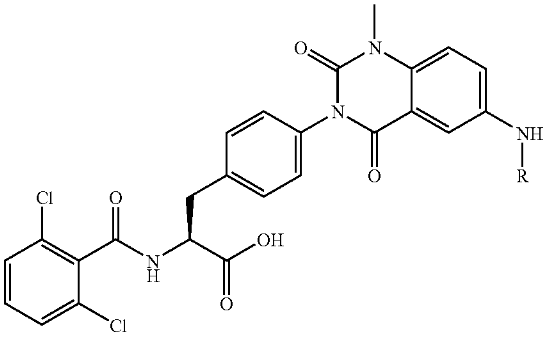

| Ref. Example | R— | MS Found (MH+) |
|---|---|---|
| 178 | methyl | 541 |
| 179 | ethyl | 555 |

Reference Examples 180 to 189

The compounds in Table 24 below were synthesized in the same manners as those of Reference Example 45 except that respective corresponding substituted 2-nitrobenzoic acid was used in Process 1 of Reference Example 45, and Process 6 and 7 of Reference Example 1. Meanwhile, R1, R2, R3 and R4 in Table 24 are substituents of the following general formula (79).

TABLE 24

(79)

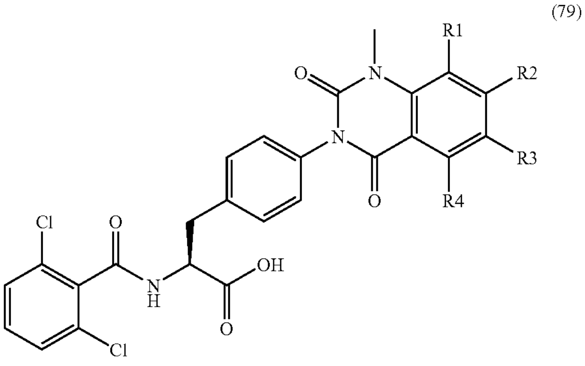

| Ref. Exam. | R1— | R2— | R3— | R4— | MS Found (MH+) |
|---|---|---|---|---|---|
| 180 | methoxy | H | H | H | 542 |
| 181 | H | H | H | methyl | 526 |
| 182 | chloro | H | H | H | 546 |
| 183 | H | H | chloro | H | 546 |
| 184 | H | H | methoxy | H | 542 |
| 185 | H | trifluoromethyl | H | H | 580 |
| 186 | methyl | H | H | H | 526 |
| 187 | H | H | H | chloro | 546 |
| 188 | H | methoxy | methoxy | H | 572 |
| 189 | H | H | fluoro | H | 530 |

NMR data of the compound of Reference Example 180: $^1$H-NMR(CDCl3) δ=3.22-3.48 (2H, m), 3.83 (3H, s), 3.93 (3H, s), 5.16-5.23 (1H, m), 7.16 (2H, d, J=7.8 Hz), 7.19-7.34 (6H, m), 7.44 (2H, d, J=8.7 Hz), 7.84 (1H, dd, J=2.4, 6.6 Hz)

Reference Example 190

Synthesis of the Compound of the Following General Formula (80) which has a Substituent(s) of Reference Example 190 of Table 25

The compound (3.2 mg) of the general formula (23) that has a substituent of Reference Example 1 in Table 1 was suspended in a mixed solution of methanol (73 μl) and toluene (224 μl) and a hexane solution of 2M trimethylsilyldiazomethane (73 μl) was added thereto. After 30 minutes, the reaction solvent was concentrated under reduced pressure to obtain 3 mg of the intended compound.

MS(ESI MH+): 526

CHNO: C26H21Cl2N3O5

Reference Example 191

Synthesis of the Compound of the Following General Formula (80) which has a Substituent(s) of Reference Example 191 of Table 25

The compound (72.7 mg) of the general formula (79) that has a substituent of Reference Example 183 in Table 24 was dissolved in a mixed solution of dichloromethane (10 ml) and isopropanol (0.2 ml). 1-(3-dimethylaminopropyl)-3-ethylcarbodiimide hydrochloride (26 mg) and 4-dimethylaminopyridine (26.2 mg) were added and stirred. After stirring it for 18 hours, 1N hydrochloric acid was added and the solution was extracted with ethyl acetate. The water layer was further extracted with ethyl acetate and mixed with the previously extracted layer, and washed with saturated solution of sodium hydrogencarbonate and saturated NaCl aqueous solution.

Then, the organic layer was dried with anhydrous sodium sulphate and concentrated under reduced pressure. The obtained product was purified by high pressure liquid chromatography (water-acetonitrile) to obtain 10 mg of the intended compound.

MS(ESI MH+): 588

CHNO: C28H24Cl3N3O5

Reference Example 192

Synthesis of the Compound of the Following General Formula (80) which has a Substituent(s) of Reference Example 192 of Table 25

The compound (12 mg) of the general formula (37) that has a substituent of Reference Example 111 in Table 16 was dissolved in methanol (0.5 ml), cooled down to −78° C. and thionyl chloride (0.04 ml) was added. After stirring it at room temperature for 7.5 hours, the reaction solvent was concentrated under reduced pressure to obtain 12 mg of the intended compound.

MS(ESI MH+): 597

CHNO: C30H30Cl2N4O5

Reference Examples 193 to 202

The compounds shown below were synthesized by using a carboxylic acid described in respective corresponding Reference Example as a starting material. In this connection, Reference Examples 193 to 195 and 201 were synthesized in the same manner as that of Reference Example 191 except that a suitable alcohol was used. Reference Example 196 to 200 and 202 were synthesized in the same manner as that of Reference Example 192. Meanwhile, R1, R2 and R3 in Table 25 are substituents of the following general formula (80).

TABLE 25

(80)

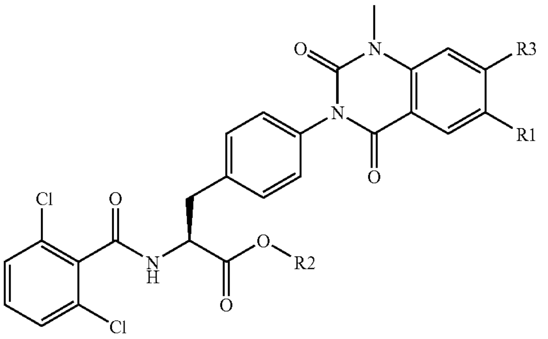

| Ref. Example | R1— | R2— | R3— | MS Found (MH+) |
|---|---|---|---|---|
| 190 | H | methyl | H | 526 |
| 191 | chloro | isopropyl | H | 588 |
| 192 | diethylamino | methyl | H | 597 |
| 193 | H | ethyl | H | 540 |
| 194 | H | isopropyl | H | 554 |
| 195 | methoxy | ethyl | H | 570 |
| 196 | dimethylamino | methyl | H | 569 |
| 197 | ethylamino | methyl | H | 569 |
| 198 | methylamino | methyl | H | 555 |
| 199 | ethylmethylamino | methyl | H | 583 |
| 200 | amino | methyl | H | 541 |
| 201 | chloro | ethyl | H | 574 |
| 202 | H | methyl | fluoro | 544 |

NMR data of the compound of Reference Example 196: $^{1}$H-NMR (400 MHz, DMSO-$d_6$) δ 2.94 (3H, m), 3.02 (1H, m), 3.22 (1H, m), 3.58 (3H, s), 3.70 (3H, s), 4.82 (1H, m), 7.18-7.47 (10H, m), 9.28 (1H, d). $^{13}$C-NMR (100 MHz, DMSO-$d_6$) δ 30.88, 36.37, 40.75, 52.28, 53.66, 109.17, 116.00, 116.22, 121.35, 128.32, 128.99, 129.88, 131.36, 131.79, 132.07, 135.35, 136.35, 137.21, 146.74, 150.37, 161.89, 163.99, 171.72.

Reference Example 203

Synthesis of the Compound of the Following General Formula (81)

Process 1 Acylation

The resin obtained in Process 4 of Example 1 was acylated by using cis-2-[(9-fluorenylmethyloxycarbonyl)amino]-1-cyclohexan carboxylic acid (274 mg), DIC (0.058 ml), HOAt (101 mg) and NMP (2.5 ml).

Process 2 Removal of 9-fluorenylmethyloxycarbonyl Group

The resin obtained in Process 1 was stirred in 20% piperidine-NMP solution for ten minutes twice and washed with NMP, methanol and dichloromethane four times each.

Process 3 Cyclization, Cleavage from Resin

The resin obtained in Process 2 was treated in the same way as that of Process 2 of Reference Example 96 and then treated in accordance with Process 7 of Reference Example 1 to obtain the intended compound.

MS(ESI MH+): 504

CHNO: C24H23Cl2N3O5

(81)

(cis)

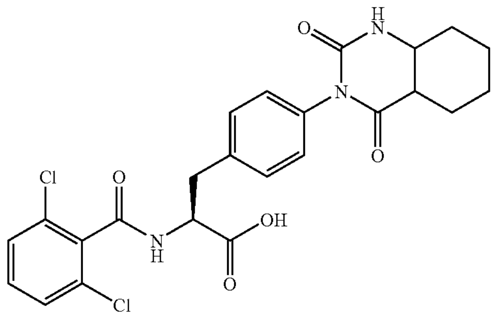

Reference Examples 205 and 206

The compounds of the following general formula (82) that has a substituent in Table 26 were synthesized by using a carboxylic acid obtained in Reference Example 108 as a starting material and in the same manner as that of Reference Example 191 except that a suitable alcohol was used. Meanwhile, R in Table 26 is a substituent of the following general formula (82).

TABLE 26

(82)

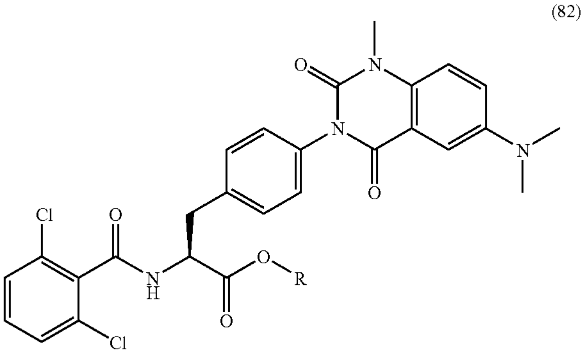

| Ref. Example | R— | MS Found (MH+) |
|---|---|---|
| 205 | ethyl | 583 |
| 206 | isopropyl | 597 |

Reference Examples 207 and 208

The compounds of the following general formula (83) that has substituents in Table 27 were synthesized in the same manner as that of Reference Example 149 except that respective corresponding substituted 2-nitrobenzylbromide was used. Meanwhile, R1 and R2 in Table 27 are substituents of the following general formula (83).

TABLE 27

(83)

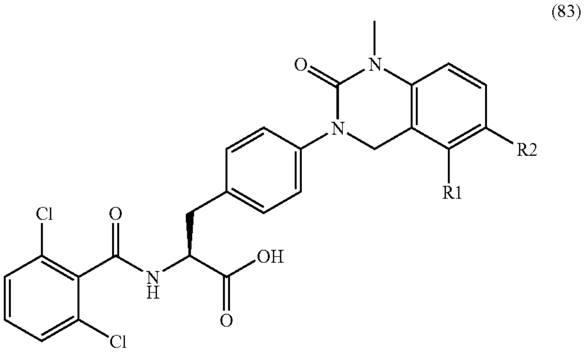

| Ref. Example | R1— | R2— | MS Found (MH+) |
|---|---|---|---|
| 207 | —H | methyl | 512 |
| 208 | fluoro | —H | 516 |

Reference Example 209

The compound of the following general formula (84) that has a substituent of Reference Example 209 in Table 28 was synthesized in the same manners as those of Reference Example 45 except that 3-chloro-2-nitrobenzoic acid was replaced with 1-ethyl-4-nitro-1H-pyrazole-3-carboxylic acid in Process 1 of Reference Example 45, and Process 6 and 7 of Reference Example 1. Meanwhile, R in Table 28 is a substituent of the following general formula (84).

Reference Example 210

The compound of the following general formula (84) that has a substituent of Reference Example 210 in Table 28 was synthesized by using the compound obtained in Reference Example 209 as a starting material and in the same manner as that of Reference Example 192. Meanwhile, R in Table 28 is a substituent of the following general formula (84).

TABLE 28

(84)

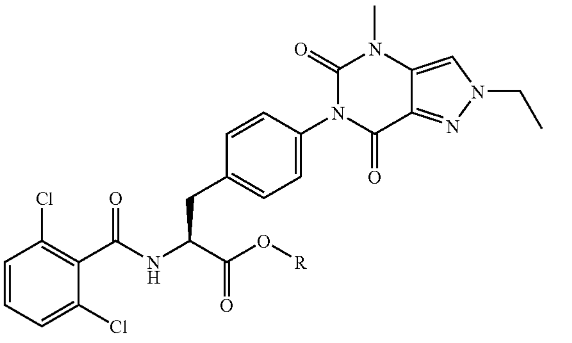

| Ref. Example | R— | MS Found (MH+) |
|---|---|---|
| 209 | H | 530 |
| 210 | methyl | 544 |

Reference Example 211

The compound of the following general formula (85) was synthesized as follows. The compound of the general formula (23) that has a substituent(s) of Reference Example 1 in Table 1 (28.9 mg) was dissolved in DMF (1 ml) and 1-(3-dimethylaminopropyl)-3-ethylcarbodiimide hydrochloride (12.9 mg), 1-hydroxy-7-azabenzotriazole (10.7 mg), hydroxylamine hydrochloride (11.5 mg) and N-methylmorpholine (9.1 mg) were added and stirred. Further, 1-(3-dimethylaminopropyl)-3-ethylcarbodiimide hydrochloride (11.7 mg), 1-hydroxy-7-azabenzotriazole (8.2 mg), hydroxylamine hydrochloride (9.5 mg), N-methylmorpholine (10.5 mg) and DMF (0.5 ml) were added and stirred. Two hours later, water was added to the reaction solvent and the separated crystal was dried to 14.8 mg of the intended compound.

MS(ESI MH−): 525

CHNO: C25H20Cl2N4O5

(85)

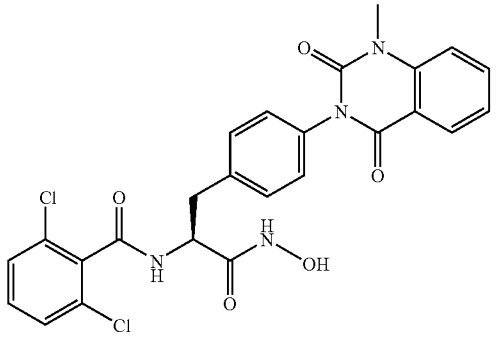

Reference Example 212

Synthesis of the Compound of the Following General Formula (86) which has a Substituent(s) of Reference Example 212 of Table 29

Process 1 Synthesis of (2S)-2-(t-butoxycarbonylamino)-3-[4-(1-methyluracil-3-yl)phenyl]propionic Acid Methylester The mixture of 30 mg of (2S)-2-(t-butoxycarbonylamino)-3-[4-(dihydroxy boranyl)phenyl]propionic acid, 25 mg of 1-methyluracil, 27 mg of copper acetate(II), 40 mg of triethylamine and 4 ml of dichloromethane were stirred overnight. The reaction solvent was diluted by ethanol and filtered by Celite filtration. The residual material obtained by concentrating the filtrate was dilluted by 1N sodium hydrate and washed with ethyl acetate. After making the water layer acidic by hydrochloric acid, the solution was extracted with ethyl acetate, washed with saturated NaCl aqueous solution, dried with magnesium sulfate and the solvent was removed to obtain a crude material of (2S)-2-(t-butoxycarbonylamino)-3-[4-(1-methyluracil-3-yl)phenyl]propionic acid. This crude material was diluted by 5 ml of ethanol and hexane solution including 2M trimethylsilyldiazomethane was added to give methyl ester. The reaction solvent was concentrated and purified by silica gel chromatography (ethyl acetate-ethanol) to obtain the title compound (7 mg).

MS(ESI MH+): 404

$^1$H-NMR (DMSO-d6) δ 1.45 (9H, s), 3.15 (2H, d), 3.40 (3H, s), 3.70 (3H, s), 4.60 (1H, m), 5.00 (1H, m), 5.85 (1H, d), 7.15 (2H, d), 7.20 (1H, d), 7.30 (2H, d)

Process 2 Synthesis of (2S)-2-(2,6-dichlorobenzoylamino)-3-[4-(1-methyluracil-3-yl)phenyl]propionic Acid Methylester 6 ml of dioxan solution including 4N hydrogen chloride was added to 86 mg of (2S)-2-(t-butoxycarbonylamino)-3-[4-(1-methyluracil-3-yl)phenyl]propionic acid methylester and stirred for 1 hour. 10 ml of dimethylformamide, 62 μl of triethylamine and 34 μl of 2,6-dichloromenzoyl chloride were added to the residual material obtained by removing the solvent and stirred for 30 minutes. The reaction solvent was diluted by ethyl acetate, washed with 1N hydrochloric acid, an aqueous solution of saturated sodium hydrogen carbonate and saturated NaCl aqueous solution, and dried with magnesium sulfate and the solvent was removed to obtain a crude material of the title compound. The crude material was purified by reverse phase HPLC to obtain the title compound (26 mg).

MS(ESI MH+): 476

H-NMR (CDCl3) δ 3.30 (2H, br), 3.40 (3H, s), 3.75 (3H, s), 5.25 (1 H, q), 5.85 (1H, d), 6.40 (1H, d) 7.15 (2H, d), 7.20-7.40 (6H, m)

Reference Example 213

Synthesis of the Compound of the Following General formula (86) which has a Substituent(s) of Reference Example 213 of Table 29

The mixture of 10 mg of (2S)-2-(2,6-dichlorobenzoylamino)-3-[4-(1-methyluracil-3-yl)phenyl]propionic acid methylester, 3 ml of dioxan solution including 4N hydrogen chloride and 3 ml of water were stirred at 80° C. for 4 hours. After the solvent was removed, the crude material was purified by reverse phase HPLC to obtain the said compound (3 mg).

MS(ESI MH+): 462

TABLE 29

(86)

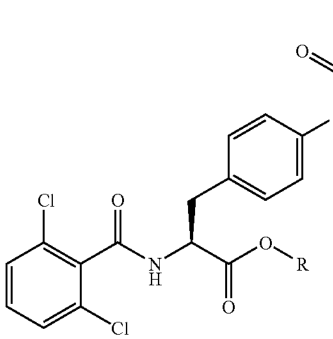

| Ref. Example | R— | MS Found (MH+) |
|---|---|---|
| 212 | methyl | 476 |
| 213 | —H | 462 |

Reference Example 214

2-chloro-6-trifuluoromethylbenzoic Acid

The mixture of 500 mg of 3-chlorobenzotrifuluoride and 3 ml of tetrahydrofuran was cooled down to −50° C. and 2 ml of 1.6M n-butyllithium hexan solution was added and stirred for 1 hour. The mixture was put into dry ice and diluted by an aqueous solution of 1N sodium hydroxide. After washing it with toluene, the water layer was made acidic by hydrochloric acid and extracted with ethyl acetate. The crude material obtained by removing the solvent was purified by reverse phase HPLC to the said compound.

Yield 244 mg

H-NMR (DMSO-d6) δ 7.68 (1H, t), 7.80 (1H, d), 7.88 (1H, d).

MS (ESI, m/z) 223 (M−H)−

Reference Example 215

2-bromo-6-chlorobenzoic Acid

The mixture of 500 mg of 3-bromochlorobenzen and 3 ml of tetrahydrofuran was cooled down to −78° C. and 1.3 ml of 2.0M lithiumdiisopropylamide heptane/tetrahydrofuran/ethylbenzene was added. After stirring it for 2 hours, the mixture was put into dry ice and washed and extracted as described in Referencial Example 1 to obtain a crude material. The crude material was washed with a mixed solvent of hexane-ethyl acetate to obtain the said compound.

Yield 317 mg

H-NMR (DMSO-d6) δ 7.40 (1H, t), 7.60 (1H, d), 7.70 (1H, d).

MS (ESI, m/z) 233 (M−H)−

(77)

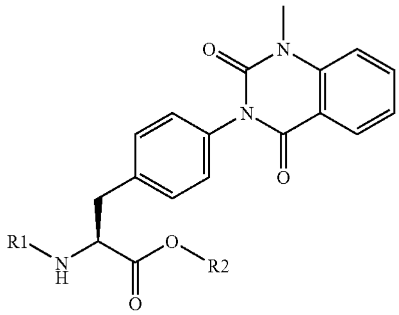

Reference Test Example 1

Assessment of VCAM-1/α4β1 Binding Antagonist Activity

The capacity of a test substance antagonistic to the binding of cell strain Jurkat (ATCC TIB-152) of human T cells, known to express integrin α4β1, to VCAM-1 was determined.

100 μl/well of a solution (500 ng/ml) of recombinant human VCAM-1 (R & D systems) solution diluted with buffer A (0.1 M $NaHCO_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to 1/4 concentration was added in an amount of 150 μl/well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 μg/ml of Calcein-AM (Wako Pure Chemical Industries, Ltd.) at 37° C. in dark place for 30 minutes to label with fluorescence. The cells were again suspended in a binding buffer (20 mM HEPES, DMEM containing 0.1% BSA).

50 μl of a test substance of various concentrations obtained by the dilution with the binding buffer was added to the plate. Immediately thereafter, 50 μl (final volume: 100 μl/well) of the fluorescent Jurkat cells ($4\times10^6$ cells/ml) were added thereto, and they were incubated in dark place at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

The obtained test results are shown in Table 31.

Reference Test Example 2

Assessment of VCAM-1/α4β7 Binding Antagonistic Activity

The capacity of a test substance antagonistic to the binding of lymphoma cell strain RPMI-8866 of human B cells, known to express integrin α4β7, to VCAM-1 was determined.

100 μl/well of a solution (500 ng/ml) of recombinant human VCAM-1 (R & D systems) solution diluted with buffer A (0.1 M $NaHCO_3$, pH 9.6) was added to a micro titer plate having 96 wells (Nunc Maxisorp). After the incubation at 4° C. overnight, unbound VCAM-1 was removed by washing once with PBS. After completion of the washing, a buffer (buffer B) obtained by diluting Block Ace (Dainippon Pharmaceutical Co., Ltd.) with PBS to 1/4 concentration was added in an amount of 150 μl/well. After the incubation at room temperature for 1 hour, buffer B was removed and the plate was washed with PBS once.

RPMI-8866 cells were washed with DMEM twice and incubated in Dulbecco modified Eagle medium containing 10 μg/ml of Calcein-AM (Wako Pure Chemical Industries, Ltd.) (SIGMA, hereinafter referred to as "DMEM") in dark place at 37° C. for 30 minutes to label with fluorescence. The cells were again suspended in a binding buffer (20 mM HEPES, DMEM containing 0.1% BSA) containing 4 mM of $MnCl_2$.

50 μl of a test substance of various concentrations obtained by the dilution with the binding buffer was added to the plate. Immediately thereafter, 50 μl (final volume: 100 μl/well) of the fluorescent RPMI-8866 cells ($4\times10^6$ cells/ml) were added thereto, and they were incubated in dark place at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration $IC_{50}$ for the 50% binding inhibition was calculated.

The obtained test results are shown in Table 31.

TABLE 31

Results of the determination of integrin VCAM/α4 binding antagonistic activity (IC50, nmol/L)

| Reference Example | α4β7 | α4β1 |
|---|---|---|
| 1 | 1.0 | 18 |
| 2 | 9.2 | 240 |
| 3 | 3.5 | 66 |
| 4 | 2.8 | 26 |
| 5 | 14.0 | 46 |
| 6 | 3.3 | 80 |
| 7 | 22.0 | 110 |
| 8 | 3.9 | 94 |
| 9 | 94.0 | 440 |
| 11 | 74.0 | 6200 |
| 12 | 19.0 | 490 |

TABLE 31-continued

Results of the determination of integrin VCAM/α4 binding antagonistic activity (IC50, nmol/L)

| Reference Example | α4β7 | α4β1 |
|---|---|---|
| 13 | 4.5 | 220 |
| 14 | 26.0 | 1260 |
| 16 | 14.0 | 1700 |
| 17 | 43.0 | 2100 |
| 18 | 23.0 | 1900 |
| 23 | 18.0 | 7240 |
| 31 | 50.0 | 630 |
| 32 | 64.0 | 2420 |
| 34 | 42.0 | 2210 |
| 35 | 68.0 | 1700 |
| 36 | 6.6 | 490 |
| 37 | 19.0 | 200 |
| 41 | 86.0 | 3410 |
| 42 | 92.0 | 6730 |
| 44 | 79.0 | 4230 |
| 45 | 10.2 | 340 |
| 46 | 6.8 | 195 |
| 47 | 76.0 | 1980 |
| 48 | 28.0 | 1800 |
| 49 | 62.1 | 1180 |
| 50 | 7.9 | 1770 |
| 51 | 30.0 | 1180 |
| 52 | 55.3 | 1310 |
| 53 | 66.1 | 2460 |
| 54 | 9.8 | 71 |
| 57 | 29.9 | 639 |
| 58 | 31.6 | 1070 |
| 59 | 35.8 | 540 |
| 60 | 36.1 | 780 |
| 61 | 42.0 | 1150 |
| 62 | 45.0 | 1450 |
| 63 | 1.3 | 28 |
| 65 | 7.0 | 330 |
| 66 | 1.3 | 170 |
| 67 | 2.2 | 370 |
| 68 | 1.5 | 350 |
| 69 | 2.5 | 5630 |
| 70 | 3.5 | 34 |
| 71 | 11.0 | 185 |
| 72 | 2.6 | 27 |
| 73 | 1.6 | 27 |
| 74 | 2.5 | 53 |
| 75 | 2.3 | 60 |
| 76 | 13.0 | 192 |
| 78 | 9.6 | 180 |
| 79 | 18.0 | 440 |
| 80 | 74.0 | 960 |
| 81 | 8.6 | 72 |
| 84 | 20.0 | 158 |
| 85 | 25.0 | 230 |
| 89 | 2.7 | 41 |
| 90 | 43.7 | 511 |
| 91 | 1.6 | 1200 |
| 92 | 5.7 | 1340 |
| 93 | 4.8 | 4030 |
| 94 | 6.0 | 1150 |
| 95 | 1.8 | 960 |
| 97 | 13.0 | 1500 |
| 99 | 2.0 | 12 |
| 100 | 2.4 | 11 |
| 104 | 1.4 | 16 |
| 105 | 0.8 | 14 |
| 106 | 2.8 | 44 |
| 107 | 1.1 | 17 |
| 108 | 3.3 | 57 |
| 109 | 4.3 | 56 |
| 110 | 4.1 | 55 |
| 111 | 11.0 | 88 |
| 112 | 1.1 | 37 |
| 113 | 1.6 | 52 |
| 114 | 27.0 | 190 |
| 115 | 36.0 | 760 |
| 116 | 35.0 | 450 |

TABLE 31-continued

| Results of the determination of integrin VCAM/α4 binding antagonistic activity (IC50, nmol/L) | | |
|---|---|---|
| Reference Example | α4β7 | α4β1 |
| 117 | 19.0 | 480 |
| 118 | 16.0 | 385 |
| 119 | 21.0 | 440 |
| 120 | 24.0 | 500 |
| 121 | 14.0 | 109 |
| 122 | 0.6 | 310 |
| 123 | 12.0 | 180 |
| 124 | 20.0 | 840 |
| 126 | 70.0 | 1580 |
| 129 | 76.4 | 2023 |
| 131 | 24.0 | 183 |
| 135 | 12.0 | 570 |
| 136 | 3.0 | 565 |
| 137 | 11.2 | 2120 |
| 139 | 17.0 | 107 |
| 142 | 9.0 | 210 |
| 147 | 6.5 | 107 |
| 162 | 0.2 | 34 |
| 164 | 7.1 | 120 |
| 165 | 0.6 | 11 |
| 169 | 0.5 | 6 |
| 180 | 5.4 | 86 |
| 181 | 1.0 | 15 |
| 182 | 6.2 | 113 |
| 183 | 1.7 | 25 |
| 184 | 3.3 | 31 |
| 185 | 2.7 | 12 |
| 186 | 4.3 | 59 |
| 187 | 3.2 | 26 |
| 188 | 2.7 | 11 |
| 189 | 1.1 | 18 |
| 211 | 20 | 250 |

What is claimed is:

1. A phenylalanine compound of the following formula (1) or a pharmaceutically acceptable salt thereof:

(1)

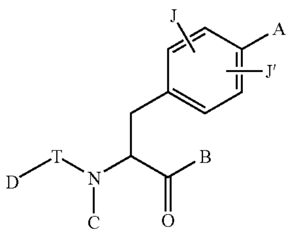

wherein A is a group represented by formula (3-3'): or (3-4):

(3-3')

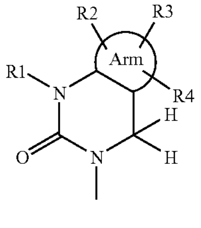

-continued (3-4)

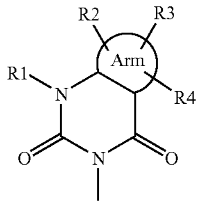

wherein Arm represents a benzene ring

R1, R2, R3, and R4 may be the same or different from one another and each represent a hydrogen atom, a halogen atom, a hydroxyl group, a lower alkyl group, a substituted lower alkyl group, a lower alkenyl group, a substituted lower alkenyl group, a lower alkynyl group, a substituted lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof, a lower alkyl group substituted with an aryl group(s), a lower alkyl group substituted with a heteroaryl group(s), a lower alkoxyl group, a lower alkylthio group, a lower alkoxyl group and lower alkylthio group substituted with a cycloalkyl group(s) which may contain a hetero atom(s) in the ring thereof, a lower alkoxyl group and lower alkylthio group substituted with an aryl group(s), a lower alkoxyl group and lower alkylthio group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkylthio group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylsulfonyl group, a substituted or unsubstituted sulfamoyl group or an ammonium group, B represents an organic group represented by the following formula (B-1) or (B-2), a substituted or unsubstituted amino group (except for a hydroxylamino group) or a substituted or unsubstituted mercapto group,

—O—Y—E (B-1)

(B-2)

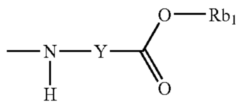

wherein Y represents a substituted or unsubstituted divalent lower hydrocarbon group, E represents a substituted or unsubstituted acyloxy group, a substituted or unsubstituted lower alkoxycarbonyloxy group, a substituted or unsubstituted amino group, carboxyl group, a substituted or unsubstituted lower alkoxycarbonyl group, a halogen atom, an aryl group, a heteroaryl group, a substituted or unsubstituted alkoxyl group or a substituted or unsubstituted carbamoyl group, Rb1 represents a hydrogen atom or a lower alkyl group, and Y and E may be bonded together to form a ring, C represents a hydrogen atom, a lower alkyl group, a lower alkenyl group, a lower alkynyl group, a lower alkyl group substituted with a cycloalkyl group(s) which may contain a hetero atom(s) in the ring thereof, a lower alkyl group substituted with an aryl group(s) or a lower alkyl group substituted with a heteroaryl group(s), D represents a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group(s) which may contain a hetero atom(s) in the ring thereof a lower alkyl group substituted with an aryl group(s), a lower alkyl group substituted with a heteroaryl group(s), a lower alkoxyl group, a lower alkoxyl group substituted with a cycloalkyl group(s) which may contain a hetero atom(s) in the ring thereof, a lower alkoxyl group substituted with an aryl group(s), a lower alkoxyl group substituted with a heteroaryl group(s), a cycloalkyloxy group which may contain a hetero atom(s) in the ring thereof, an aryloxy group, a heteroaryloxy group, a lower hydroxyalkyl group, a lower hydroxyalkenyl group, a lower hydroxyalkoxyl group, a lower halogenoalkyl group, a lower halogenoalkoxyl group, a lower halogenoalkenyl group, nitro group, cyano group, a substituted or unsubstituted amino group, carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group, C and D may be bonded together to form a ring which may contain one or two oxygen, nitrogen or sulfur atoms, T represents an interatomic bond, C(=O), C(=S), S(=O), $S(=O)_2$,N(H)-C(=O), or N(H)-C(=S), J and J' may be the same or different from each other and each represent a hydrogen atom, a halogen atom, a lower alkyl group, a lower alkyloxy group or a nitro group.

2. The phenylalanine compound or pharmaceutically acceptable salt thereof according to claim 1, wherein, in the formula (1), B represents the organic group represented by the formula (B-1) or (B-2), a substituted or unsubstituted amino group or a substituted or unsubstituted mercapto group,

—O—Y—E (B-1)

(B-2)

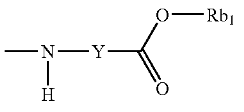

wherein Y represents a substituted or unsubstituted divalent lower hydrocarbon group, E represents a substituted or unsubstituted acyloxy group, a substituted or unsubstituted lower alkoxycarbonyloxy group, a substituted or unsubstituted amino group, carboxyl group or a substituted or unsubstituted lower alkoxycarbonyl group, $Rb_1$, represents a hydrogen atom or a lower alkyl group, and Y and E may be bonded together to form a ring.

3. A phenylalanine compound or pharmaceutically acceptable salt thereof according to claim 1, wherein, in the formula (1), B represents the organic group represented by the formula (B-1) or a substituted or unsubstituted amino group,

—O—Y-E (B-1)

wherein Y represents a substituted or unsubstituted divalent lower hydrocarbon group, E represents a substituted or unsubstituted acyloxy group, a substituted or unsubstituted lower alkoxycarbonyloxy group, a substituted or unsubstituted amino group, a halogen atom, an aryl group, a heteroaryl group, an alkoxyl group or a substituted or unsubstituted carbamoyl group.

4. The phenylalanine compound or pharmaceutically acceptable salt thereof according to claim 1, wherein, in the formula (1), B represents the group represented by the formula (B-1) or a substituted or unsubstituted amino group,

—O—Y-E (B-1)

wherein Y is a substituted or unsubstituted methylene group, a substituted or unsubstituted ethylene group or substituted or unsubstituted trimethylene group, and E is a substituted or unsubstituted acyloxy group, a substituted or unsubstituted alkoxycarbonyloxy group or a substituted or unsubstituted amino group.

5. The phenylalanine compound or pharmaceutically acceptable salt thereof according to claim 1, wherein, in the formula (1), B represents the group represented by the formula (B-1), an amino group substituted with a lower alkyl group(s) or an unsubstituted amino group,

—O—Y-E (B-1)

wherein Y is a substituted or unsubstituted methylene group, a substituted or unsubstituted ethylene group or substituted or unsubstituted trimethylene group, and E is a substituted or unsubstituted acyloxy group, a chlorine atom, a fluorine atom, a substituted or unsubstituted furyl group, a substituted or unsubstituted phenyl group, a substituted or unsubstituted thienyl group, a substituted or unsubstituted pyridyl group, a lower alkoxyl group, a carbamoyl group which may be substituted with a lower alkyl group(s), a substituted or unsubstituted lower alkoxycarbonyloxy group or a substituted or unsubstituted amino group.

6. The phenylalanine compound or pharmaceutically acceptable salt thereof according to claim 1, wherein, in the formula (1), B represents the group represented by the formula (B-1) or a substituted or unsubstituted amino group,

—O—Y-E (B-1)

wherein Y is a substituted or unsubstituted methylene group and E is a substituted or unsubstituted acyloxy group or a substituted or unsubstituted lower alkoxycarbonyloxy group, or Y is a substituted or unsubstituted ethylene group or a substituted or unsubstituted trimethylene group and E is a substituted or unsubstituted amino group, or Y is a ethylene group having an acyloxymethyl group as a substituent and E is a substituted or unsubstituted acyloxy group.

7. The phenylalanine compound or pharmaceutically acceptable salt thereof according to claim 1, wherein, in the formula (1), B represents the group represented by the formula (B-1), an amino group substituted with one lower alkyl group or an unsubstituted amino group,

—O—Y-E (B-1)

wherein Y is a methylene group substituted with a lower alkyl group(s) or unsubstituted methylene group and E is a substituted or unsubstituted lower acyloxy group, a chlorine atom, a fluorine atom, a substituted or unsubstituted furyl group, a carbamoyl group which may be substituted with a lower alkyl group(s) or a substituted or unsubstituted lower alkoxycarbonyloxy group, or Y is a substituted or unsubstituted ethylene group or a substituted or unsubstituted trimethylene group and E is a lower alkoxyl group or an amino group substituted with a lower alkyl group(s).

8. The phenylalanine compound or pharmaceutically acceptable salt thereof according to claim 1, wherein, in the formula (1), B represents the group represented by the formula (B-1), an amino group substituted with one lower alkyl group or an unsubstituted amino group,

—O—Y-E (B-1)

wherein Y is a methylene group substituted with a lower alkyl group(s) or an unsubstituted methylene group and E is a substituted or unsubstituted lower acyloxy group or a substituted or unsubstituted lower alkoxycarbonyloxy group, or Y is a substituted or unsubstituted ethylene group or a substituted or unsubstituted trimethylene group and B is an amino group substituted with a lower alkyl group(s).

9. The phenylalanine compound or pharmaceutically acceptable salt thereof according to claim 1, wherein, in the formula (1), B represents the group represented by the formula (B- 1) or an amino group substituted with one lower alkyl group,

—O—Y-E (B-1)

wherein Y is a methylene group substituted with a lower alkyl group(s) and E is an unsubstituted lower alkoxycarbonyloxy group, or Y is an unsubstituted methylene group and E is an unsubstituted lower acyloxy group, or Y is an unsubstituted ethylene group and B is a cyclic amino group.

10. The phenylalanine compound or pharmaceutically acceptable salt thereof according to claim 1, wherein, in the formula (1), B represents the group represented by the formula (B-1)

—O—Y-E (B-1)

wherein Y is an unsubstituted methylene group and E is an unsubstituted lower acyloxy group, a chlorine atom, a furyl group or dimethylcarbamoyl group, or Y is an unsubstituted ethylene group and E is a lower alkoxyl group.

11. The phenylalanine compound or pharmaceutically acceptable salt thereof according to claim 6, wherein, in the general formula (1), C represents a hydrogen atom or a lower alkyl group, J and J' represent a hydrogen group.

12. The phenylalanine compound or pharmaceutically acceptable salt thereof according to claim 3, wherein, in the general formula (1), A is a group represented by the formula (3-4)

wherein Arm is a benzene ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group.

13. The phenylalanine compound or pharmaceutically acceptable salt thereof according to claim 1, wherein, in the general formula (1), A is a group represented by the formula (3-4) wherein Arm is a benzene ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group.

14. The phenylalanine compound or pharmaceutically acceptable salt thereof according to claim 5, wherein, in the general formula (1), D represents the following formula (4-1), (4-2), (4-3) or (4-4):

(4-1)

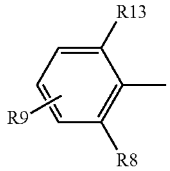

(4-2)

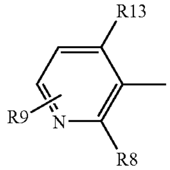

(4-3)

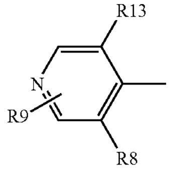

(4-4)

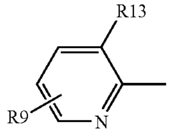

wherein R 13 represents a halogen atom or methyl group, R8 represents a halogen atom, methyl group, trifluoromethyl group, methoxy group or a hydrogen atom, R9 represents a hydrogen atom, halogen atom, hydroxyl group, lower alkyl group, cycloalkyl group which may contain a hetero atom(s) in the ring thereof, lower alkyl group substituted with a cycloalkyl group(s) which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), trialkylammonium group, methanesulfonyl amino group or tetrazolyl group, C is a hydrogen atom, each of J and J' is a hydrogen atom and T is C(=O).

15. The phenylalanine compound or pharmaceutically acceptable salt thereof according to claim 6, wherein, in the general formula (1), D represents the following formula (4-1), (4-2), (4-3) or (4-4):

(4-1)

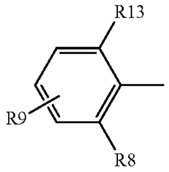

(4-2)

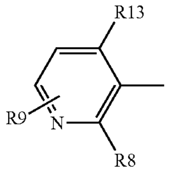

(4-3)

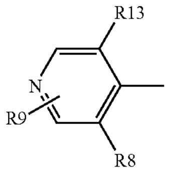

(4-4)

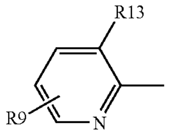

wherein R13 represents a halogen atom or methyl group, R8 represents a halogen atom, methyl group, trifluoromethyl group, methoxy group or a hydrogen atom, R9 represents a hydrogen atom, halogen atom, hydroxyl group, lower alkyl group, cycloalkyl group which may contain a hetero atom(s) in the ring thereof, lower alkyl group substituted with a cycloalkyl group(s) which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s), trialkylammonium group, methanesulfonyl amino group or tetrazolyl group, C is a hydrogen atom, each of J and J' is a hydrogen atom and T is C(=O).

16. The phenylalanine compound or pharmaceutically acceptable salt thereof according to claim 1, wherein, in the general formula (1), A is a group represented by the formula (3-4)

wherein Arm is a benzene ring, R1is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, D represents the following formula (4-1):

(4-1)

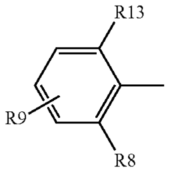

wherein 13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogeno alkoxyl group, lower halogenoalkylthio group, nitro group, cyano group, amino group, amino group substituted with a lower alkyl group(s) or trialkylammonium group, C is a hydrogen atom, each of J and J' is a hydrogen atom and T is C(=O).

17. The phenylalanine compound or pharmaceutically acceptable salt thereof according to claim 2, wherein, in the general formula (1), A is a group represented by the formula (3-4)

wherein Arm is a benzene ring, R1 is a lower alkyl group, R2, R3 and R4 may be the same or different from one another and each represent a hydrogen atom, a halogen atom, a hydroxyl group, a lower alkyl group, a cycloalkyl group which may contain a hetero atom(s) in the ring thereof, a lower alkyl group substituted with a cycloalkyl group(s) which may contain a hetero atom(s) in the ring thereof, a lower alkoxyl group, a lower alkylthio group, a lower halogenoalkyl group, a lower halogenoalkoxyl group, a lower halogenoalkylthio group, a nitro group, a cyano group, an amino group, an amino group substituted with a lower alkyl group(s) or a trialkylammonium group, D represents the following formula (4-1):

(4-1)

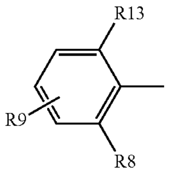

wherein R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogeno alkoxyl group, lower halogenoalkylthio group, nitro group, cyano group, amino group, amino group substituted with a lower alkyl group(s) or trialkylammonium group, C is a hydrogen atom, each of J and J' is a hydrogen atom and T is C(=O).

18. A phenylalanine compound according to claim 1, represented by the following formula:

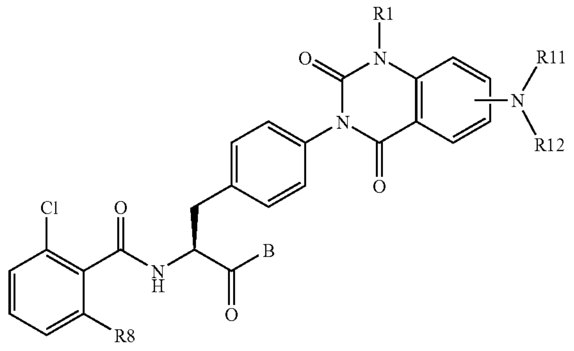

wherein R1 represents a methyl group or ethyl group, R8 represents a halogen atom or methyl group, R11and R12 may be the same or different from each other and each represents a hydrogen atom, methyl group, ethyl group or propyl group, R11 and R12 may be bonded together to form a ring, and in that case, R11-R12 represent trimethylene, tetramethylene or pentamethylene or a pharmaceutically acceptable salt thereof.

19. A phenylalanine compound according to claim 10, represented by the following formula:

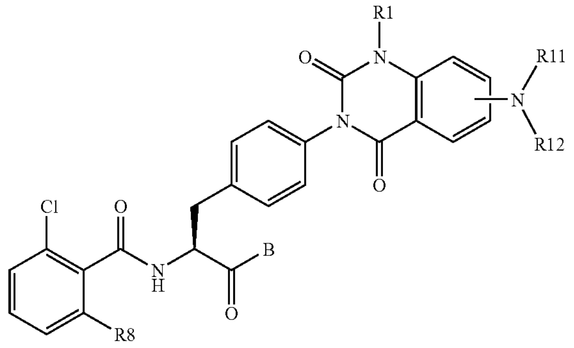

wherein R1 represents a methyl group or ethyl group, R8 represents a halogen atom or methyl group, R11 and R12 maybe the same or different from each other and each represents a hydrogen atom, methyl group, ethyl group or propyl group, R11 and R12 may be bonded together to form a ring, and in that case, R11-R12 represent trimethylene, tetramethylene or pentamethylene or a pharmaceutically acceptable salt thereof.

20. The phenylalanine compound or pharmaceutically acceptable salt thereof according to claim 1, wherein, in the general formula (1), C represents a hydrogen atom, D represents the formula (4-1) wherein R13 and R8 represent a chlorine atom, and R9 represents a hydrogen atom, halogen atom, hydroxyl group, lower alkyl group, cycloalkyl group which may contain a hetero atom(s) in the ring thereof, lower alkoxyl group, lower alkylthio group, lower halogenoalkyl group, lower halogenoalkoxyl group, lower halogenoalkylthio group, nitro group, cyano group, amino group, amino group substituted with a lower alkyl group(s) or trialkylammonium group, T is C(=O) and each of J and J' is a hydrogen atom.

21. A phenylalanine compound according to claim 1represented by the following one of the following formulae:

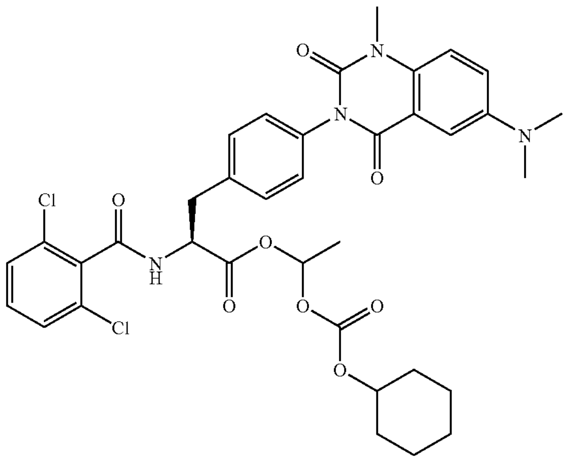

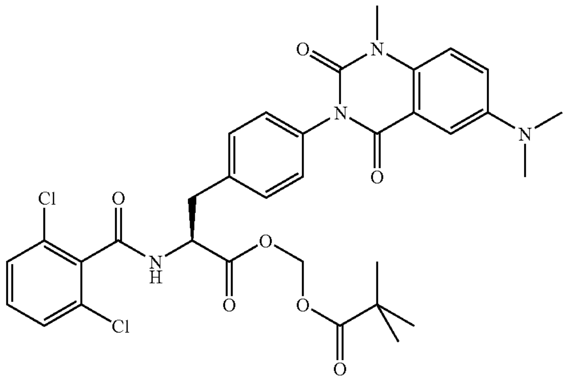

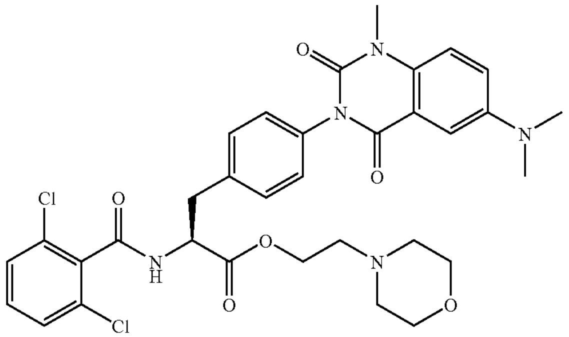

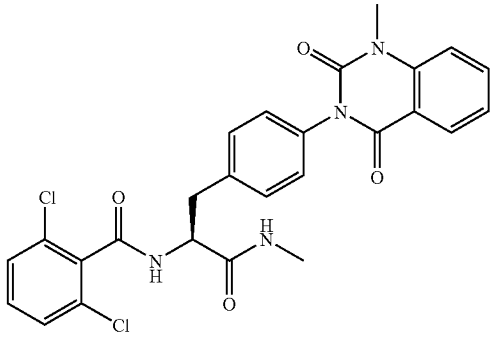

-continued
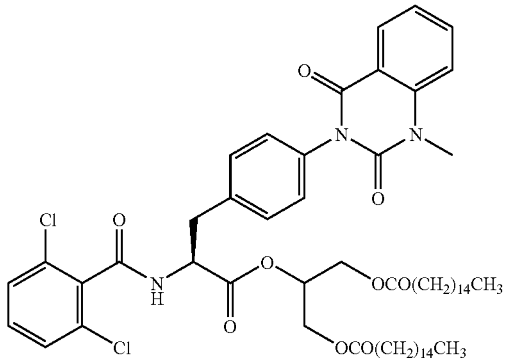
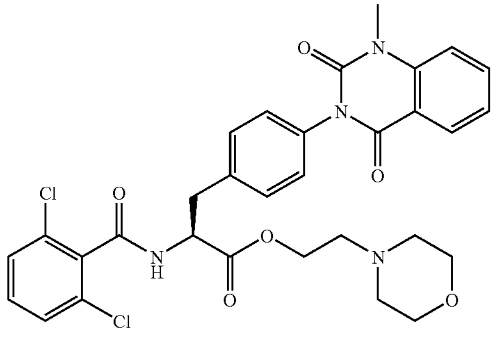
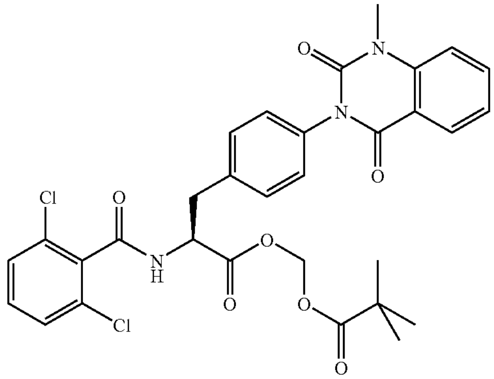
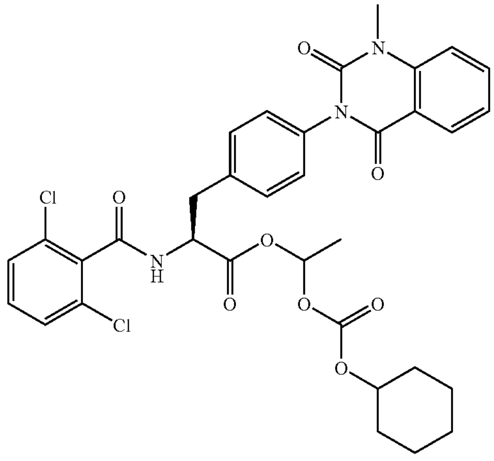
or a pharmaceutically acceptable salt thereof.
22. A phenylalanine compound according to claim 1 represented by the following one of the following formulae:
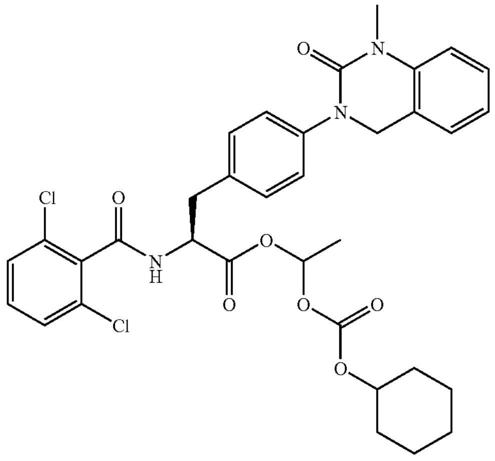
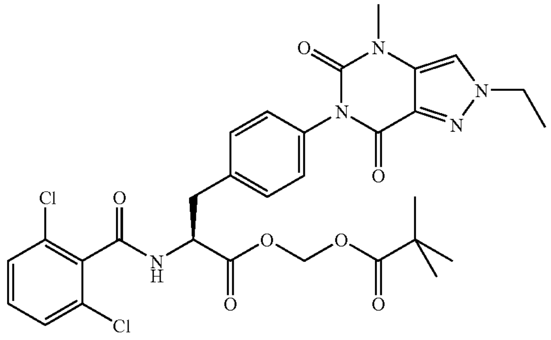
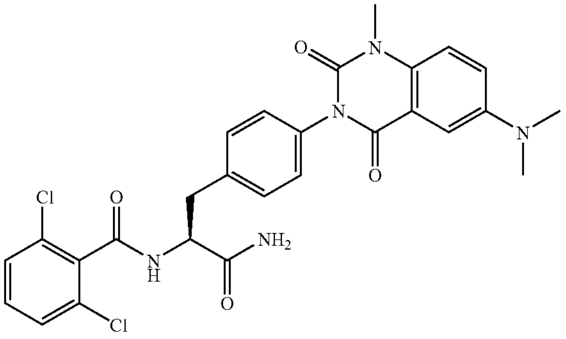
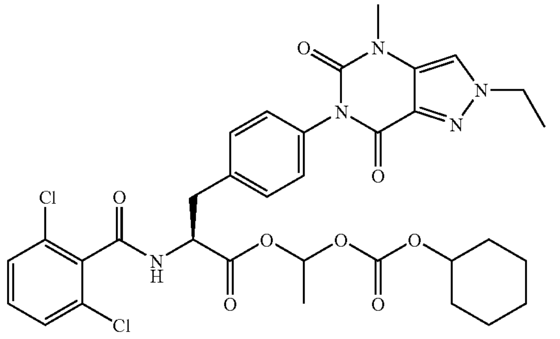

-continued
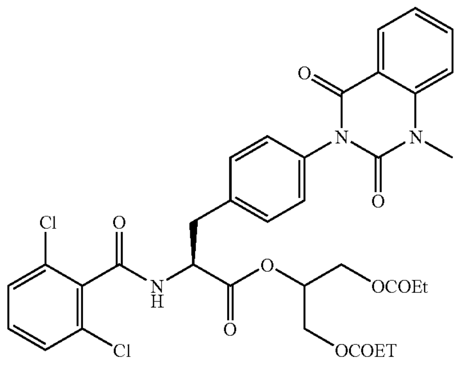
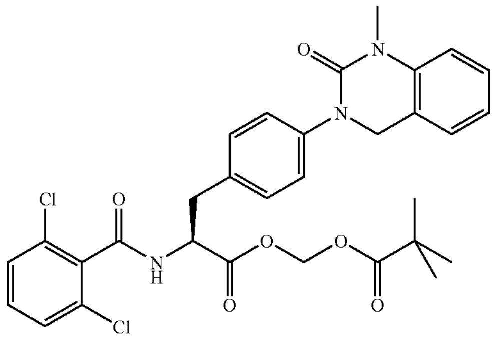
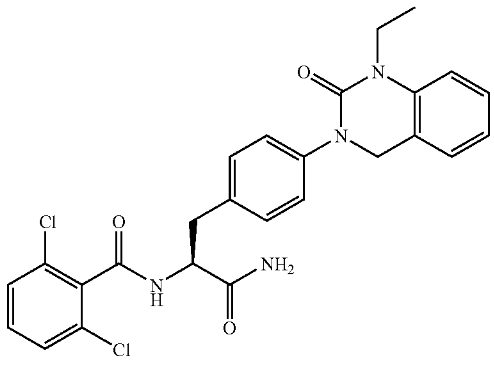
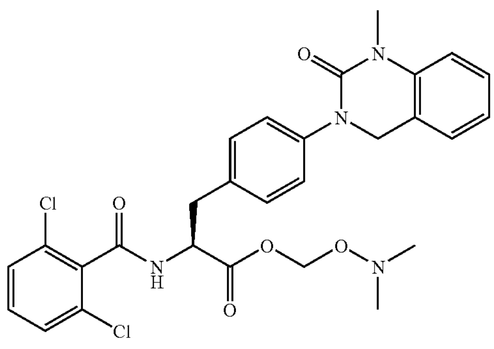
-continued
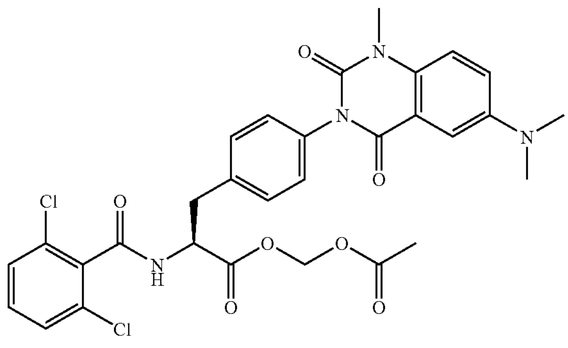
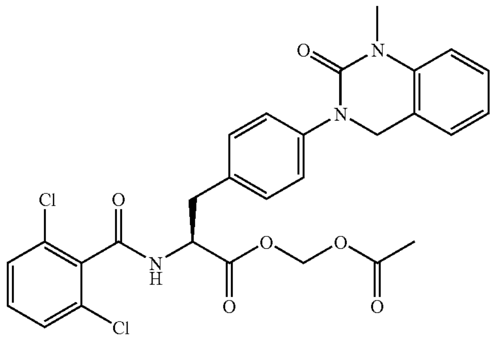
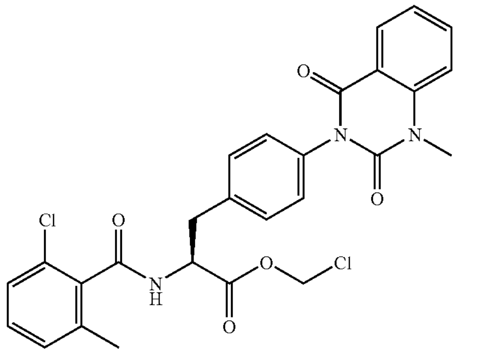
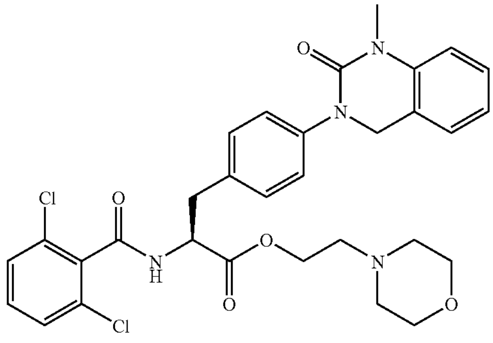

-continued

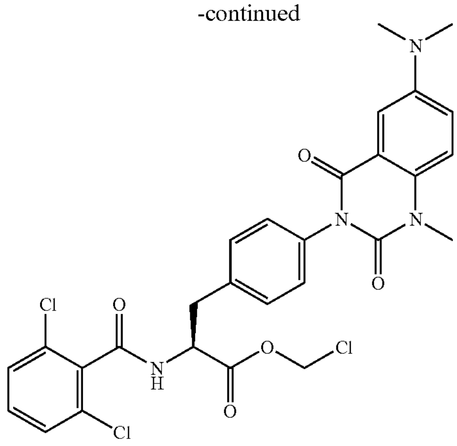

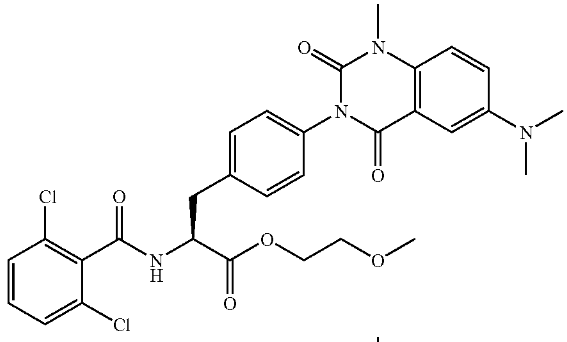

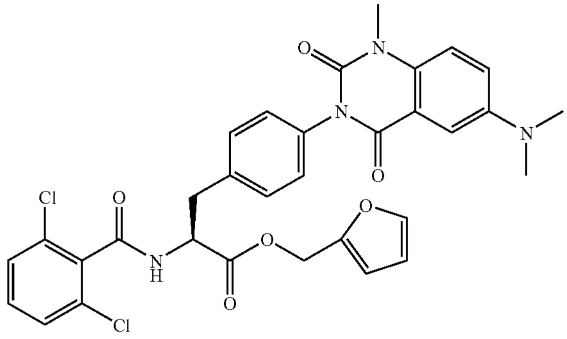

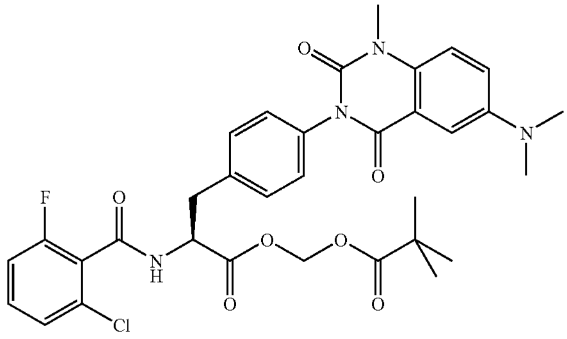

-continued

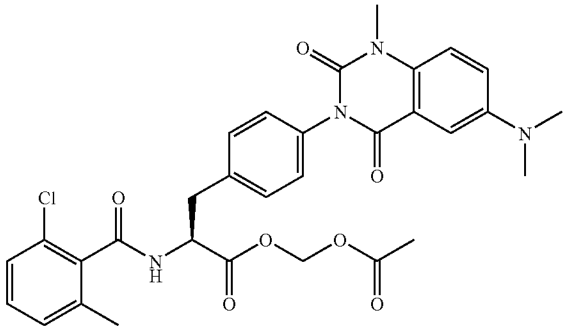

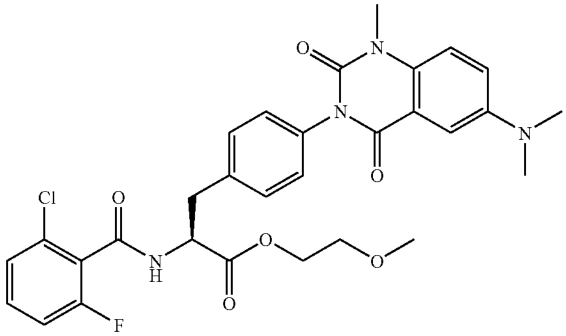

or a pharmaceutically acceptable salt thereof.

23. A pharmaceutical composition, comprising a phenylalanine derivative or pharmaceutically acceptable salt thereof according to claim 1 and a pharmaceutically acceptable adjunct.

24. A pharmaceutical composition, comprising a phenylalanine derivative or pharmaceutically acceptable salt thereof according to claim 2 and a pharmaceutically acceptable adjunct.

* * * * *